US006797265B2

(12) United States Patent
Amalfitano et al.

(10) Patent No.: US 6,797,265 B2
(45) Date of Patent: Sep. 28, 2004

(54) DELETED ADENOVIRUS VECTORS AND METHODS OF MAKING AND ADMINISTERING THE SAME

(75) Inventors: Andrea Amalfitano, Durham, NC (US); Yuan Tsong Chen, Chapel Hill, NC (US); Huimin Hu, Memphis, TN (US); Bradley Lowell Hodges, Milford, MA (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/972,794

(22) Filed: Oct. 5, 2001

(65) Prior Publication Data

US 2003/0165462 A1 Sep. 4, 2003

Related U.S. Application Data

(62) Division of application No. 09/384,749, filed on Aug. 27, 1999, now Pat. No. 6,328,958.
(60) Provisional application No. 60/145,742, filed on Aug. 28, 1998.

(51) Int. Cl.[7] .............................................. A61K 48/00

(52) U.S. Cl. ................ 424/93.2; 435/69.1; 435/320.1; 435/325

(58) Field of Search ...................... 424/93.2; 435/320.1, 435/91.4, 69.1, 325, 455; 514/44

(56) References Cited

U.S. PATENT DOCUMENTS

| | | | |
|---|---|---|---|
| 5,354,678 A | 10/1994 | Lebkowski et al. | 435/172.3 |
| 5,399,346 A | 3/1995 | Anderson et al. | 424/93.21 |
| 5,518,913 A | 5/1996 | Massie et al. | 435/235.1 |
| 5,585,362 A | 12/1996 | Wilson et al. | 514/44 |
| 5,670,488 A | 9/1997 | Gregory et al. | 514/44 |
| 5,674,722 A | 10/1997 | Mulligan et al. | 435/172.3 |
| 5,700,470 A | 12/1997 | Saito et al. | 424/233.1 |
| 5,707,618 A | 1/1998 | Armentano et al. | 424/93.21 |
| 5,731,172 A | 3/1998 | Saito et al. | 435/91.42 |
| 5,824,544 A | 10/1998 | Armentano et al. | 435/320.1 |
| 5,837,511 A | 11/1998 | Falck-Pedersen et al. | 435/172.3 |
| 5,849,561 A | 12/1998 | Falck-Pedersen | 435/235.1 |
| 5,851,806 A | 12/1998 | Kovesdi et al. | 435/91.41 |
| 5,877,011 A | 3/1999 | Armentano et al. | 435/320.1 |
| 5,880,102 A | 3/1999 | George et al. | 514/44 |
| 5,882,877 A | 3/1999 | Gregory et al. | 435/320.1 |
| 5,891,690 A | 4/1999 | Massie | 435/172.3 |
| 5,919,676 A | 7/1999 | Graham et al. | 435/172.3 |
| 5,922,576 A | 7/1999 | He et al. | 435/91.41 |
| 5,928,944 A | 7/1999 | Seth et al. | 435/375 |
| 5,980,886 A | 11/1999 | Kay et al. | 424/93.21 |
| 5,981,225 A | 11/1999 | Kochanek et al. | 435/69.1 |
| 5,981,275 A | 11/1999 | Armentano et al. | 435/320.1 |
| 5,994,106 A | 11/1999 | Kovesdi et al. | 435/91.4 |
| 5,994,132 A | 11/1999 | Chamberlain et al. | 435/369 |
| 5,998,205 A | 12/1999 | Hallenbeck et al. | 435/325 |
| 5,998,598 A | 12/1999 | Csaky et al. | 536/23.4 |
| 6,013,638 A | 1/2000 | Crystal et al. | 514/44 |
| 6,019,978 A | 2/2000 | Ertl et al. | 424/199.1 |
| 6,057,158 A | 5/2000 | Chamberlain et al. | 435/456 |
| 6,063,622 A | 5/2000 | Chamberlain et al. | 435/369 |
| 6,066,626 A | 5/2000 | Yew et al. | 514/44 |
| 6,083,750 A | 7/2000 | Chamberlain et al. | 435/369 |
| 6,328,958 B1 * | 12/2001 | Amalfitano | 424/93.2 |
| 6,492,343 B1 * | 12/2002 | Reddy | 514/44 |

FOREIGN PATENT DOCUMENTS

| | | |
|---|---|---|
| AU | 712304 | 4/1996 |
| WO | WO 90/07573 | 7/1990 |
| WO | WO 94/28152 | 12/1994 |
| WO | WO 96/10088 | 4/1996 |
| WO | WO 96/13597 | 5/1996 |
| WO | WO 98/13499 | 4/1998 |
| WO | WO 98/17783 | 4/1998 |

OTHER PUBLICATIONS

US 5,891,715, 4/1999, Haddada et al. (withdrawn)
Slemenda (Nucleic acids Res, vol. 18, No. 10, 1990).*
Oosterom–Dragon (J. of Virology, vol. 33, No. 3, pp. 1203–1207, 1980).*
Amalfitano et al.: Modification of Adenoviral Vectors for use in gene therapy of Duchenne Muscular Dystrophy, *The American Journal of Human Genetics* 57:4 Abstract #1354 Poster Symposium—Session 32 (1995).
Amalfitano et al.: Improved adenovirus packaging cell lines to support the growth of replication–defective gene–delivery vectors, *Proc. Natl. Acad. Sci.* USA 93:3352–3356 (1996).
Amalfitano et al.: Isolation and characterization of packaging cell lines that coexpress the adenovirus E1, DNA polymerase, and preterminal proteins: implications for gene therapy, *Gene Therapy* 4:258–263 (1997).

(List continued on next page.)

*Primary Examiner*—Dave Trong Nguyen
(74) *Attorney, Agent, or Firm*—Myers Bigel Sibley & Sajovec

(57) ABSTRACT

The present invention provides deleted adenovirus vectors. The inventive adenovirus vectors carry one or more deletions in the IVa2, 100K, polymerase and/or preterminal protein sequences of the adenovirus genome. The adenoviruses may additionally contain other deletions, mutations or other modifications as well. In particular preferred embodiments, the adenovirus genome is multiply deleted, i.e., carries two or more deletions therein. The deleted adenoviruses of the invention are "propagation-defective" in that the virus cannot replicate and produce new virions in the absence of complementing function(s). Preferred adenovirus vectors of the invention carry a heterologous nucleotide sequence encoding a protein or peptide associated with a metabolic disorder, more preferably a protein or peptide associated with a lysosomal or glycogen storage disease, most preferably, a lysosomal acid α-glucosidase. Further provided are methods for producing the inventive deleted adenovirus vectors. Further provided are methods of administering the deleted adenovirus vectors to a cell in vitro or in vivo.

75 Claims, 40 Drawing Sheets

OTHER PUBLICATIONS

Amalfitano et al.: A New class of adenoviurs vector: the [E1–, E2b–]Ad vector, *Molecular and Cellular Biology of Gene Therapy* E:6 24 (1997).

Amalfitano et al.: Production and Characterization of Improved Adenovirus Vectors with the E1, E2b, and E3 Genes Deleted, *Journal of Virology*, 72:2 926–933 (1998).

Amalfitano, Editorial, *Gene Therapy* 6:1643–1645 (1999).

Amalfitano et al.: Systemic correction of the muscle disorder glycogen storage disease type II after hepatic targeting of a modified adenovirus vector encoding human acid–α–glucosidase, *Proc. Natl. Acad. Sci. USA* 96:8861–8866 (1999).

Angeletti et al.: Adenovirus Preterminal Protein Binds to the CAD Enzyme at Active Sites of Viral DNA Replication on the Nuclear Matrix, *Journal Of Virology* 72:4 2896–2904 (1998).

Armentano et al.: Effect of the E4 Region on the Persistence of Transgene Expression from Adenovirus Vectors, *Journal Of Virology* 71:3 2408–2416 (1997).

Bett et al.: An efficient and flexible system for construction of adenovirus vectors with insertions or deletions in early regions 1 and 3, *Proc. Natl. Acad. Sci. USA* 91:8802–8806 (1994).

Brough et al.: Activation of Transgene Expression by Early Region 4 Is Responsible for a High Level of Persistent Transgene Expression from Adenovirus Vectors In Vivo, *Journal Of Virology* 71:12 9206–9213 (1997).

Byrne et al.; Gene replacement in acid maltase deficiency using DNA viral vectors, *Pediatric Research* 41:19a XP000934188 (1997).

Caravokyri et al.: Constitutive Episomal Expression of Polypeptide IX (pIX) in a 293–Based Cell Line Complement the Deficiency of pIX Mutant Adenovirus Type 5, *Journal Of Virology* 69:11 6627–6633 (1995).

Cepko et al.: Analysis of Ad5 Hexon and 100K ts Mutants Using Conformation–Specific Monoclonal Antibodies, *Virology* 129 137–154 (1983).

Chamberlain et al.: Packaging cells expressing the Adenovirus (Ad) E1, polymerase, and preterminal proteins to allow the growth of a new class of replication defective Ad–vector for use in Duchenne muscular dystrophy (DMD), *The American Journal of Human Genetics* 59:4 Abstract #2196 (1996).

Clemens et al.: In vivo muscle gene transfer of full–length dystrophin with an adenoviral vector that lacks all viral genes, *Gene Therapy* 3 965–972 (1996).

Cox et al.: Overexpression of dystrophin in transgenic mdx mice eliminates dystrophic symptoms without toxicity, *Nature* 364:725–729 (1993).

Dedieu et al.: Long–Term Gene Delivery into the Livers of Immunocompetent Mice with E1/E4–Defective Adenoviruses, *Journal Of Virology* 71:6 4626–4637 (1997).

Douglas et al.: A system for the propagation of adenoviral vectors with genetically modified receptor specificities, *Nature Biotechnology*, 17 470–475 (1999).

Elferink et al.: Isolation and characterization of a precursor form of lysosomal α–glucosidase from human urine, *Eur. J. Biochem.*, 139, 489–495 (1984).

Gao et al.: Biology of adenovirus Vectors with E1 and E4 Deletions for Liver–Directed Gene Therapy, *Journal Of Virology*, 70:12 8934–8943 (1996).

Gilgenkrantz et al.: Transient Expression of Genes Transferred In Vivo into Heart Using First–Generation Adenoviral Vectors: Role of the Immune Response, *Human Gene Therapy*, 6, 1265–1274 (1995).

Goldman et al.: Transfer of the CFTR Gene to the Lung of Nonhuman Primates with E1–Deleted, E2a–Defective Recombinant Adenoviruses: A Preclinical Toxicology Study, *Human Gene Therapy*, 6, 839–851 (1995).

Gorziglia et al.: Generation of an Adenovirus Vector Lacking E1, E2a, E3, and All E4 except Open Reading Frame 3, *Journal Of Virology*, 73:7, 6048–6055 (1999).

Graham et al.: Characteristics of a Human Cell Line Transformed by DNA from Human Adenovirus Type 5, *J. gen. Virol.*, 36, 59–72 (1977).

Guo et al.: Evaluation of promoter strength for hepatic gene expression in vivo following adenovirus–mediated gene transfer, *Gene Therapy*, 3, 802–810 (1996).

Guo et al.: Comparison of Viral Gene–Deleted Adenoviral Vectors With the E1–Deleted Adenoviral Vector in Islets, *Transplantation Proceedings*, 31, 794 (1999).

Hardy et al.: Construction of Adenovirus Vectors through Cre–lox Recombination, *Journal Of Virology*, 71:3, 1842–1849 (1997).

Hartigan–O'Connor et al.: Increased Efficiency Of Gutted Adenovirus Production In Cells Expressing Preterminal Protein and DNA Polymerase, American Society of Gene Therapy *Adenoviruses*, Abstract #703 (1998).

Hartigan–O'Connor et al.: Improved Production of Gutted Adenovirus in Cells Expressing Adenovirus Preterminal Protein and DNA Polymerase, *Journal Of Virology*, 73: 9, 7835–7841 (1999).

Hauser et al.: *Improved adenoviral vectors for gene therapy of Duchenne muscular dystrophy*, Neuromuscular Disorders 7, 277–283 (1997).

He et al.: A simplified system for generating recombinant adenoviruses, *Proc. Natl. Acad. Sci. USA*, 95, 2509–2514 (1998).

Hermans et al.: Man lysomal α–glucosidase: functional characterization of the cosylation sites, *M. J.*, 289, 681–686 (1993).

Hoefsloot et al.: Primary structure and processing of lysosomal α–glucosidase; homology with the intestinal sucrase—isomaltase complex, *The EMBO Journal*, 7:6, 1697–1704 (1988).

Hoefsloot et al.: Expression and routeing of human lysosomal α–glucosidase in transiently transfected mammalian cells, *Biochem. J.*, 272 485–492 (1990).

Hu et al.: Persistence of an [E1 , Polymerase] Adenovirus Vector Despite Transduction of a Neoantigen into Immune–Competent Mice, *Human Gene Therapy* 10, 355–364 (1999).

Ilan et al.: Insertion of the adenoviral E3 region into a recombinant viral vector prevents antiviral humoral and cellular immune responses and permits long–term gene expression, *Proc. Natl. Acad. Sci. USA*, 94, 2587–2592 (1997).

International Search Report; PCT/US99/19540.

Jones et al.: Isolation of Deletion and Substitution Mutants of Adenovirus Type 5, *Cell*, 13, 181–188 (1978).

Kaplan et al.: Characterization of Factors Involved in Modulating Persistence of Transgene Expression from Recombinant Adenovirus in the Mouse Lung, *Human Gene Therapy*, 8, 45–56 (1997).

Kochanek et al.: A new adenoviral vector: Replacement of all viral coding sequences with 28 kb of DNA independently expressing both full–length dystrophic and β–galactosidase, *Proc. Natl. Acad. Sci. USA*, 93, 5731–5736 (1996).

Krougliak et al.: Development of Cell Lines Capable of Complementing E1, E4, and Protein IX Defective Adenovirus Type 5 Mutants, *Human Gene Therapy*, 6 1575–1586 (1995).

Kumar–Singh et al. "Encapsidated adenovirus minichromosomes as gene–delivery vehicles," *American Journal of Human Genetics*. 59:Suppl 4 p. A202, ISSN: 0002–9297 (1996).

Kumar–Singh et al.: Encapsidated adenovirus minichromosomes allow delivery and expression of a 14 kb dystrophin cDNA to muscle cells, *Human Molecular Genetics* 5: 7, 913–921 (1996).

Kumar–Singh et al.: Encapsidated adenovirus mini–chromosome–mediated delivery of genes to the retina: application to the resuce of photoreceptor degeneration, *Human Molecular Genetics* 7:12, 1893–1900 (1998).

Langer et al.: 293 Cell Lines That Inducibly Express High Levels of Adenovirus Type 5 Precursor Terminal Protein, *Virology* 221, 172–179 (1996).*

Lieber et al.: Recombinant Adenoviruses with Large Deletions Generated by Cre–Mediated Excision Exhibit Different Biological Properties Compared with First–Generation Vectors In Vitro and In Vivo, *Journal Of Virology*, 70:12, 8944–8960 (1996).*

Lieber et al.: Adenoviral preterminal protein stabilizes mini–ade3noviral genomes in vitro and in vivo, *Nature Biotechnology*, 15 1383–1387 (1997).*

Löser et al.; "Reactivation of the previously silenced cyromegalovirus major immediate–early promoter in the mouse liver: involvement of NfkappaB," *J. Virol.* 72:1 180–190 (Jan. 1998).*

Lusky et al.: In Vitro and In Vivo Biology of Recombinant Adenovirus Vectors with E1, E1/EW2A, or E1/E4 Deleted, *Journal Of Virology*, 72:3, 2023–2032 (1998).*

Marienfeld et al.: 'Autoreplication' of the vector genome in recombinant adenoviral vectors with different E1 region deletions and transgenes, *Gene Therapy* 6, 1101–1113 (1999).*

Martin–Touaux et al.; "In vivo gene therapy of Pompe disease using an adenoviral vector," *American Journal of Human Genetics* 65:A310 (Oct. 1999).*

Martiniuk, et al.: Sequence of the cDNA and 5'–Flanking Region for Human Acid $_\alpha$–Glucosidase, Detection of an Intron in the 5' Untranslated Leader Sequence, Definition of 18–bp Polymorphisms and Differences with Previous cDNA and Amino Acid Sequences, *DNA and Cell Biology*, 9:2, 85–94 (1990).*

Martiniuk et al.., Recombinant Human Acid $_\alpha$–Glucosidase Generated in Bacteria; Antigenic, but Enzymatically Inactive, *DNA and Cell Biology* 11:9 701–706 (1992).*

Mathews; Control of Translation in Adenovirus–Infected Cells, *Enzyme* 44, 250–264 (1990).*

Maxwell et al.: An Adenovirus Type 5 Mutant with the Preterminal Protein Gene Deleted Efficiently Provides Helper Functions for the Production of Recombinant Adeno–Associated Virus, *Journal Of Virology*, 72:10, 8317–8373 (1998).*

Mccoy et al, Nucleotide and Amino Acid Sequence Analysis of the 100K Protein of a Serotype 3 Porcine Adenovirus, *DNA Sequence: The Journal of Sequencing and Mapping*, 8:1–2, 59–61 (1997).*

Mitani et al.: Rescue, propagation, and partial purification of a helper virus–dependent adenovirus vector, *Proc. Natl. Acad. Sci. USA* 92, 3854–3858 (1995).*

Moorhead et al.: A Replication–Incompetent Adenovirus Vector with the Preterminal Protein Gene Deleted Efficiently Transduces Mouse Ears, *Journal Of Virology*, 73:2, 1046–1053 (1999).*

Morin et al.: Hexon Trimerization Occurring in an Assembly–Defective, 100K Temperature–Sensitive Mutant of Adenovirus 2, *Virology*, 152, 11–31 (1986).*

Morral et al.: Immune Responses to Reporter Proteins and High Viral Dose Limit Duration of Expression with Adenoviral Vectors: Comparison of E2a Wild Type and E2a Deleted Vectors, *Human Gene Therapy*, 8, 1275–1286 (1997).*

Nakano et al.: Overproduction of adenovirus DNA polymerase and preterminal protein in HeLa cells, *Gene* 105, 173–178 (1991).

Natarajan et al.; *Proximal and distal domains that control in vitro transcription of the adenovirus Iva2 gene,* Proc. Natl. Acad. Sci. USA 81:6290–6294 (Oct. 1984).

Nevins; Mechanism of Activation of Early Viral Transcription by the Adenovirus E1A Gene Product, *Cell* 26 213–220 (1981).

Nicolino et al.; "Adenovirus–mediated transfer of the acid alpha–glucosidase gene into fibroblasts, myoblasts and myotubes from patients with glycogen storage disease type II leads to high level expression of enzyme and corrects glycogen accumulation," *Hum Mol Genet.* 7:11 1695–1702 (Oct. 1998).

Niwa et al.: In vitro polyadenylation is stimulated by the presence of an upstream intron, *Gene & Development*, 1552–1559 (1990).

Ohashi et al.: Adenovirus–mediated gene transfer and expression of human β–glucuronidase gene in the liver, spleen, and central nervous system mucopolysaccharidosis type VII mice, *Proc. Natl. Acad. Sci. USA* 94, 1287–1292 (1997).

Oosterom–Dragon et al.: Purification and Preliminary Immunological Characterization of the Type 5 Adenovirus, Nonstructural 100,000–Dalton Protein, *Journal Of Virology*, 33:3, 1203–1207 (1980).

Oosterom–Dragon et al.: Characterization of Two Temperature–Sensitive Mutants of Type 5 Adenovirus with Mutations in the 1000,000–Dalton Protein Gene, *Journal Of Virology*, 40:2, 491–500 (1981).

Parks et al.: A helper–dependent adenovirus vector system: Removal of helper virus by Cre–mediated excision of the viral packaging signal, *Proc. Natl. Acad. Sci. USA*, 93, 13565–13570 (1996).

Pauly et al.: Complete correction of acid $_\alpha$–glucosidase deficiency in Pompe disease fibroblast in vitro, and lysosomally targeted expression in neonatal rat cardiac and skeletal muscle, *Gene Therapy*, 5 473–470 (1998).

Pettit et al.: Adenovirus Preterminal Protein Synthesized in COS Cells from Cloned DNA Is Active in DNA Replication In Vitro, *Journal Of Virology*, 62:2 496–500 (1988).

Ragot et al.: Efficient adenovirus–mediated transfer of a human minidystrophin gene to skeletal muscle of mdx mice, *Nature* 361, 647–650 (1993).

Ramachandra et al.: [10] Heterologous Expression, Purification, and Characterization of Adenovirus DNA Polymerase and Preterminal Protein, *Methods in Enzymology* 275 168–194 (1996).

Raper et al.: Selective Gene Transfer into the Liver of Non–Human Primates with E1–Deleted, E2A–Defective, or E1–E4 Deleted Recombinant Adenoviruses, *Human Gene Therapy* 9, 671–679 (1998).

Raper et al.: Developing adenoviral–mediated in vivo gene therapy for ornithine transcarbamylase deficienty, *J. Inher. Metab. Dis.* 21 (Suppl 1), 119–137 (1998).

Reuser et al.: Uptake and Stability of Human and Bovine Acid $_\alpha$–Glucosidase in Cultured Fibroblasts and Skeletal Muscle Cells from Glycogenosis Type II Patients, *Experimental Cell Research,* 155, 178–189 (1984).

Rich et al.: Development and Analysis of Recombinant Adenoviruses for Gene Therapy of Cystic Fibrosis, *Human Gene Therapy* 4 461–476 (1993).

Riley et al.: RNA–Binding Properties of a Translational Activator, the Adenovirus L4 100–Kilodalton Protein, *Journal Of Virology,* 67:6, 3586–3595 (1993).

Rittner et al.: Conditional Repression of the E2 Transcription Unit in E1–E3–Deleted Adenovirus Vectors Is Correlated with a Strong Reduction in Viral DNA Replication and Late Gene Expression In Vitro, *Journal Of Virology,* 71:4, 3307–3311 (1997).

Scaria et al.: Complementation of a human adenovirus early region 4 deletion mutant in 293 cells using adenovirus–polylysine–DNA complexes, *Gene Therapy,* 2, 295–298 (1995).

Schaack et al.: Adenovirus terminal protein mediates both nuclear matrix association and efficient transcription of adenovirus DNA, *Genes & Development* 4, 1197–1208 (1990).

Schaack et al.: Adenvirus Type 5 Precursor Terminal Protein–Expressing 293 and HeLa Cell Lines, *Journal Of Virology,* 69:7, 4079–4085 (1995).

Schaack et al.: Characterization of a replication–incompetent adenovirus type 5 mutant deleted for the preterminal protein gene, *Proc. Natl. Acad. Sci. USA* 93, 14686–14691 (1996).

Slemenda et al.: Nucleotide sequence of the region coding for 100K and 33K proteins of human enteric adenovirus type 41 (Tak), *Nucleic Acids Research* 18:10, 3069 (1990).

Sudhanshu et al.: Sequence of Ovine Adenovirus Homologs for 100k Hexon Assembly, 33K, pVIII, and Fiber Genes: Early Region E3 Is Not in the Expected Location, *Virology* 209, 400–408 (1995).

Thomas et al.: DNA Replication and the Early to Late Transition in Adenovirus Infection, *Cell* 22 523–533 (1980) (Page 2).

Tribouley et al.: The Product of the Adenovirus Intermediate Gene Iva2 Is a Transcriptional Activator of the Major Lat Promoter, *Journal Of Virology* 68:7, 4450–4457 (1994).

Tripathy et al.: Stable delivery of physiologic levels of recombinant erythropoietin to the systemic circulation by intramuscular injection of replication–defective adenovirus, *Proc. Natl. Acad. Sci. USA,* 91, 11557–11561 (1994).

Tripathy et al.: Immune responses to transgene–encoded proteins limit the stability of gene expression after injection of replication–defective adenovirus vectors, *Nature Medicine* 2:5, 545–550 (1996).

Tsujino et al.: Adenovirus–Mediated Transfer of Human Acid Maltase Gene Reduces Glycogen Accumulation in Skeletal Muscle of Japanese Quail with Acid Maltase Deficiency, *Human Gene Therapy,* 9 1609–1616 (1998).

Van der Ploeg et al.: Prospect for enzyme therapy in glycogenosis II variants: a study on cultured muscle cells, *J. Neurol.* 235 392–396 (1988).

Van der Ploeg et al.: Intravenous Administration of Phosphorylated Acid $_\alpha$–Glucosidase Leads to Uptake of Enzyme in Heart and Skeletal Muscle of Mice, *J. Clin. Invest.* 87, 513–518 (1991).

Van Hove et al.: High–level production of recombinant human lysosomal acid α–glucosidase in chinese hamster ovary cells which targets to heart muscle and corrects glycogen accumulation in fibroblasts from patients with Pompe disease, *Proc. Natl. Acad. Sci. USA,* 93, 65–70 (1996).

Vincent et al.: Long–term correction of mouse dystrophic degeneration by adenovirus–mediated transfer of a minidystrophin gene, *nature genetics* 5, 130–134 (1993).

von Seggern et al.: A Helper–Independent Adenovirus Vector with E1, E3 and Fiber Deleted: Structure and Infectivity of Fiberless Particles, *Journal Of Virology,* 73:2, 1601–1608 (1999).

Vrati et al.: Sequence of Ovine Adenovirus Homologs for 100K Hexon Assembly, 33K, pVIII, and Fiber Genes, Early Region E3 Is Not in the Expected Location, *Virology* 209:400–408 (1995).

Wang et al.: A packaging cell line for propagation of recombinant adenovirus vectors containing two lethal gene–region deletions, *Gene Therapy,* 2, 775–783 (1995).

Wang et al.: Persistent transgene expression in mouse liver following in vivo gene transfer with a ΔE1/ΔE4 adenovirus vector, *Gene Therapy,* 4, 393–400 (1997).

Webster et al.: Domain Organization of the Adenovirus Preterminal Protein, *Journal Of Virology,* 71:1, 539–547 (1997).

Webster et al.: Role of Preterminal Protein Processing in Adenovirus Replication, *Journal Of Virology,* 71:9, 6381–6389 (1997).

Wisselaar et al.: Structural and Functional Changes of Lysosomal Acid $_\alpha$–Glucosidase during Intracellular Transport and Maturation, *The Journal Of Biological Chemistry,* 268:3, 2223–2231 (1993).

Wolff et al.: Long–term persistence of plasmid DNA and foreign gene expression in mouse muscle, *Human Molecular Genetics,* 1:6, 363–369 (1992).

Yang et al.: Cellular immunity to viral antigens limits E1–deleted adenoviruses for gene therapy, *Proc. Natl. Acad. Sci. USA,* 91, 4407–4411 (1994).

Yang et al.: Inactivation of E2a in recombinant adenoviruses improves the prospect for gene therapy in cystic fibrosis, *Nature Genetics,* 7, 362–369 (1994).

Yang et al.: MHC Class I–Restricted Cytotoxic T Lymphocytes to Viral Antigens Destroy Hepatocytes in Mice Infected with E1–Deleted Recombinant Adenoviruses, *Immunity* 1 433–442 (1994).

Yang et al; Cellular and Humoral Immune Responses to Viral Antigens Create Barriers to Lung–Directed Gene Therapy with Recombinant Adenoviruses, *Journal Of Virology,* 69:4, 2004–2015 (1995).

Yang et al.: Clearance of Adenovirus–Infected Hepatocytes by MHC Class I–Restricted CD4[+] CTLs In Vivo, *The Journal of Immunology,* 2564–2569 (1995).

Yang et al.: Role of Viral Antigens in Destructive Cellular Immune Responses to Adenovirus Vector–Transduced Cells in Mouse Lungs, *Journal of Virology,* 70:10, 7209–7212 (1996).

Yeh et al.: Efficient Dual Transcomplementation of Adenovirus E1 and E4 Regions from a 293–Derived Cell Line Expressing a Minimal E4 Functional Unit, *Journal Of Virology,* 70:1, 559–565 (1996).

Zhao et al.: Synthesis of biologically active adenovirus preterminal protein in insect cells using a baculovirus vector, *Gene,* 100 147–154 (1991).

Zhou et al.: Development of a Complementing Cell Line and a System for Construction of Adenovirus Vectors with E1 and E2a Deleted, *Journal Of Virology,* 70:10, 7030–7038 (1996).

Rosenberg, "The Immunotherapy of Solid Cancers Based on Cloning the genes Encoding Tumor–Rejection Antigens," *Annu. Rev. Med* 47: 481–491 (1996).

* cited by examiner

A.
B.
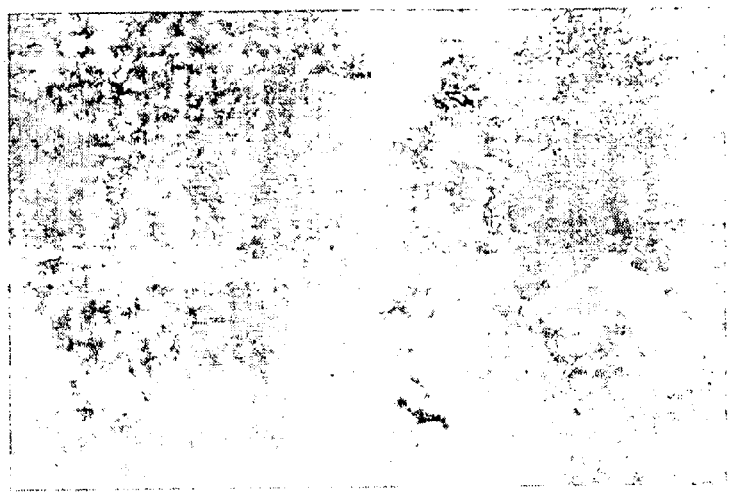
FIG. 9

SEQUENCE LISTING

<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tccaggccat ctccaaccat                        20

<210> SEQ ID NO 2
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 2
tctcagtctc catcatcatc acg                    23

DELETED ADENOVIRUS VECTORS AND METHODS OF MAKING AND ADMINISTERING THE SAME

RELATED APPLICATIONS INFORMATION

This application is a divisional application of co-pending U.S. application Ser. No. 09/384,749, filed on Aug. 27, 1999 now U.S. Pat. No. 6,328,958: which claims the benefit of U.S. Provisional Application Serial No. 60/145,742, filed on Aug. 28, 1998, the disclosures of which are incorporated by reference herein in their entireties.

FEDERAL SUPPORT

Government support for this invention was provided by Grant Number DK52925-02 from the National Institutes of Health. The government has certain rights to this invention.

FIELD OF THE INVENTION

The present invention relates to adenovirus vectors, more particularly, to propagation-defective adenovirus vectors.

BACKGROUND OF THE INVENTION

The basis of gene therapy is to deliver a functional gene to tissues where the respective gene activity is missing or defective. Among the approaches to accomplishing gene therapy has been the use of recombinant viral vectors which have been genetically engineered to carry a desired transgene. These viral-based vectors have advantageous characteristics, such as the natural ability to infect the target tissue. However, implementation of existing viral vectors are impeded by several limitations as well.

For example, retrovirus-based vectors must integrate into the genome of the target tissue to allow for transgene expression (with the potential to activate resident oncogenes) while vector titers produced in such systems are significantly less than in some other systems. Because of the requirement for integration into the subject genome, the retrovirus vector can only be used to transduce actively dividing tissues. Further, many retroviruses have limited host tissue specificity and cannot be employed to transduce more than a few specific tissues of the subject.

Adenovirus vectors hold great promise for gene therapy. Adenovirus vectors can transduce multiple types of tissues in vivo, including nondividing, differentiated cells such as those found in liver, kidney, muscle (skeletal and cardiac), respiratory, and nervous system tissues. See, e.g., Askari et al., *Gene Ther.* 3:381–388 (1996); Barr et al., *Gene Ther.* 1:51–58 (1994); Engelhardt et al., *Hum. Gene Ther.* 4:759–769 (1993). Using transcomplementing packaging cell lines, first generation Adenovirus vectors can be grown and concentrated to high titers ($>10^{13}$), which contributes to their ability to transduce large numbers of target cells after in vivo administration. Ragot, et al., *Nature* 361:647–50 (1993).

First generation adenovirus vectors also have a comparatively large carrying capacity (i.e., up to about 8.0 kb). The ability of first generation Adenovirus vectors to allow expression of transduced genes episomally for extended periods of time in immune-incompetent and sometimes immune-competent animals without the need for integration into the vector genome (Vincent, et al., *Nat Genet.* 5:130–34 (1993); Tripathy, et al., *Nature Medicine* 2:545–50 (1996)) allows them to transduce mitotically quiescent cells as well as actively dividing cells. Finally, live Adenovirus preparations have been used for the vaccination of military recruits, and Ad strains 2 and 5 (most commonly used for vector development) are not associated with severe disease.

Despite the advantages discussed above, first generation, E1-deleted adenovirus virus vectors are limited in potential therapeutic use for several reasons. First, due to the size of the E1 deletion and to physical virus packaging constraints, first generation adenovirus vectors are limited to carrying approximately 8.0 kb of transgene genetic material. While this compares favorably with other viral vector systems, it limits the usefulness of the vector where a larger transgene is required. Second, infection of the E1-deleted first generation vector into packaging cell lines leads to the generation of some replication competent adenovirus particles, because only a single recombination event between the E1 sequences resident in the packaging cell line and the adenovirus vector genome can generate a wild-type virus. Therefore, first-generation adenovirus vectors pose a significant threat of contamination of the adenovirus vector stocks with significant quantities of replication competent wild-type virus particles, which may result in toxic side effects if administered to a gene therapy subject.

The most difficult problem with adenovirus vectors is their inability to sustain long-term transgene expression, secondary to immune responses that eliminate virally transduced cells in immune-competent animals. Gilgenkrantz et al., *Hum. Gene Ther.* 6:1265–1274 (1995); Yang et al., *J. Virol.* 69:2004–2015 (1995); Yang et al., *Proc. Natl. Acad. Sci. USA* 91:4407–4411 (1994); Yang et al., *J. Immunol.* 155: 2565–2570 (1995). While immune responses have been demonstrated against the transgene-encoded protein product (Tripathy et al., *Nat. Med.* 2; 545–550 (1996)), it has also been demonstrated that adenovirus vector epitopes are major factors in triggering the host immune response. Gilgenkrantz et al., *Hum. Gene Ther.* 6:1265–1274 (1995); Yang et al., *J. Virol.* 70: 7209–7212 (1996). It has been repeatedly demonstrated that transgene such as the bacterial β-galactosidase gene are highly immunogenic when transduced by adenovirus vectors, in contrast to other delivery systems (e.g., direct DNA injection or adeno-associated virus administration), where an immune response against the immunogenic transgene is lacking and transgene expression persists. Wolff et al., *Hum. Mol. Genet.* 1:363–369(1992); Xiao et al., *J. Virol.* 70:8098–8108 (1996).

In addition, E1$^-$ vectors have also been reported to express the adenovirus early genes, undergo genome replication and express the L1-L5 encoded structural genes when utilized in vivo. E.g., Yang, et al., *Immunity* 1: 433–442 (1994). Because only a single recombination event is required to produce an entirely replication competent virus from the E-1 deletion, the exaggerated immune response may also be due in some instances to the contaminating presence of wild type adenovirus virus in the vector preparation. E.g., Rich, *Hum. Gene. Ther.* 4: 461–476 (1993). Either (or both) of these phenomena result in the production and presence of viral proteins in the transduced cells, possibly creating a higher antigenic profile than other gene therapy vector systems. The presence of these adenovirus viral gene products may contribute to the short duration of transgene expression in cells infected by first generation adenovirus vectors by accelerating the detection and elimination of adenovirus vector infected cells by the host immune system.

Accordingly, there remains a need in the art for improved adenovirus vector systems that address the limitations of existing systems.

SUMMARY OF THE INVENTION

The present invention provides novel deleted adenovirus vectors that provide advantages over existing "first-generation" adenovirus vectors. The deleted adenovirus vectors of the present invention may advantageously have an increased carrying capacity for heterologous nucleotide sequences, demonstrate lower levels of viral protein expression, induce fewer host immune responses, and/or exhibit increased stability and prolonged transgene expression when introduced into target cells.

The inventive adenovirus vectors carry one or more deletions in the IVa2, 100K, polymerase and/or preterminal protein sequences of the adenovirus genome. The adenoviruses may additionally contain other deletions, mutations or modifications as well. In particular preferred embodiments, the adenovirus genome is multiply deleted, i.e., carries two or more deletions therein. More preferably, there are deletions in two or more regions of the adenovirus genome (e.g., E1, E3, polymerase, 100K, IVa2, preterminal protein, etc.). At least one of the deletions in the adenovirus genome renders the adenovirus "propagation-defective" in that the virus cannot replicate and produce new virions in the absence of complementing function(s); preferably the vector carries multiple (two or more) deletions that result in a propagation-defective phenotype. When introduced into a trans-complementing cell that provides the deleted functions from the adenovirus genome, the deleted adenoviruses of the invention can produce a productive infection that results in the generation of new virus particles.

A further aspect of the present invention is methods for producing high-titers of the inventive deleted adenovirus vectors using packaging cells. Methods are also disclosed for producing the inventive deleted vectors using bacterial recombination and methods for producing "gutted" adenovirus vectors using deleted helper adenoviruses. Gutted adenovirus stocks according to the invention may exhibit increased stability and reduced viral protein expression from contaminating helper viruses as compared with previous preparations.

The inventive vectors can be administered to cells in vitro, e.g., to produce a protein/peptide or RNA of interest. In particular, a recombinant deleted adenovirus vector according to the invention may be administered to a cell in vitro, whereupon the cell expresses a heterologous nucleotide sequence. In particular embodiments, the nucleotide sequence encodes a protein or peptide (e.g., an enzyme) that is related to a metabolic disorder and/or a lysosomal or glycogen storage disorder. The expressed protein or peptide can be isolated, e.g., for protein replacement therapies.

In other embodiments, the recombinant adenovirus vectors of the invention may be administered to a cell in vitro and the cell administered to a subject, e.g., to produce an immunogenic or therapeutic response in the subject. In further alternative embodiments, the inventive deleted adenovirus vectors are administered directly to the subject. In particular, the present investigations have determined that intravenous administration to GAA-deficient animals of deleted adenovirus vectors of the invention carrying a GAA gene resulted in high-level transduction of liver cells and subsequent expression of the GAA transgene. Hepatic expression of GAA produced elevated plasma levels of GAA protein and significant reductions in glycogen levels in affected tissues.

The present invention also discloses methods of administering a recombinant deleted adenovirus vector of the invention into an organ or tissue, whereby a heterologous nucleotide sequence is expressed and the encoded protein/peptide or RNA is delivered to a different organ or tissue, e.g., to produce an immunogenic of therapeutic effect. For example, a nucleotide sequence encoding a foreign protein can be delivered to the liver, whereupon it is expressed and secreted into the circulatory system and delivered to target tissues (e.g., muscle). As a further alternative, the inventive adenovirus vectors can be introduced into the brain (e.g., by direct injection) for delivery of foreign proteins or nucleotide sequences to the central nervous system.

A further aspect of the invention is methods of expressing a protein or peptide in the liver for delivery to a distal tissue or organ (e.g., muscle tissue) to provide a therapeutic effect therein. Preferably, a deleted adenovirus of the invention is employed to introduce a nucleotide sequence encoding the protein or peptide into the liver. Also preferred are nucleotide sequences encoding proteins or peptides associated with a metabolic disorder, more preferably a lysosomal or glycogen storage disease (e.g., lysosomal acid α-glucosidase). Further preferred are nucleotide sequences encoding lysosomal proteins or peptides.

These and other aspects of the invention are set forth in more detail in the description of the invention below.

BRIEF DESCRIPTION OF THE DRAWINGS

FIG. 1A: pBHG11Δpol, FIG. 1B: AdΔpol and AdΔpol/pBHG11, and FIG. 1C: AdLacZΔpol.

FIG. 9 shows expression of the lacZ gene in vivo (A) after infection of BALB/c mice as compared with (B) mock-infected control.

DETAILED DESCRIPTION OF THE INVENTION

Figure 1A:
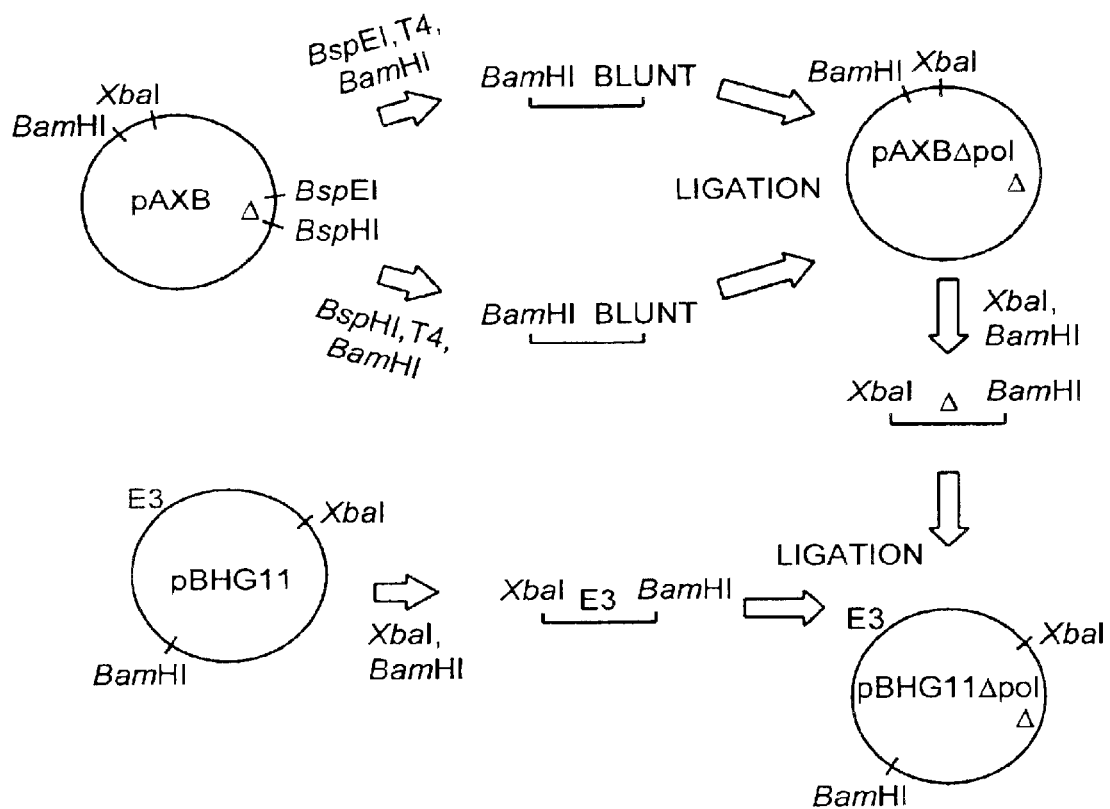
FIGS. 1A–1C show a diagrammatic representation of the steps utilized to isolate respectively

One strategy for overcoming the limitations of the currently available adenovirus vector systems is to introduce further deletions in essential gene regions of the adenovirus vector backbone. The addition of further deletions may increase the transgene carrying capacity of the vector and, if properly chosen, may reduce or eliminate recombination events which cause the contamination of viral stocks with propagation-competent wild type viral particles, thereby rendering these viral preparations unsuitable for therapeutic purposes.

Use of "second-generation" deleted adenovirus vectors may also address another significant problem of adenovirus vectors—the inability to sustain long term expression of transgenes after transfer into immune-competent animals, due to host immune responses and/or promoter shutdown (Yang et al., (1994) Proc. Natl. Acad. Sci. USA 91:4407; Yang et al., (1995) J. Virol. 69:2004; Yang et al, (1995) J. Immunol. 155:2564; Gilgenkranz et al., (1995) Human Gene Therapy 6:1265; Brough et al, (1997) J. Virol. 71:9206). The host immune responses following transduction with first-generation E1-deleted adenovirus vectors have been demonstrated to be directed against both transgene and adenovirus-vector encoded epitopes (Tripathy et al., (1996) Nature Medicine 2:545; Gilgenkranz et al., (1995) Human Gene Therapy 6:1265; Yang et al. (1996) J. Virol. 70:7209). It appears that first generation adenovirus vectors elicit an exaggerated host immune response. For example, adenovirus mediated transfer of the bacterial β-galactosidase gene has been demonstrated to be highly immunogenic in immune-competent animals, in contrast to other delivery systems such as direct DNA injection or adeno-associated virus administration, where an immune response to β-galactosidase has been demonstrated to be conspicuously lacking (Xiao et al., (1996) J. Virol. 70:8098; Wolff et al., (1996) Hum. Mol. Genet. 1:363).

The deleted adenovirus vectors of the present invention may reduce or eliminate viral DNA replication and/or viral gene product production when infected into the target cells as compared with first-generation E1-deleted vectors. While not wishing to be held to any particular theory of the invention, it appears that reduced viral replication advantageously results in prolonged transgene expression following transduction with the deleted adenovirus vectors of the invention. Reduced viral specific activities following vector transduction and transgene expression may also result in reduced host immune responses and cytotoxic effects on the host cell. These, in turn, may result in a longer duration of transgene expression.

Use of the vectors of the present invention may also dramatically reduce the host immune response to the transduced cells by offering a more effective blockage of viral DNA replication and viral gene expression. This may eliminate or reduce the need for administration of non-specific (and sometimes toxic) immunosuppressive agents in clinical adenovirus-based gene therapy protocols. While immune responses to adenovirus-based gene therapy vary depending on the background strain of the animal tested, the promoter/enhancer elements utilized to drive expression of the transgene, and the viral backbone itself, the dramatic improvement seen in the vectors of the present invention may significantly improve performance by reducing the immunologic profile of the transduced cells over earlier generation vectors regardless of these factors.

Moreover, use of the second-generation vectors may increase the transgene carrying capacity of adenovirus vectors to 9 kb, 11 kb, or even 12.5 kb or more from the current limit of 8 kb. This increased carrying capacity is advantageous when considering the transfer of larger cDNA minigene constructs (e.g., dystrophin), the utilization of larger, tissue-specific promoter/enhancer elements (e.g., the muscle-creatine kinase enhancer), and the reintroduction into vectors of adenovirus genes that may minimize immune recognition of adenovirus infected cells in vivo (e.g., the E4 gene) (Cox et al., (1993) *Nature* 364:725; Ilan et al., (1997) *Proc. Natl. Acad. Sci. USA* 94:2587; Kumarsingh et al., (1996) *Human Molecular Genetics* 5:913).

Further, the introduction of multiple deletions may reduce the likelihood of contamination of the resulting vector stocks by replication competent viruses since multiple recombination events would be required to regenerate a viable virus from a multiply-deleted virus.

Surprisingly, the deleted adenovirus vectors of the present invention are not unstable. This contrasts with the reports that gutted adenovirus vector depend on preterminal protein activity for genomic stability (Lieber et al., (1996) *J. Virol.* 70:8944; Lieber et al., (1997) *Nature Biotech.* 15:1383).

I. Deleted Adenovirus Vectors.

The present invention is based, in part, on the discovery of novel adenovirus vectors containing deletions within the adenovirus polymerase (pol), preterminal protein (pTP), 100K, and IVa2 regions of the adenovirus genome. These novel "second-generation" adenovirus vectors should be less "leaky" when transduced into target cells (e.g., for gene therapy) and be able to carry larger heterologous nucleotide sequences than previously-described E1 deleted adenovirus vectors. In addition, the deleted adenovirus vectors of the present invention may be less immunogenic, and thereby less susceptible to immune clearance, than the E1 deleted vectors previously known in the art.

The term "adenovirus" as used herein is intended to encompass all adenoviruses, including the Mastadenovirus and Aviadenovirus genera. To date, at least forty-seven human serotypes of adenoviruses have been identified (see, e.g., FIELDS et al., VIROLOGY, volume 2, chapter 67 (3d ed., Lippincott-Raven Publishers). Preferably, the adenovirus is a serogroup C adenovirus, still more preferably the adenovirus is serotype 2 (Ad2) or serotype 5 (Ad5).

In one preferred embodiment, the inventive adenoviruses of the present invention are infectious, but propagation-defective, i.e., they cannot replicate and package new virions in the absence of transcomplementation, e.g., by a packaging cell that expresses the functions deleted from the adenovirus genome. Alternatively stated, the propagation-defective adenoviruses of the invention cannot produce a productive infection in the absence of transcomplementation. The propagation-defective adenovirus particles carry an adenovirus genome that has one or more deletions in one or more of the 100K, IVa2, and/or preterminal protein regions. The deletion(s) in the adenovirus genome preferably prevents, or essentially prevents, the expression of a functional form of the indicated protein from the deleted region. For example, the 100K deletion preferably prevents, or essentially prevents, the expression of a functional 100K protein from the deleted 100K region of the adenovirus genome. The IVa2 deletion preferably prevents, or essentially prevents, the expression of a functional IVa2 protein from the deleted IVa2 region of the adenovirus genome. The preterminal protein deletion preferably prevents, or essentially prevents, the expression of a functional preterminal protein from the deleted preterminal protein region of the adenovirus genome.

By "infectious", as used herein, it is meant that the adenoviruses can enter the cell by natural transduction mechanisms and express the transgene therein. Alternatively, an "infectious" adenovirus is one that can enter the cell by other mechanisms and express the transgene therein. As one illustrative example, the vector can enter a target cell by expressing a ligand or binding protein for a cell-surface receptor in the adenovirus capsid or by using an antibody(ies) directed against molecules on the cell-surface followed by internalization of the complex, as is described hereinbelow.

In an alternate preferred embodiment, the propagation-defective adenovirus includes one or more deletions in the E1 region and one or more deletions in the polymerase region of the adenovirus genome. The polymerase deletion preferably prevents, or essentially prevents, the expression of a functional polymerase protein from the deleted polymerase region of the adenovirus genome. The E1 deletion(s) preferably prevents, or essentially prevents, the expression of a functional form of at least one E1 protein.

In another preferred embodiment, the present invention provides a deleted propagation-defective adenovirus comprising one or more deletions in the polymerase region of the adenovirus genome. Preferably, the deletion(s) prevents, or essentially prevents, the expression of a functional polymerase protein from the deleted region. In a further preferred embodiment, the present invention provides deleted propagation-defective adenoviruses carrying two or more deletions in two or more regions of the adenovirus genome, wherein one of the deleted regions is in the polymerase region. In particular embodiments wherein there are two deleted regions and the first deleted region is a single deletion at nucleotides 7274 to 7881 of the polymerase region, the second deleted region is any other region as described herein with the exception of the E3 region. In more preferred embodiments, the adenovirus has one or more deletions in the polymerase region and one or more deletions in the E1 region, and optionally, one or more deletions in other regions of the adenovirus genome.

In a further alternative preferred embodiment, the present invention provides an infectious, propagation-defective, adenovirus comprising an adenovirus genome containing one or more heterologous nucleotide sequences encoding a lysosomal acid α-glucosidase (GAA), more preferably a human GAA (hGAA), and one or more deletions in one or more of the 100K, IVa2, polymerase and/or preterminal protein regions. The deletion(s) preferably prevents, or essentially prevents, the expression of a functional 100K, IVa2, polymerase and/or preterminal protein, respectively, from the deleted region.

The term "prevents the expression" of a functional protein, as used herein, means that no detectable protein activity is detectable. The defect may be at the level of transcription, translation and/or post-translational processes. Thus, even if there is transcription and translation of the deleted gene(s), the resulting protein has no detectable biological activity. The term "essentially prevents the expression" of a functional adenovirus protein, as used herein, means that only an insignificant amount of biological activity attributable to the protein is detectable. For example, one way of detecting functional protein activity is by monitoring the production of encapsidated adenovirus. In the presence of a deletion that "essentially prevents the expression" of a functional adenovirus protein, only an insignificant amount of new adenovirus particles will be produced in the absence of complementation. Packaging of new virions by the inventive deleted adenoviruses, in the absence of complementing functions, is less than about 10%, 5%, 2%, 1%, 0.05%, or even 0.01% of the levels detected with wild-type adenoviruses or the deleted adenoviruses in the presence of complementing functions.

The inventive deleted adenoviruses cannot propagate (i.e., replicate and package new virus particles) without the provision of complementing functions to compensate for the deletions(s), e.g., transcomplementation by a packaging cell. As described in more detail hereinbelow, the packaging cell will typically express and provide the functional protein that cannot be expressed from the adenovirus genome as a result of the deletion therein. In the presence of transcomplementing functions, the deleted adenovirus vectors of the invention can replicate and package new virions.

The term "deleted" as used herein refers to the omission of at least one nucleotide from the indicated region of the adenovirus genome. Deletions can be greater than about 1, 2, 3, 5, 10, 20, 50, 100, 200, or even 500 nucleotides. Deletions in the various regions of the adenovirus genome may be about at least 1%, 5%, 10%, 25%, 50%, 75%, 90%, 95%, 99%, or more of the indicated region. Alternately, the entire region of the adenovirus genome is deleted. Preferably, the deletion will prevent or essentially prevent the expression of a functional protein from that region. For example, it is preferred that the deletion in the 100K region results in the loss of expression of a functional 100K protein from that region. In other words, even if there is transcription across the deleted 100K region and translation of the resulting RNA transcripts, the resulting protein will be essentially non-functional, more preferably, completely non-functional. Alternatively, an insignificant amount of a function protein is expressed. In general, larger deletions are preferred as these have the additional advantage that they will increase the carrying capacity of the deleted adenovirus for a heterologous nucleotide sequence of interest. The various regions of the adenovirus genome have been mapped and are understood by those skilled in the art (see, e.g., FIELDS et al., VIROLOGY, volume 2, chapters 67 and 68 (3d ed., Lippincott-Raven Publishers).

Preferably, the deletions in the inventive adenoviruses are not temperature-sensitive deletions. In other words, preferably, the loss of replication and packaging effected by the deletion(s) are constitutive mutations and are not temperature-sensitive mutations.

As used herein, a "functional" protein is one that retains at least one biological activity normally associated with that protein. Preferably, a "functional" protein retains all of the activities possessed by the naturally-occurring protein. A "non-functional" protein is one that exhibits no detectable biological activity normally associated with the protein. An "essentially non-functional" protein is one that retains only an insignificant amount of biological activity or, alternatively, only an insignificant amount of functional protein is produced.

Adenovirus vectors containing multiple deletions are preferred to both increase the carrying capacity of the vector and reduce the likelihood of recombination to generate replication competent virus. Those skilled in the art will appreciate that where the adenovirus contains multiple deletions, it is not necessary that each of the deletions, if present alone, would result in a propagation-defective adenovirus as described above. As long as one of the deletions renders the adenovirus propagation-defective, the additional deletions may be included for other purposes, e.g., to increase the carrying capacity of the adenovirus genome for heterologous nucleotide sequences. Preferably, more than one of the deletions prevents the expression of a functional protein and renders the adenovirus propagation-defective. More preferably, all of the deletions are deletions that would render the adenovirus propagation-defective.

It will further be apparent to those skilled in the art that due to the known overlap of coding regions within the adenovirus genome, the deletions described hereinabove may result in the loss of more than one functional adenovirus protein. Likewise, it is not necessary that all functional gene expression from the deleted region be ablated, only the functional expression of the 100K, IVa2, polymerase and/or preterminal protein as indicated. Preferably, the deletions are selected so as not to interfere with other essential functions, e.g., the polymerase deletions are chosen so as not to interfere with the major late promoter sequence or the tripartite leader sequence, and the preterminal protein deletions are chosen so as not to interfere with the VA-RNA sequences.

It will be apparent that other deletions can be combined with the inventive deletions described herein. For example, first-generation adenovirus vectors are typically deleted for the E1 genes and packaged using a cell that expresses the E1 proteins (e.g., 293 cells). The E3 region is also frequently deleted as well, as there is no need for complementation of this deletion. In addition, deletions in the E4, E2a, protein IX, and fiber protein regions have been described, e.g., by Armentano et al, (1997) *J. Virology* 71:2408, Gao et al., (1996) *J. Virology* 70:8934, Dedieu et al., (1997) *J. Virology* 71;4626, Wang et al., (1997) *Gene Therapy* 4:393, U.S. Pat. No. 5,882,877 to Gregory et al. (the disclosures of which are incorporated herein in their entirety). Preferably, the deletions are selected to avoid toxicity to the packaging cell. Wang et al., (1997) *Gene Therapy* 4:393, has described toxicity from constitutive co-expression of the E4 and E1 genes by a packaging cell line. Toxicity may be avoided by regulating expression of the E1 and/or E4 gene products by an inducible, rather than a constitutive, promoter. Combinations of deletions that avoid toxicity or other deleterious effects on the host cell can be routinely selected by those skilled in the art. Those skilled in the art will appreciate that typically, with the exception of the E3 genes, any additional deletions will need to be complemented in order to propagate (replicate and package) additional virus, e.g., by transcomplementation with a packaging cell.

Unlike some other gutted adenovirus vector systems described in the literature (Clemens et al, (1996) *Gene Ther.* 3:965; Hardy et al., (1997) *J. Virol.* 71:1842; Kochanek et al., 1996) *Proc. Natl. Acad. Sci. USA* 93:5731; Kumar-Singh, (1996) *Mol. Gen.* 5:913; Parks et al., (1996) *Proc. Natl. Acad. Sci. USA* 93:13565), the vectors of the present invention do not require any type of helper virus for high-titer growth. In fact, use of the multiply-deleted adenoviruses of the present invention in packaging cells to produce gutted adenovirus vector stocks will reduce the likelihood of any recombination events which produce contaminating replication competent virus in gutted adenovirus vector stocks of prior systems. This is an important problem that may limit the overall usefulness of existing gutted adenovirus preparations (Hardy et al., (1997) *J. Virol.* 71:1842). Further, as described in more detail below, use of the deleted adenoviruses of the present invention as helper viruses may increase the efficacy of transduction with gutted adenovirus vectors which may be dependent on the presence of helper virus contamination for stable gene transduction (Lieber et al., (1997) *J. Virol.* 70:8944; Lieber et al., (1997) *Nature Biotech.* 15:1383).

In particular preferred embodiments, the deleted adenoviruses include deletions in the preterminal protein and the E1 and/or E3 regions. In other preferred embodiments, the adenoviruses contain deletions in the polymerase region and the E1 region. Also preferred are adenoviruses including deletions in the preterminal protein and polymerase regions as well as the E1 and/or E3 regions. In addition, adenoviruses carrying deletions in the 100K and the E1 and/or E3 regions are preferred. Further preferred are deleted adenoviruses containing deletions in the polymerase and IVa2 as well as the E1 and/or E3 regions. Still more preferred are adenoviruses containing deletions in the IVa2, polymerase, preterminal protein, and the E1 and/or E3 regions, as well as adenoviruses carrying deletions in the 100K, polymerase, preterminal protein, and the E1 and/or E3 regions. Yet further preferred are adenoviruses carrying deletions in the IVa2, 100K, polymerase, preterminal protein, and the E1 and/or E3 regions, more preferably still (both the E1 and E3 regions are deleted).

In other particular preferred embodiments, the deletion in the IVa2 region is from about nucleotides 4830 to 5766 of the adenovirus serotype 5 genome, the deletion in the 100K region is from about nucleotide 24,990 to 25,687 of the adenovirus serotype 5 genome, the deletion in the preterminal protein region is from about nucleotides 9198 to 9630 of the adenovirus serotype 5 genome, and the deletion in the polymerase region is from about nucleotide 7274 to 7881 of the adenovirus serotype 5 genome. Adenoviruses that contain deletions in the preterminal protein region at about nucleotides 9198 to 9630 and the polymerase region at about nucleotide 7274 to 7881 of the adenovirus serotype 5 genome are also preferred. Further preferred are polymerase and preterminal protein region deletions that encompass the region from about nucleotide 7274 to 9630 of the adenovirus 5 genome. Those skilled in the art will appreciate that similar deletions can be made in the homologous regions of the adenovirus genomes from other serotypes. In other particular preferred embodiments, the deleted adenoviruses are those disclosed herein as [E1-, E3-, pol-]Ad, [E1-, E3-, pol-, TP-]Ad, [E1-, E3-, IVa2-, pol-, pTP-]Ad, [E1-, 100K-]Ad, or [E1-, E3-, IVa2-, pol-, pTP-, 100K-]Ad.

As described in more detail hereinbelow, any of the inventive adenoviruses described above may additionally contain one or more heterologous nucleotide sequences (e.g., two, three, four, five, six or more sequences) of interest.

Those skilled in the art will appreciate that the inventive adenovirus vectors may additionally contain other mutations. For example, the adenovirus may be modified or "targeted" as described in Douglas et al., (1996) *Nature Biotechnology* 14:1574; U.S. Pat. No. 5,922,315 to Roy et al.; U.S. Pat. No. 5,770,442 to Wickham et al.; and/or U.S. Pat. No. 5,712,136 to Wickham et al. (the disclosures of which are all incorporated herein in their entirety).

II. Reagents and Methods for Producing Deleted Adenovirus.

Except as otherwise indicated, standard methods may be used for the construction of the recombinant adenovirus genomes, helper adenoviruses, and packaging-cells according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

The inventive deleted adenovirus vectors can be generated as described herein or by any other method known in the art. For example, deleted adenoviruses can be generated by co-transfection of a shuttle plasmid containing a deletion (s) of interest (and optionally a heterologous nucleotide sequence) and either a plasmid encoding the remaining sequences of the adenovirus or with virion DNA from a viable adenovirus into an appropriate packaging cell. Co-transfection of the two molecules into the packaging cell followed by a successful recombination event between the two molecules (the shuttle plasmid also contains regions of homology to the adenovirus genome) results in the generation of the full length vector genome, containing the deletions of interest and capable of propagation in the appropriate transcomplementing cell.

According to one particular method a plasmid is created containing a substantial portion of the adenovirus genome which includes the desired new deletion(s) as well as other desired mutations (preferably also deletions). The starting plasmid preferably contains, in addition to mu 0 through 1 of the adenovirus genome, a restriction enzyme site (e.g., an AscI site), and mu 9 through at least mu 40 of the adenovirus genome. Such a starting plasmid may be manipulated using techniques known in the art to contain the desired additional deletions and/or the desired transgene.

The resulting plasmid containing the desired mutations in the adenovirus genome portion of the plasmid and/or the desired transgene is then linearized by digesting with a restriction endonuclease, such as EcoRI, BspHI, NheI, or AseI. The linearized plasmid DNA containing the desired transgene and/or deletion is cotransfected with adenoviral DNA, which has been prepared as described below, into a packaging cell line capable of supporting (transcomplementing) a productive infection of adenovirus with the desired deletion(s).

The adenovirus genomic DNA used in cotransfection can be isolated as intact virion DNA-terminal protein complex as described in Jones et al., (1978) *Cell* 13:181. The genomic DNA may be from a virus which already contains desired mutations, preferably deletions, such as in the E1, E3, pol, pTP, IVa2, and/or 100K regions. Prior to its use in cotransfection, adenovirus genomic DNA is first digested with at least two restriction enzymes. These enzymes are selected to cause a significant number of double stranded breaks in the adenoviral genome in the area of the chromosome for which no recombination events are desired. Preferably, the area where no recombination events are desired includes at least nucleotide 1 through at nucleotide 10590, allowing recombination events to occur, for example, between nucleotide 10590 and nucleotide 15671 in pAdAscL-Δpol (Example 2).

Use of a shuttle plasmid containing a larger portion of the adenovirus genome such as that present in one of the preferred shuttles of the present invention, pAdAscL-Δpol (Example 2), promotes recombination in this more distal region of the adenoviral genome. Further, by first digesting the genomic adenoviral DNA using multiple restriction enzymes, preferably ClaI, XbaI, and ScaI, one achieves a significant reduction in the ability of the genomic adenoviral DNA to generate a viable, non-recombinant virus. This is due to the fact that the portion of the viral DNA required for such recombination is more likely to be restriction enzyme digested multiple times. The utilization of several restriction enzymes therefore essentially prevents the generation of undesirable, non-recombinant virus derived from the digested virion DNA.

The preferred shuttling plasmid is pAdAscL-Δpol (Example 2). This plasmid is similar to pAdAscl, a plasmid known to the prior art, however pAdAsci contains only map units 9 through 16 of the adenovirus genome while pAdAscL-wt contains map units 9 through 43. The additional Ad sequences present in pAdAscL-wt allows one to digest virion DNA with multiple restriction enzymes prior to cotransfection with the linearized shuttle plasmid during initial vector construction, thereby reducing creation by recombination of undesirable recombinant viruses.

The genomic DNA can preferably be isolated from an adenovirus strain which contains at least the E1 deletion as well as, optionally, other desired, previously created deletions to further reduce the possibility of generating adenovirus without the desired genetic attributes.

Thus, the manipulated plasmid DNA, containing the desired transgene and/or mutation, is linearized (i.e. with BspHI, EcoRI, or NheI), co-transfected with the multiply-digested virus genome, preferably the Ad5 adenovirus E1-strain dl7001 as described in Example 1 below, into a packaging cell line which expresses any required adenovirus gene functions. After incubating for a time sufficient to allow for viral growth, the transfected cells are harvested and mixed with non-transfected packaging cells. This cell mixture is distributed to tissue culture cluster plates and, after incubation, the individual wells of these plates which demonstrate viral cytopathic effect (CPE) are harvested. Each well represents a single clonal isolate of virus. The clonal isolates are then characterized as described elsewhere herein. For example, DNA restriction mapping, functional studies, $^{32}$P probes and similar studies are performed to confirm and characterize the genotype of the recombinant vector/virus.

The present invention further provides reagents (e.g., isolated nucleotide sequences, vectors, cells) and methods for producing the inventive deleted adenoviruses.

Further disclosed herein are isolated nucleotide sequences, more preferably DNA sequences, encoding a deleted adenovirus 100K protein. The nucleotide sequence encoding the 100K protein contains one or more deletions (as described for deleted adenovirus vectors hereinabove) such that the deletions(s) essentially prevents the expression of a functional 100K protein from the deleted nucleotide sequence (as described hereinabove). Preferably, the nucleotide sequence is contained within an adenovirus genome, more preferably a recombinant adenovirus genome. Also provided by the present invention are vectors (e.g., a plasmid vector) carrying the adenovirus genome containing the deleted 100K region. An illustrative plasmid according to the present invention is the plasmid disclosed herein as pcDNA3+100K. Further provided are cells containing the inventive vectors, including bacterial, protozoan, yeast, fungus, plant and animal (e.g., insect, avian and mammalian) cells.

Figure 19:
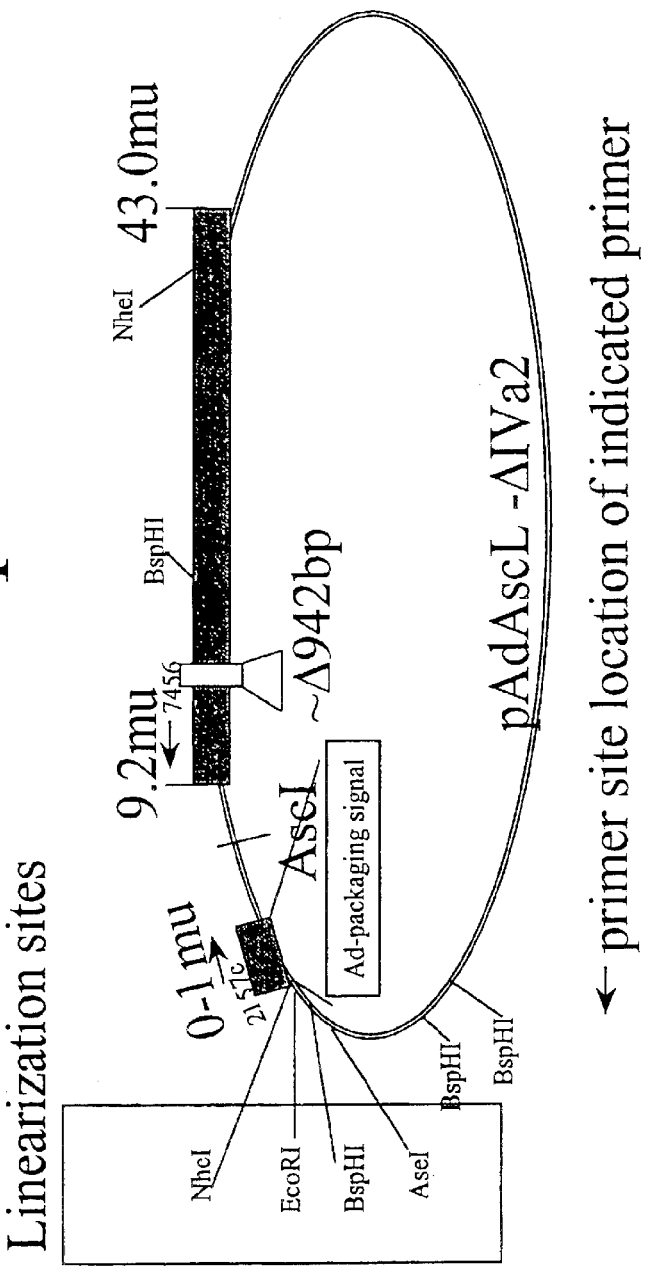
FIG. 19 shows the structure of shuttle plasmid pAdAscL-ΔIVa2.
Figure 37:
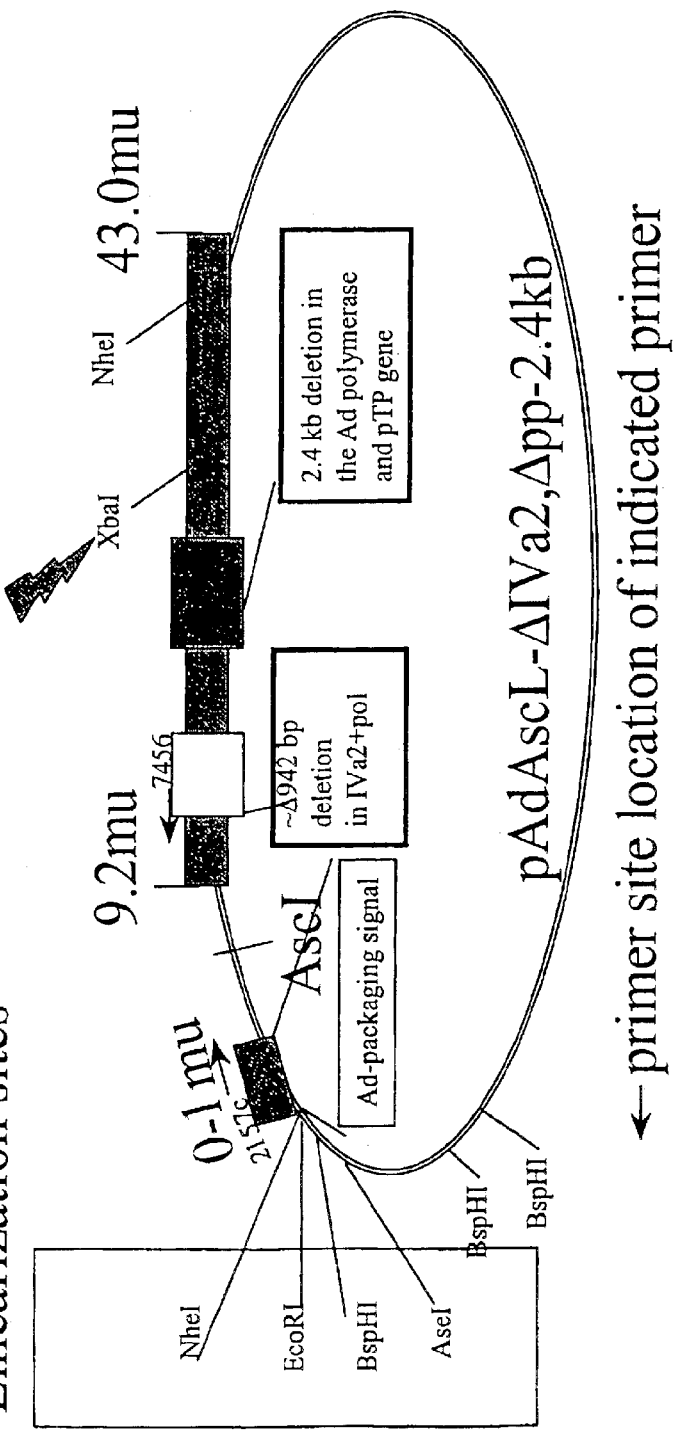
FIG. 37 shows the structure of shuttle plasmid pAdAscL-ΔIVa2, Δpp-2.4 kb.
Figure 38:
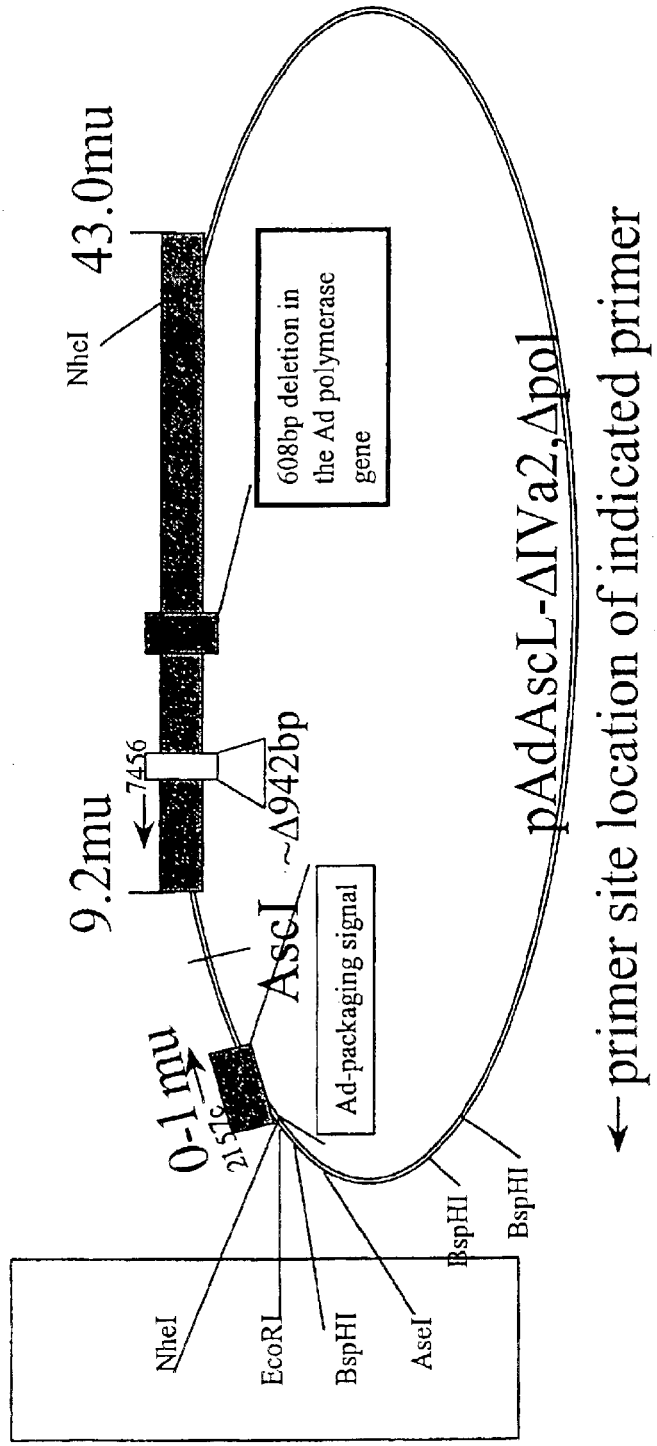
FIG. 38 shows the structure of shuttle plasmid pAdAscL-ΔIVa2, Δpol.

Also provided are isolated nucleotide sequences (preferably, DNA sequences), adenovirus genomes, and vectors encoding an adenovirus IVa2 protein containing one or more deletions (as described hereinabove for deleted adenovirus vectors) and cells containing the same. These reagents are otherwise the same as those described for the 100K protein in the preceding section. Exemplary plasmids encoding a deleted IVa2 gene include those described herein as pAdAscLΔIVa2 (FIG. 19; deletion of about 942 bp at about nucleotides 4830 to 5766 of the Ad5 genome in addition to deleted E1 and E3 regions), pAdAscLΔIVa2, Δpol (FIG. 38; deletion of about 942 bp at about nucleotides 4830 to 5766 and a deletion of about 608 bp at about nucleotides 7274 to 7881 of the Ad5 genome in addition to deleted E1 and E3 regions), pAdAscLΔIVa2, Δpp (1.6) (FIG. 36; deletion of about 942 bp at about nucleotides 4830 to 5766, a deletion of about 608 bp at about nucleotides 7274 to 7881, and a deletion of about 955 bp at about nucleotides 8631 to 9585 of the Ad5 genome in addition to deleted E1 and E3 regions), and pAdAscLΔIVa2, Δpp (2.4) (FIG. 37; deletion of about 942 bp at about nucleotides 4830 to 5766, a deletion of about 608 bp at about nucleotides 7274 to 7881, and a deletion of about 2312 bp at about nucleotides 7274 to 9585 of the Ad5 genome in addition to deleted E1 and E3 regions).

The present invention further encompasses cells for packaging the inventive deleted adenoviruses. Accordingly, in one particular embodiment, the present invention provides a cell containing an isolated nucleotide sequence encoding a functional (as described hereinabove) adenovirus 100K protein. The cell may be a bacterial, protozoan, yeast, fungus, plant or animal cell.

Preferably, the cell is an animal cell (e.g. an insect, avian or mammalian cell), more preferably a mammalian cell. The nucleotide sequence can be present in the cell extrachromosomally or, preferably, may be stably integrated into the genome of the cell. Typically, the isolated nucleotide sequence encoding the functional 100K protein is operatively associated with appropriate expression control sequences (e.g., a promoter sequence). Expression of the nucleotide sequence can be constitutive or inducible.

In particular preferred embodiments, the cell expressing the functional 100K protein can transcomplement a 100K deleted adenovirus genome (as described hereinabove). In other words, a propagation-defective 100K deleted adenovirus can be replicated and packaged in the cell expressing the functional 100K protein. In preferred embodiments, the cell is a K-16 cell or a C7 cell constitutively expressing the adenovirus 100K protein, each as disclosed herein.

Those skilled in the art will appreciate that the deleted adenovirus genome may contain additional deletions in addition to the 100K deletion. Typically, with the exception of the E3 region, it will be necessary to transcomplement these deletions in order to package new virus particles. Transcomplementation can be achieved by any means known in the art, e.g., by the packaging cell or with a helper adenovirus. As a further alternative, the missing function may be transiently transfected into the packaging cell that normally does not express this function. Preferably, the inventive adenoviruses are produced with a transcomplementing packaging cell.

In another particular embodiment, the present invention provides a cell containing an isolated nucleotide sequence encoding a functional (i.e., biologically active) adenovirus IVa2 protein. Cells containing the isolated nucleotide sequence encoding the functional IVa2 protein are as described above for cells expressing a functional 100K protein. Exemplary cells expressing a functional IVa2 protein include those disclosed herein as a B6 or C7 cell.

The present invention also encompasses methods of producing the deleted adenovirus particles of the present invention. According to one particular method a deleted adenovirus is introduced into a transcomplementing packaging cell (as described above). The adenovirus genome contains one or more deletions in one or more of the adenovirus 100K, IVa2 and/or preterminal protein regions (as described in detail for deleted adenovirus vectors hereinabove). Methods of transducing cells with adenoviruses are well-known by those skilled in the art. The deleted adenovirus is replicated and packaged in the transcomplementing cell (i.e., expressing the deleted function(s)), and the deleted adenovirus particles are collected. The packaging cell is preferably an animal cell (e.g., insect, avian, mammalian), more preferably, a mammalian cell.

In an alternate embodiment, the present invention provides a method of producing a deleted adenovirus that contains one or more deletions in the E1 region and one or more deletions in the polymerase region (as described hereinabove for deleted adenoviruses). The deleted adenovirus can replicated and packaged in a transcomplementing cell expressing the deleted adenovirus functions the new virions collected.

In another preferred embodiment, the present invention provides a method for producing a deleted adenovirus containing two or more deletions in two or more regions of the adenovirus genome, wherein one of the deleted regions is in the polymerase region. In particular embodiments wherein there are two deleted regions, the first deleted region is the polymerase region and the second deleted region is any other region as described herein, with the exception of the E3 region. In more preferred embodiments, the adenovirus has one or more deletions in the polymerase region and one or more deletions in the E1 region, and optionally, one or more deletions in other regions of the adenovirus genome. The deleted adenovirus can replicated and packaged in a transcomplementing cell expressing the deleted adenovirus functions the new virions collected.

As a further non-limiting alternative, the present invention provides a method of producing a deleted adenovirus carrying a nucleotide sequence encoding a GAA protein and further containing one or more deletions in one or more of the 100K, IVa2, preterminal protein, and polymerase regions. The deleted adenovirus can replicated and packaged in a transcomplementing cell expressing the deleted adenovirus functions the new virions collected.

PCT Publication WO 98/17783 to Chamberlain et al. describes packaging of adenovirus vectors containing deletions in the polymerase and/or preterminal protein regions. However, as described herein and by Amalfitano et al., (1998) *J. Virology* 72:926 (page 928, first full paragraph of Methods & Materials), the methods described in this reference based on the pBHG11 plasmid failed to produce adenoviruses deleted in the polymerase and/or preterminal protein regions.

In contrast, according to the inventive packaging methods described herein, the collected adenovirus preferably has a titer of at least 100 infectious units per cell, more preferably at least 1000 infectious units per cell, more preferably still at least 10,000 infectious units per cell. The present inventors have successfully used the inventive methods described herein to produce high titer stocks of adenoviruses carrying deletions in the E1, E3, 100K, IVa2, preterminal protein and/or polymerase regions.

The present invention further encompasses methods of producing the inventive adenovirus vectors using bacterial cells. For example, He et al. (1998) *Proc. Natl. Acad. Sci. USA* 95:2509 describe a method for producing deleted adenovirus using an adenoviral plasmid (see also, U.S. Pat. No. 5,922,576 to He et al., the disclosure of which is incorporated herein in its entirety). Accordingly, in one particular embodiment, the present invention provides a method of producing an infectious deleted adenovirus of the present invention by introducing a bacterial plasmid carrying an adenovirus genome into a bacterial cell. The adenovirus genome comprises one or more deletions in one or more of the polymerase, preterminal protein, 100K, and/or IVa2 regions (as described hereinabove for deleted adenoviruses). The bacterial plasmid is amplified in the bacterial cell, recovered, and linearized. The linearized plasmid carrying the deleted adenovirus genome is introduced into a transcomplementing packaging cell (as described hereinabove) where it is replicated and packaged into new virions. The adenovirus particles are collected. Preferably, the adenovirus genome further encodes one or more heterologous nucleotide sequences.

The present invention further provides a method for producing a gutted adenovirus vector containing an adenovirus minichromosome. Adenovirus minichromosomes are as described by WO 98/17783 to Chamberlain et al. and Kumar-Singh et al., (1996) *Human Molecular Genetics* 5:913. The deleted adenoviruses of the present invention can be used as an optimized helper virus for the growth of gutted adenoviruses. A method for growing high titer stocks of a gutted adenovirus vectors using the deleted viruses of the present invention involves co-infecting gutted adenovirus vectors and a propagation-defective deleted adenovirus of the present invention into a packaging cell that is permissive for the growth of the deleted vector, then harvesting the resulting virus particles.

According to one particular and preferred method, a plasmid containing at least one adenovirus ITR (preferably two ITRs), an adenovirus packaging sequence, and one or more heterologous nucleotide sequences of interest are introduced into a packaging cell. A helper adenovirus comprising an adenovirus genome containing one or more deletions in the 100K region is also introduced into the packaging cell. The 100K deleted vector may also contain additional deletions in other regions, as described above. The packaging cell expresses a functional 100K protein and transcomplements the deletion in the 100K region of the adenovirus genome. The packaging cell and 100K deleted adenovirus genome are each as described hereinabove. The adenovirus minichromosome can be replicated and packaged in the presence of the helper adenovirus and transcomplementing cell line, and the gutted adenovirus vectors containing the adenovirus minichromosome are collected.

If desired, the gutted vector may be separated from the deleted adenovirus by any method known in the art, e.g., cesium chloride centrifugation or any other density gradient. In addition to use of prior art separation techniques, one can reduce the helper virus contamination by preventing packaging of the helper virus. For example, the adenovirus genome carried by the helper adenovirus may lack an adenovirus packaging sequence to prevent packaging of the helper adenovirus genome. Alternatively, the helper adenovirus carries a modified packaging sequence that does not enable encapsidation of the helper adenovirus genome.

As a further non-limiting alternative, the helper adenovirus genome has lox sites flanking the packaging sequence and the packaging cell produces the Cre recombinase protein. The presence of the Cre recombinase results in lox mediated recombination and removal of all sequences flanked by the lox sites (e.g., the packaging signal and/or other adenovirus sequences) and prevents the lox-containing DNA from being packaged (Parks et al., (1996) *Proc. Natl. Acad. Sci. USA* 93:13565). In a variation of this methodology the lox sites are placed within the multiply deleted vector flanking a greater amount of the Ad genome. When placed into Cre cells a large portion of the deleted vector genome is removed. The resulting reduced helper virus is purified away from the unloxed vector via cesium chloride centrifugation or other methods known in the art (Lieber et al., (1996) *J. Virol.* 70:8944; Kochanek et al., (1996) *Proc. Natl. Acad. Sci. USA* 93:5731).

Also provided herein are methods of producing a gutted adenovirus carrying a minichromosome with a helper adenovirus containing an adenovirus genome comprising one or more deletions in the IVa2 region and a packaging cell that transcomplements this deletion by expressing a functional IVa2 protein. These methods are otherwise similar to those described above for packaging a gutted adenovirus using a helper adenovirus containing a deleted 100K region.

Further provided herein are methods of producing a gutted adenovirus carrying a minichromosome with a helper adenovirus containing an adenovirus genome comprising one or more deletions in the polymerase and/or preterminal protein regions and a packaging cell that transcomplements this deletion(s) by expressing a functional preterminal protein and/or polymerase, respectively. Preterminal protein and polymerase deletions are as described above for deleted adenovirus vectors. These methods are otherwise similar to those described above for packaging a gutted adenovirus using a helper adenovirus containing a deleted 100K region.

The deleted adenoviruses of the present invention can also be used in gene therapy methods using gutted adenovirus vectors to assist in stabilizing the gutted vector genomes in the target cells by co-infecting the target cells with deleted viruses of the present invention along with the gutted vector. Destabilization of gutted adenovirus vectors due to lack of helper virus contamination (and trans-acting activities) has recently been described as a potentially severe limitation of gutted Ad vector preparations (Lieber et al., (1996) *J. Virol.* 70:8944). Contamination of the gutted adenovirus stock with the deleted vectors described herein is preferable to first-generation E1 deleted helpers, which have been reported to be "leaky" when introduced into cells or subjects. Preferably, according to this embodiment, the contaminating helper adenovirus is a multiply-deleted adenovirus, so as to minimize the likelihood of recombination to generate replication competent vector and/or any "leakiness" in gene expression.

Accordingly, the present invention provides a composition (preferably, a pharmaceutical composition) comprising a gutted adenovirus containing a minichromosome and a deleted helper adenovirus according to the present invention. The abundance of the deleted helper adenovirus is preferably less than about 50%, 30%, 20%, 10%, 5%, 2.5%, 1%, 0.05%, 0.01%, 0.001% or lower than the abundance of the gutted adenovirus in the composition. These compositions can be advantageously administered to a subject according to any of the methods described herein to combine the advantages of a gutted adenovirus vector with the stabilizing effect of the deleted helper adenovirus.

III. Recombinant Adenovirus Vectors.

As used herein, a "recombinant adenovirus vector" is an adenovirus vector that carries one or more heterologous nucleotide sequences or transgenes (e.g., two, three, four, five or more heterologous nucleotide sequences or transgenes). The deleted adenovirus vectors of the present invention are useful for the delivery of nucleic acids to cells both in vitro and in vivo. In particular, the inventive vectors can be advantageously employed to deliver or transfer nucleic acids to animal, more preferably mammalian, cells. Nucleic acids of interest include nucleic acids encoding peptides and proteins, preferably therapeutic (e.g., for medical or veterinary uses) or immunogenic (e.g., for vaccines) peptides or proteins.

Alternatively, in particular embodiments of the invention, the nucleic acid of interest may encode an antisense nucleic acid, a ribozyme, or other non-translated RNAs, such as "guide" RNAs (Gorman et al., (1998) *Proc. Nat. Acad. Sci. USA* 95:4929), and the like.

The present invention also provides vectors useful as vaccines. The antigen can be presented in the adenovirus capsid, alternatively, the antigen can be expressed from a heterologous nucleic acid introduced into a recombinant adenovirus genome and carried by the inventive adenoviruses. Any immunogen of interest can be provided by the adenovirus vector. Immunogens of interest are well-known in the art and include, but are not limited to, immunogens from human immunodeficiency virus (e.g., envelope proteins), influenza virus, gag proteins, cancer antigens, HBV surface antigen (to immunize against hepatitis), rabies glycoproteins, and the like.

As a further alternative, the adenovirus vectors can be used to infect a cell in culture to express a desired gene product, e.g., to produce a protein or peptide of interest (for example, lysosomal acid α-glucosidase). Preferably, the protein or peptide is secreted into the medium and can be purified therefrom using routine techniques known in the art. Signal peptide sequences that direct extracellular secretion of proteins are known in the art and nucleotide sequences encoding the same can be operably linked to the nucleotide sequence encoding the peptide or protein of interest by routine techniques known in the art. Alternatively, the cells can be lysed and the expressed recombinant protein can be purified from the cell lysate. The cell may be a bacterial, protozoan, plant, yeast, fungus, or animal cell. Preferably, the cell is an animal cell (e.g., insect, avian or mammalian), more preferably a mammalian cell. Also preferred are cells that are competent for transduction by adenoviruses.

The size of the adenovirus vector can vary. Generally, the adenovirus genome is most stable at sizes of about 28 kb to 38 kb. (approximately 75% to 105% of the native genome size). In the case of an adenovirus vector containing large deletions and a relatively small transgene, "stuffer DNA" can be used to maintain the total size of the vector within the desired range by methods known in the art. The deleted vectors of the present invention can advantageously be used to deliver transgenes of up to about 9, 11 or even 12.5 kb in size or more.

Those skilled in the art will appreciate that the heterologous nucleotide sequence(s) are preferably operably associated with the appropriate expression control sequences. For example, the recombinant adenovirus vectors of the invention preferably contain appropriate transcription/translation control signals and polyadenylation signals operably associated with the heterologous nucleic acid sequence(s) to be delivered to the target cell. Those skilled in the art will appreciate that a variety of promoter/enhancer elements may be used depending on the level and tissue-specific expression desired. The promoter can be constitutive or inducible (e.g., the metallothionine promoter), depending on the pattern of expression desired. The promoter may be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest. Brain-specific, hepatic-specific, and muscle-specific (including skeletal, cardiac, smooth, and/or diaphragm-specific) promoters are more preferred. Mammalian promoters are also preferred.

More preferably, the heterologous nucleotide sequence(s) are operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter. It has been speculated that driving heterologous nucleotide transcription with the CMV promoter results in down-regulation of expression in immunocompetent animals (see, e.g., Guo et al., (1996) *Gene Therapy* 3:802). Accordingly, it is also preferred to operably associate the heterologous nucleotide sequencers) with a modified CMV promoter that does not result in this down-regulation of transgene expression.

In embodiments wherein there is more than one heterologous nucleotide sequence, those skilled in the art will appreciate that the heterologous nucleotide sequences may be operatively associated with a single upstream promoter and one or more downstream internal ribosome entry site (IRES) sequences (e.g., the picornavirus EMC IRES sequence).

Also preferred are embodiments wherein the adenovirus genome contains at least one adenovirus inverted terminal repeat (ITR) sequence, more preferably two adenovirus ITR sequences. Moreover, it is also preferred that the recombinant adenovirus genome carrying the transgene also encodes an adenovirus packaging sequence. For example, in one particular embodiment, the adenovirus genome comprises one or more heterologous nucleotide sequences, the 5' and 3' adenovirus ITRs, the adenovirus packaging sequence, and an adenovirus E1A enhancer sequence.

In embodiments of the invention in which the heterologous nucleotide sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

Heterologous nucleotide sequences encoding proteins and peptides include those encoding reporter proteins (e.g., an enzyme). Reporter proteins are known in the art and include, but are not limited to, Green Fluorescent Protein, β-galactosidase, alkaline phosphatase, and chloramphenicol acetyltransferase gene. More preferably, the adenovirus vector is the vector disclosed herein as AdLacZΔpol or AdLacZΔpp.

Therapeutic peptides and proteins include, but are not limited to, cystic fibrosis transmembrane regulator protein (CFTR), dystrophin (including the protein product of dystrophin mini-genes, see, e.g, Vincent et al., (1993) *Nature Genetics* 5:130), utrophin (Tinsley et al., (1996) *Nature* 384:349), clotting factors (e.g., Factor XII, Factor IX, Factor X, etc.), erythropoietin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, hormones, growth factors, cytokines (e.g., interferon-γ, interleukin-2, interleukin-4, granulocyte-macrophage colony stimulating factor), suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), and any other peptide or protein that has a therapeutic effect in a subject in need thereof.

In particular preferred embodiments of the invention, the heterologous nucleotide sequence encodes a protein or peptide that is associated with a metabolic disorder. By "associated with a metabolic disorder", it is intended that the expressed protein or peptide is one that is deficient or defective in a metabolic disorder, or is otherwise a causative agent in a metabolic disorder.

In other particular preferred embodiments, the protein or peptide is a lysosomal protein or peptide, more preferably a precursor protein or peptide that retains the mannose-6-phosphate residues that are characteristic of proteins targeted to the lysosomal compartment.

In still further preferred embodiments, the heterologous nucleotide sequence encodes a peptide or protein that is associated with a lysosomal storage disease. By "associated with a lysosomal storage disease", it is intended that the expressed protein or peptide is one that is deficient or defective in a lysosomal storage disorder, or is otherwise a causative agent in a lysosomal storage disorder.

There are a multitude of lysosomal storage diseases, as is well-known in the art. Exemplary lysosomal storage disease include, but are not limited to, GM1 gangliosidosis, Tay-Sachs disease, GM2 gangliosidosis (AB variant), Sandhoff disease, Fabry disease, Gaucher disease, metachromatic leukodystrophy, Krabbe disease, Niemann-Pick disease (Types A–D), Farber disease, Wolman disease, Hurler Syndrome (MPS IH), Scheie Syndrome (MPS IS), Hurler-Scheie Syndrome (MPS IH/S), Hunter Syndrome (MPS II), Sanfilippo A Syndrome (MPS IIIA), Sanfilippo B Syndrome (MPS IIIB), Sanfilippo C Syndrome (MPS IIIC), Sanfilippo D Syndrome (MPS IIID), Morquio A disease (MPS IVA), Morquio B disease (MPS IV B), Maroteaux-Imay disease (MPS VI), Sly Syndrome (MPS VII), α-mannosidosis, β-mannosidosis, fucosidosis, aspartylglucosaminuria, sialidosis (mucolipidosis I), galactosialidosis (Goldberg Syndrome), Schindler disease, mucolipidosis II (I-Cell disease), mucolipidosis III (pseudo-Hurler polydystrophy), cystinosis, Salla disease, infantile sialic acid storage disease, Batten disease juvenile neuronal ceroid lipofuscinosis), infantile neuronal ceroid lipofuscinosis, mucolipidosis IV, and prosaposin.

Proteins or peptides that are associated with lysosomal storage diseases according to the present invention include, but are not limited to, β-galactosidase, β-hexosaminidase A, β-hexosaminidase B, $GM_2$ activator protein, glucocerebrosidase, arylsulfatase A, galactosylceramidase, acid sphingomyelinase, acid ceramidase, acid lipase, α-L-iduronidase, iduronate sulfatase, heparan N-sulfatase, α-N-acetylglucosaminidase acetyl-CoA, glucosaminide acetyltransferase, N-acetylglucosamine-6-sulfatase, arylsulfatase B, β-glucuronidase, α-mannosidase, β-mannosidase, α-L-fucosidase, N-aspartyl-β-glucosaminidase, α-neuraminidase, lysosomal protective protein, α-N-acetylgalactosaminidase, N-acetylglucosamine-1-phosphotransferase, cystine transport protein, sialic acid transport protein, the CLN3 gene product, palmitoyl-protein thioesterase, saposin A, saposin B, saposin C, and saposin D.

The present invention further provides deleted recombinant adenovirus vectors carrying a transgene encoding a protein or peptide associated with a glycogen storage disease. By "associated with a glycogen storage disease", it is intended that the expressed protein or peptide is one that is deficient or defective in a glycogen storage disease, or is otherwise a causative agent in a lysosomal storage disease.

There are a multitude of glycogen storage diseases (GSD), as is well-known in the art. Exemplary glycogen storage diseases include, but are not limited to, Type Ia GSD (von Gierke disease), Type Ib GSD, Type Ic GSD, Type Id GSD, Type II GSD (including Pompe disease or infantile Type II GSD), Type IIIa GSD, Type IIIb GSD, Type IV GSD, Type V GSD (McArdle disease), Type VI GSD, Type VII GSD, glycogen synthase deficiency, hepatic glycogenosis with renal Fanconi syndrome, phosphoglucoisomerase deficiency, muscle phosphoglycerate kinase deficiency, phosphoglycerate mutase deficiency, and lactate dehydrogenase deficiency.

Proteins or peptides that are associated with glycogen storage diseases according to the present invention include, but are not limited to, glucose 6-phosphatase, lysosomal acid α glucosidase, glycogen debranching enzyme, branching enzyme, muscle phosphorylase, liver phosphorylase, phosphorylase kinase, muscle phosphofructokinase, glycogen synthase, phosphoglucoisomerase, muscle phosphoglycerate kinase, phosphoglycerate mutase, and lactate dehydrogenase.

In more preferred embodiments, the deleted recombinant adenovirus vector carries a transgene encoding a lysosomal acid α-glucosidase (GAA), e.g., to treat Type II GSD including infantile (Pompe disease), juvenile and adult onset forms of the disease. More preferably, the lysosomal acid α-glucosidase is a human lysosomal acid α-glucosidase (hGAA). The transgene may encode either the mature GAA protein (e.g., the 76 kD form) or a GAA precursor (e.g., the 110 kD form). Preferably, the transgene encodes a GAA precursor. The term "GAA" as used herein encompasses mature and precursor GAA proteins as well as modified (e.g., truncated or mutated) GAA proteins that retain biological function (i.e., have at least one biological activity of the native GAA protein, e.g., can hydrolyze glycogen).

Lysosomal acid α-glucosidase (E.C. 3.2.1.20) (1,4-α-D-glucan glucohydrolase), is an exo-1,4-α-D-glucosidase that hydrolyses both α-1,4 and α-1,6 linkages of oligosaccharides liberating glucose. It catalyzes the complete degradation of glycogen with slowing at branching points. The 28 kb acid α-glucosidase gene on chromosome 17 encodes a 3.6 kb mRNA which produces a 951 amino acid polypeptide (Hoefsloot et al, (1988) *EMBO J.* 7:1697; Martiniuk et al., (1990) *DNA and Cell Biology* 9:85). The nucleotide sequence of a cDNA coding for the polypeptide, as well as the deduced amino acid sequence is provided in Hoefsloot et al. (Id.). The first 27 amino acids of the polypeptide are typical of a leader sequence of a signal peptide of lysosomal and secretory proteins. The enzyme receives co-translational N-linked glycosylation on the endoplasmic reticulum. It is synthesized as a 110-kDa precursor form, which matures by extensive modification of its glycosylation, and phosphorylation and by proteolytic processing through an approximately 90-kDa endosomal intermediate into the final lysosomal 76 and 67 kDa forms (Hoefsloot, (1988) *EMBO J.* 7:1697; Hoefsloot et al., (1990) *Biochem. J.* 272:485; Wisselaar et al., (1 993)*J. Biol. Chem.* 268:2223; Hermans et al., (1993) *Biochem. J.* 289:681).

The human GAA gene as described by Hoefsloot et al., (1988) *EMBO J.* 7:1697 and Van Hove et al., (1996) *Proc. Natl. Acad. Sci. USA* 93:65, includes 5' untranslated sequences. In particular preferred embodiments, the hGAA transgene includes the entire approximately 3.8 kb sequence described by Van Hove et al. Alternatively, the deleted adenoviruses of the present invention may encode more or less of the 5' and 3' untranslated regions of the GAA gene. In other preferred embodiments, the heterologous nucleotide sequence is the approximately 3.3 kb nucleotide sequence encoding the full-length GAA precursor but lacking essentially all of the 5' and 3' sequences (see, e.g., Example 23, the h5'sGAA sequence) or the 3.8 kb GAA sequence from pcDNA-GAA (Example 23) containing additional 5' untranslated sequences.

Also preferred are the adenovirus vectors disclosed herein as AdhGAAΔpol (3.8 kb), Ad/EF1-α/hGAAΔpol (3.8 kb), AdhGAAΔpp (3.8 kb), Ad/EF1-α/hGAAΔpp (3.8 kb), Adh5'sGAAΔpol (3.3 kb), Ad/EF1-α/h5'sGAAΔpol (3.3 kb), AdhGAAΔpp (3.3 kb), and Ad/EF1-α/h5'sGAAΔpp (3.3 kb).

IV. Gene Transfer Technology.

The methods of the present invention provide a means for delivering heterologous nucleotide sequences into a broad range of host cells, including both dividing and non-dividing cells in vitro or in vivo. The vectors, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

In general, the present invention can be employed to deliver any foreign nucleotide sequence to treat or ameliorate the symptoms associated with any disorder related to gene expression. Illustrative disease states include: lysosomal storage diseases, glycogen storage diseases, hemophilias (e.g., hemophilia A and hemophilia B) and other clotting disorders, Gaucher's Disease, diabetes mellitus, cystic fibrosis (and other diseases of the lung), muscular dystrophies (e.g., Duchenne, Becker), diseases of the nervous system (e.g., Alzheimer's Disease, Parkinson's Disease, amyotrophic lateral sclerosis, epilepsy), retinal degenerative diseases (and other diseases of the eye), diseases of solid organs (e.g., brain, liver, kidney, heart), and any other diseases having an infectious or genetic basis.

The instant invention can also be employed to provide an antisense nucleic acid to a cell in vitro or in vivo. Expression of the antisense nucleic acid in the target cell diminishes expression of a particular protein by the cell. Accordingly, antisense nucleic acids can be administered to decrease expression of a particular protein in a subject in need thereof. Antisense nucleic acids can also be administered to cells in vitro to regulate cell physiology, e.g., to optimize cell or tissue culture systems. The present invention is also useful to deliver other non-translated RNAs, e.g., ribozymes or "guide" RNAs (see, e.g., Gorman et al., (1998) *Proc. Nat. Acad. Sci. USA* 95:4929) to a target cell.

Finally, the instant invention finds further use in diagnostic and screening methods, whereby a gene of interest is transiently or stably expressed in a cell culture system.

V. Subjects, Pharmaceutical Formulations, Vaccine and Modes of Administration.

The present invention finds use in veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include neonates, infants, juveniles, and adults.

In particular embodiments, the present invention provides a pharmaceutical composition comprising a virus particle of the invention in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

By "pharmaceutically acceptable" it is meant a material that is not biologically or otherwise undesirable, i.e., the material may be administered to a subject along with the viral vector without causing any undesirable biological effects. Thus, such a pharmaceutical composition can be used, for example, in transfection of a cell ex vivo or in administering a viral particle directly to a subject.

Vaccines of the present invention comprise an immunogenic amount of infectious virus particles as disclosed herein in combination with a pharmaceutically-acceptable carrier. An "immunogenic amount" is an amount of the infectious virus particles that is sufficient to evoke an immune response in the subject to which the pharmaceutical formulation is administered. An amount of from about $10^3$ to about $10^7$ virus particles, and preferably about $10^4$ to $10^6$ virus particles per dose is suitable, depending upon the age and species of the subject being treated, and the immunogen against which the immune response is desired. Subjects and immunogens are as described above.

The present invention further provides a method of delivering a nucleotide sequence into a cell. For in vitro methods, the virus can be administered to the cell by standard viral transduction methods, as, are known in the art. Preferably, the virus particles are added to the cells at the appropriate multiplicity of infection according to standard transduction methods appropriate for the particular target cells. Titers of virus to administer can vary, depending upon the target cell type and the particular virus vector, and can be determined by those of skill in the art without undue experimentation. Preferably, at least about 1000 infectious units, more preferably at least about 10,000 infectious units, are administered to the cell. Alternatively, administration of an adenovirus vector of the present invention can be accomplished by any other means known in the art, as described hereinbelow.

In one preferred embodiment, the present invention provides a method of delivering a heterologous nucleotide sequence into a cell in vitro or in vivo. According to this method a cell is infected with at least one deleted adenovirus vector according to the present invention (as described in detail hereinabove). The cell may be infected with the adenovirus vector by the natural process of viral transduction. Alternatively, the vector may be introduced into the cell by any other method known in the art. For example, the cell may be contacted with a targeted adenovirus vector (as described below) and taken up by an alternate mechanism, e.g., by receptor-mediated endocytosis. As another example the vector may be targeted to an internalizing cell-surface protein using an antibody or other binding protein.

The cell to be administered the inventive virus vectors can be of any type, including but not limited to neuronal cells (including cells of the peripheral and central nervous systems), retinal cells, epithelial cells (including dermal, gut, respiratory, bladder and breast tissue epithelium), muscle cells (including cardiac, smooth muscle, skeletal muscle, and diaphragm muscle), pancreatic cells (including islet cells), hepatic cells (e.g., parenchyma), fibroblasts, endothelial cells, germ cells, lung cells (including bronchial cells and alveolar cells), prostate cells, and the like. Moreover, the cells can be from any species of origin, as indicated above. Preferred are cells that are naturally transduced by adenoviruses.

The adenovirus vectors of the invention may be employed to produced proteins or peptides of interest by cells in vitro. The adenovirus encodes a heterologous nucleotide sequencers) that may encode any protein or peptide of interest, as described hereinabove. The nucleotide sequence preferably encodes a therapeutic protein or peptide. In more preferred embodiments, the heterologous nucleotide sequence encodes a GAA, more preferably hGAA, which may be isolated from the cells using standard techniques and administered to subjects with GAA deficiency using enzyme replacement protocols (see, e.g., Van der Ploeg et al., (1991) *J. Clin. Invest.* 87:513).

Alternatively, adenovirus vectors can be targeted to cells, including cells that are not normally competent for transduction by adenoviruses using antibodies, e.g., as described in U.S. Pat. No. 5,861,156 to George et al.; U.S. Pat. No. , 5,521,291 to Curiel et al., the disclosures of which are incorporated herein in their entirety by reference. Alternatively, adenoviruses can be targeted to cell-surface proteins (e.g., receptors) by expressing a binding protein or ligand on the surface of the adenovirus, e.g., as described by Douglas et al., (1996) *Nature Biotechnology* 14:1574; U.S. Pat. No. 5,770,442 to Wickham et al.; and U.S. Pat. No. 5,712,136 to Wickham et al. (the disclosures of which are all incorporated herein in their entirety).

In particular embodiments of the invention, cells are removed from a subject (e.g., dendritic cells, hepatic cells, cells of the central nervous system, myoblasts (including skeletal myoblasts), stems cells (including bone marrow cells), pancreatic cells), the adenovirus vector is introduced therein, and the cells are then replaced back into the subject. Methods of removing cells from subjects for treatment ex vivo, followed by introduction back into the subject are known in the art. In one exemplary embodiment, liver cells are removed from a subject, an inventive adenovirus expressing GAA (e.g., hGAA) is introduced therein, and the liver cell expressing the heterologous GAA gene is re-introduced back into the subject. As a further alternative, the cells that are manipulated and then introduced into the subject are provided from another subject or cell line.

A further aspect of the invention is a method of treating subjects in vivo with the inventive virus particles. Administration of the adenovirus particles of the present invention to a human subject or an animal in need thereof can be by any means known in the art for administering virus vectors. Preferably, at least about 1000, more preferably, at least about 10,000 infectious units are administered to the subject per treatment. Preferably, the subject is a mammalian subject, more preferably a human subject. Also preferred are subjects that have been diagnosed with a lysosomal storage disease or a glycogen storage disease. More preferred are subjects who have been diagnosed with GAA deficiency.

Type II GSD is an autosomal recessive genetic disorder that results in the loss of activity of GAA. This disease is caused by mutations in the GAA gene itself, and results in the accumulation of glycogen in the lysosomes of skeletal and cardiac muscles resulting in cardiomyopathy and skeletal myopathy. This condition results in death in the congenital (infant-onset) form and severe debilitation in the juvenile and adult onset forms.

In patients with Type II GSD (commonly called "Pompe disease", although this term formally refers to the infantile onset form of the disease) a deficiency of acid α-glucosidase causes massive accumulation of glycogen in lysosomes disrupting cellular function (Hirschhorn, in *The Metabolic and Molecular Basis of Inherited Disease,* 7th ed., Vol. 2 (eds, Scriver, C. R. et al.) 2443–2464 (McGraw-Hill, New York, 1995). In the most common infantile form, patients exhibit progressive muscle degeneration and cardiomyopathy and die before two years of age. Intravenous injection of enzyme obtained from human placenta or *Aspergillus niger* corrected enzyme and glycogen levels in liver but not in muscle or heart in patients with GAA deficiency (Hug et al., (1968) *Clin. Res.* 16:345; de Barsy et al., in *Enzyme Replacement Therapy in Lysosomal Storage Diseases* (eds Tager, J. M., Hooghwinkel, G. J. M. & Daems, W. T.) 277–279 (North-Holland Publishing Co., Amsterdam, 1974); Hug et al., (1967) *Cell Biol.* 35:C1).

GAA may be targeted to lysosomes via the mannose-6-phosphate receptor as well as by sequences associated with delayed cleavage of the signal peptide (in *The Metabolic and Molecular Basis of Inherited Disease,* 7th ed., Vol. 2 (eds, Scriver, C. R. et al.) 2443–2464 (McGraw-Hill, New York, 1995). Mannose-6-phosphate containing GAA enzyme from bovine testes, human urine, or medium of transiently transfected COS cells is taken up efficiently by cultured patient cells through the mannose-6-phosphate receptor (Hoefsloot et al., (1990) *Biochem. J.* 272:485; Oude-Elferink et al., (1984) *Eur. J. Biochem.* 139:489; Reuser et al., (1984) *Exp. Cell Res.* 155:178; Van der Ploeg et al., (1988) *J. Neurol.* 235:392). Bovine testes enzyme injected intravenously in mice is targeted to these tissues via the abundant mannose-6-phosphate receptor in heart and muscle tissue (Van der Ploeg et al., (1991) *J. Clin. Invest* 875:513).

For therapeutic use in humans, interspecies antigenicity requires the use of human enzyme (Hug et al., (1968) *Clin. Res.* 16:345), but the low abundance of the enzyme in human urine makes this source impractical (Oude-Elferink et al. (1984) *Eur. J. Biochem.* 139:489), making gene therapy approaches desirable.

Gene therapy is a particularly appropriate approach to treating GAA deficiency, in that recombinant human acid α-glucosidase made in bacteria was not catalytically active (Martiniuk et al. (1992) *DNA and Cell Biology* 11:701), and that recombinant enzyme made using baculovirus in insect cells was active, but it was not taken up efficiently by human fibroblasts (Wu et al., (1993) *Am. J. Hum. Genet.* 53(Supplement):963). In contrast, enzyme secreted by transiently transfected COS cells was active and taken up efficiently by fibroblasts (Hoefsloot et al., (1990) *Biochem. J.* 272:485).

Thus, it appears that the required post-translational modifications make it difficult to produce the enzyme in inexpensive expression systems (e.g., bacterial and insect systems) in a form where it is both active and capable of being taken up by the desired tissues. This complicates the manufacture of active, correctly modified enzyme outside of the organism to be treated. Introduction of the genetic material into the patient allows the synthesis to be performed in the cells of that organism and eliminates these difficulties.

Accordingly, a further aspect of the present invention is a method of treating a subject with GAA deficiency, including infantile (Pompe disease), juvenile and adult-onset forms of the disease. Preferably, the subject is a human subject. According to this method, the subject is administered a biologically-effective amount of a nucleotide sequence encoding a GAA protein to a non-muscle tissue of the subject. Preferably, the non-muscle tissue is an organ tissue (e.g., brain, pancreas, liver), most preferably, the liver. Nucleotide sequences encoding GAA are as described hereinabove, and include nucleotide sequences encoding the mature and precursor GAA protein. A "biologically-effective" amount of the nucleotide sequence is an amount that is sufficient to result in uptake and expression of the nucleotide sequence by at least one cell in the target tissue or organ. Preferably, at least about 10% of the target cells take up and express the nucleotide sequence encoding the GAA protein, more preferably at least about 25%, 50%, 75%, 90%, 95%, 99% or more of the target cells take up and express the nucleotide sequence. In still more preferred embodiments, essentially all of the target cells take up and express the nucleotide sequence encoding the GAA protein. In preferred embodiments, the nucleotide sequence encoding the GAA is administered to the liver. Modes of administration to the liver are as described hereinbelow.

The nucleotide sequence encoding the GAA can be administered by any method known in the art, including viral vectors, liposomes, direct DNA injection, and the like. Preferably, the nucleotide sequence is carried by a recombinant deleted adenovirus vector of the present invention (as described hereinabove).

Preferably, the cells (e.g., liver cells) take up the nucleotide sequence encoding the GAA protein, express the GAA protein, and secrete it into the circulatory system, where it is delivered to target tissues (e.g., muscle) in a therapeutic amount. By a "therapeutic amount" it is intended that the GAA is taken up by the target tissue and alleviates (i.e., decreases, mitigates, reduces) at least one of the symptoms of GAA deficiency in the subject. It is not necessary that the symptoms of GAA deficiency be eliminated, as long as the benefits outweigh the detriments of delivering the GAA to the target tissue.

The present inventors have found that it is advantageous to express the 110 kD precursor form of the GAA protein, containing mannose-6-phosphate residues. While not wishing to be bound by any particular theory of the invention, it appears that the GAA precursor is taken up by mannose-6- phosphate receptors on the surface of target tissues, and the internalized precursor protein is processed to its mature form, which then produces a therapeutic effect on the target tissue.

In practicing this embodiment of the invention, high-level expression of the GAA (or any other protein that is normally not secreted) by the liver (or other organ) is advantageous in that it appears that the natural mechanisms within the hepatocyte that target the GAA protein to the lysosomal compartment are saturated, thereby resulting in the "excess" protein entering the secretory pathway for delivery to target tissues and organs. The inventive adenoviruses are particularly suited to this purpose as adenoviruses are both highly infectious and produce high levels of transgene expression.

Accordingly, these methods overcome many of the problems raised by direct delivery of nucleotide sequences to muscle tissue. Administration of virus vector by intramuscular injection has demonstrated that the virus is localized to the site of injection (Tsujino et al. (1998) *Human Gene Therapy* 9:1609 Nicolino et al., (1998) *Human Molecular Genetics* 7:1695; Pauly et al., (1998) *Gene Therapy* 5:473; Zaretsky et al., (1997) *Hum. Gene Ther.* 8:1555). Accordingly, to deliver a GAA transgene to every muscle would require multiple injections directly into each of the muscle groups in Type II GSD patients. Moreover, after intravenous administration, adenovirus vectors normally transduce only a small number of muscle fibers (Stratford-Perricaudet et al., (1992). *Clin Invest.* 90:626; Kass-Eisler et al., (1994) *Gene Ther.* 1:395). The present inventors have found that expression of GAA from the liver after a single intravenous injection advantageously circumvents the problem of directly transducing cardiac and skeletal muscle target tissues.

Those skilled in the art will understand that the method described hereinabove can be used to produce any protein product in one tissue or organ and deliver it to another target tissue, e.g., via the circulatory system. Preferably, this method is used to produce other proteins or peptides associated with metabolic diseases, more preferably, lysosomal and glycogen storage diseases, each as described above. Also preferred are methods of producing proteins or peptides for delivery to muscle tissue. Further preferred are methods wherein the nucleotide sequence is introduced into the liver for expression and delivery to other target tissues.

Likewise, the present invention provides a method of producing high-level expression of other lysosomal proteins by the liver (or other organs and tissues). The protein can be expressed and secreted by the liver, and delivered to target tissues by the systemic circulation, where it is taken up by mannose-6-phosphate receptors on target tissues.

Alternatively, the present invention provides a method of treating a subject with GAA deficiency comprising administering to the subject a therapeutically-effective amount of the inventive deleted adenovirus particles (as described hereinabove) carrying a heterologous nucleotide sequence encoding a GAA (as described hereinabove). A "therapeutically-effective" amount as used herein is an amount of adenovirus that is sufficient to alleviate (e.g., mitigate, decrease, reduce) at least one of the symptoms associated with GAA deficiency. It is not necessary that the GAA eliminate the symptoms of GAA deficiency, as long as the benefits outweigh the detriments of GAA administration.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue (e.g., muscle) or organ injection (e.g., into the liver, into the brain for delivery to the central nervous system), alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

The adenovirus vectors disclosed herein may alternatively be administered to the lungs of a subject by any suitable means, but are preferably administered by administering an aerosol suspension of respirable particles comprised of the inventive adenovirus vectors, which the subject inhales. The respirable particles may be liquid or solid. Aerosols of liquid particles comprising the inventive adenovirus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the inventive virus vectors may likewise be produced with any solid particulate medicament aerosol generator, by techniques known in the pharmaceutical art.

In particularly preferred embodiments of the invention, the nucleotide sequence of interest is delivered to the liver of the subject. Administration to the liver can be achieved by any method known in the art, including, but not limited to intravenous administration, intraportal administration, intrabiliary administration, intra-arterial administration, and direct injection into the liver parenchyma.

Dosages will depend upon the mode of administration, the disease or condition to be treated, the individual subject's condition, the particular virus vector, and the gene to be delivered, and can be determined in a routine manner. Preferably, at least about 10,000 infectious units of the inventive adenovirus vectors are administered to the subject. Exemplary doses for achieving therapeutic effects are virus titers of $10^8$–$10^{14}$ particles, preferably $10^{10}$–$10^{13}$ particles, yet more preferably $10^{12}$ particles.

In particular embodiments of the invention, more than one administration (e.g., two, three, four, or more administrations) may be employed to achieve therapeutic levels of gene expression.

Having now described the invention, the same will be illustrated with reference to certain Examples, which are included herein for illustration purposes only, and which are not intended to be limiting of the invention.

EXAMPLE 1

Construction of the Ad Vector Deleted for the E2b-Polymerase Gene

The ~20 kb Xba-BamHI subfragment of pBHG11 (Microbix, Toronto) which contains the Ad E2b region was subcloned into pBluescriptKSII+ (Stratagene, La Jolla, Calif.), yielding pAXB. The pAXB plasmid was digested with BspEI, T4 DNA polymerase end-filled, BamHI digested, and the ~9.0 kilobase pair (kb) fragment was isolated. Plasmid pAXB was also digested with BspHI, T4 DNA polymerase end-filled, BamHI digested, and the ~13.7 kb fragment was ligated to the previously isolated 9.0 kb fragment, generating pAXB-Δpol. This subcloning strategy deleted 608 base pairs (Δpol: Ad5 nucleotide 7274–7881) within the amino terminus of the polymerase gene. This deletion also effectively removed ORF 9.4, present on the rightward reading strand in this region of the Ad genome. The Xba-BamHI subfragment of pAXB-Δpol was reintroduced into Xba-BamHI digested pBHG11, to generate pBHG11-Δpol (FIG. 1A).

Figure 1B:
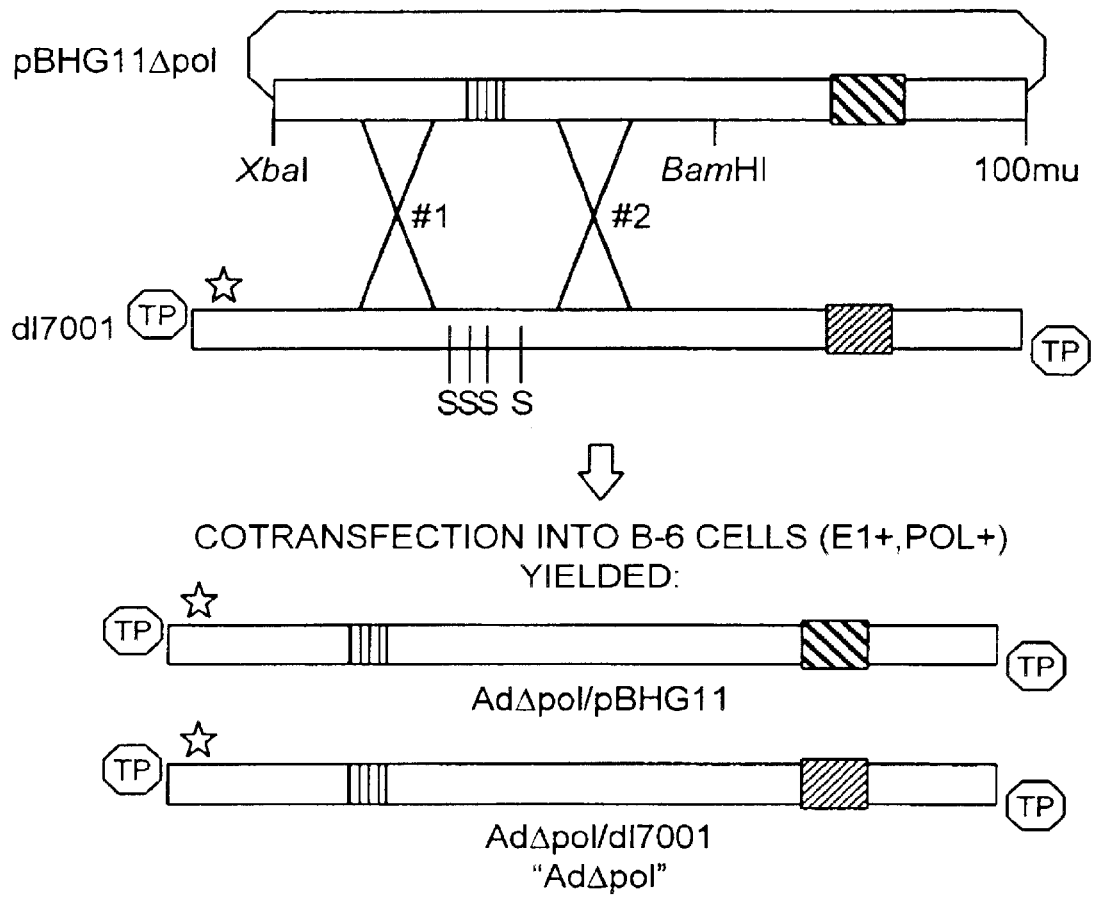

Theoretically, pBHG11-Δpol should have been capable of generating recombinant [E1-Δpol] Ad vectors after cotransfection of polymerase transcomplementing cells with a conventional Ad shuttle plasmid (Beft, J. J., et al., (1994) PNAS USA 91:8802–8806), unfortunately we were never able to generate such a vector with this approach. It is possible that our version of pBHG11 had acquired a cryptic point mutation prohibiting viable vector isolation. We therefore co-transfected the pBHG11-Δpol plasmid with ScaI digested dl7001 derived genomic DNA into the polymerase expressing cell line C-7 (FIG. 1B). The Ad dl7001 genomic DNA had an ~3.0 kb deletion within the E3 region of the Ad chromosome and was isolated as an intact virion DNA-terminal protein complex, dl7001-TP as described in Jones et al., Cell 13:181–88 (1978). The C7 cell line has been previously described (Amalfitano, et al., (1996) PNAS USA 93:3352–56). Briefly, these cells are capable of transcomplementing [E1-] Ad, as well as temperature-sensitive Ad mutants defective in both the polymerase and preterminal protein genes. This cell line was accomplished by the stable cointroduction of transgenes constitutively expressing the polymerase and preterminal protein genes into human 293 cells.

The co-transfection strategy resulted in the isolation of two viable viruses one with the Δpol deletion in the dl7001 background (AdΔpol) and one with the Δpol deletion in the pBHG11 background, AdΔpol/pBHG11). While both viruses were viable, the dl7001 derived virus demonstrated superior growth characteristics and was therefore selected for further work.

EXAMPLE 2

Construction of [E1-, Δpol, E3] and [E1-, Δpol, ΔpTP, E3-] Ad Vectors

Figure 1C:
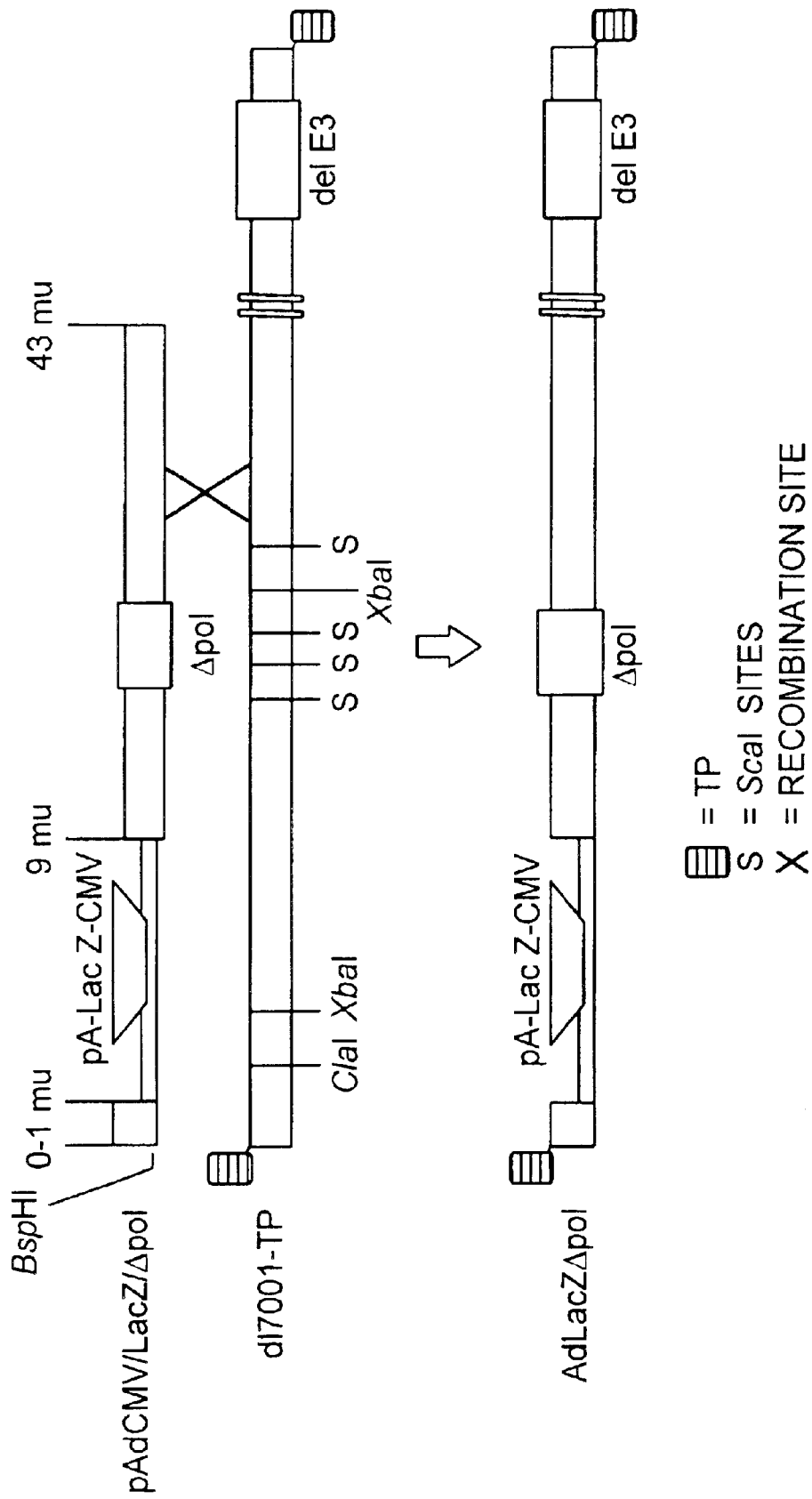

The AdΔpol virus was grown to high titer, and viral DNA isolated as previously described (Amalfitano, et al., (1996) PNAS USA 93:3352–56), digested with AscI, T4 polymerase end-filled, and Bst1107I digested. The ~9.3 kb blunt-ended Δpol containing fragment was subcloned into the Bst1107I digested shuttle plasmid pAdAscL. This subcloning strategy yielded pAdAscL-Δpol, a new shuttling plasmid specifically designed for the rapid isolation of recombinant Ad vectors deleted for both the Ad E1 and polymerase genes. The pAdAscL-Δpol plasmid contained nucleotides 1–15,671 of the left end of the Ad5 genome, but was effectively deleted for the E1 genes (Ad nt 358–3328, replaced by the AscI site) and also was deleted for the 608 bp Δpol deletion. A nuclear-targeted bacterial α-galactosidase transgene (LacZ) flanked by a minimal cytomegalovirus (CMV) promoter/enhancer element, the MINX intron (Niwa, M., et al., Genes Dev 4:1552–1559 (1990) and a simian virus 40 (SV-40) derived polyadenylation signal was subcloned into the AscI site of pAdAscL-Δpol, generating the shuttle plasmid pAdCMV/LacZ/Δpol (FIG. 1C). Ten micrograms of pAdCMV/LacZ/Δpol linearized with BspHI (restriction site within 60 bp of the left end of the Ad virus) was $CaPO_4$-cotransfected with 500 ng of XbaI, ClaI, and ScaI digested dl7001-TP virion DNA onto three 60 mm dishes containing $2 \times 10^6$ Ad-polymerase expressing C-7 cells (FIG. 1C). The multiple restriction enzyme digestion of dl7001 virion DNA significantly reduced the isolation of non-recombinant viruses after transfection. Sixteen hours after transfection the cells were harvested and mixed with ~$8 \times 10^6$ C-7 cells (non-transfected). The cell mixture was distributed to nine, 24-well tissue culture cluster plates, and incubated at 37.0° C. for 5–9 days. Individual wells demonstrating viral CPE were harvested, and the isolated virus amplified by repeated infection of either B-6 or C-7 cells. Isolation of the AdLacZΔpol recombinant vector was subsequently confirmed by (1) α-galactosidase conversion of the chromogenic substrate X-gal in cells transduced by the vector (2) DNA restriction mapping of the vector genome, and (3) by multiple functional studies.

To create Ad vectors containing deletions in both the polymerase and preterminal protein regions, shuttle plasmid pAdCMV/LacZ/Δpp was generated. The pAdCMV/LacZ/Δpol shuttle plasmid was digested with BspE1 (releasing a ~2.0 kb subfragment encoding the 3' end of the pTP gene). A previously-modified BspE1 subfragment of the pTP gene that contained a deletion within the pTP coding region was ligated into the BspE1-digested plasmid. This strategy resulted in the isolate of the shuttle plasmid pAdCMV/LacZ/Δpp, which was similar to pAdCMV/LacZ/Δpol except that it also contained a 433 bp deletion within the 3' end of the pTP gene. The deletion spanned nucleotides 9198 to 9630 of the Ad5 genome (deletion confirmed by sequencing). The deletions spanned the 3' portion of the pTP gene that encodes the critical serine residue required for pTP binding to the 5' end of the Ad genome, as well as other critical pTP functions.

Ten μg of pAdCMV/LacZ/Δpp was linearized with BspHI (restriction site within 60 bp of the left end of the Ad virus), was $CaPO_4$-cotransfected into C-7 cells with 500 ng of XbaI, ClaI, and ScaI digested dl7001 virion DNA, and incubated overnight. The transfected cells were subsequently distributed to ten 24-well dishes, allowing for clonal isolation of recombinant vectors. Several wells were found to contain recombinant vectors encoding β-galactosidase and simultaneously deleted for E1, E3, pol and pTP. Isolation of the multiply-deleted, AdLacZ/Δpp recombinant vector was also subsequently confirmed by (1) β-galactosidase conversion of the chromogenic substrate X-gal in cells transduced by the vector; (2) DNA restriction mapping of the vector genome; and (3) by multiple functional studies.

EXAMPLE 3

AdΔpol, AdLacZΔpol and AdLacZΔpp Vector Genome—Replication Studies

Figure 2:
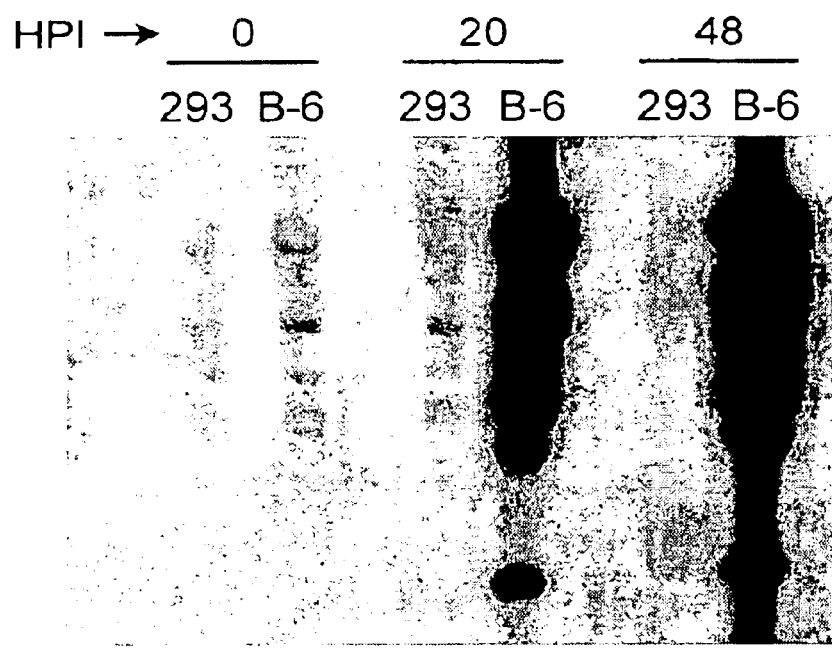
FIG. 2 shows AdLacZΔpol DNA replication after infection of 293 cells at MOI of 1.5 BFU at 0, 20 and 48 hours after infection.
Figure 3:
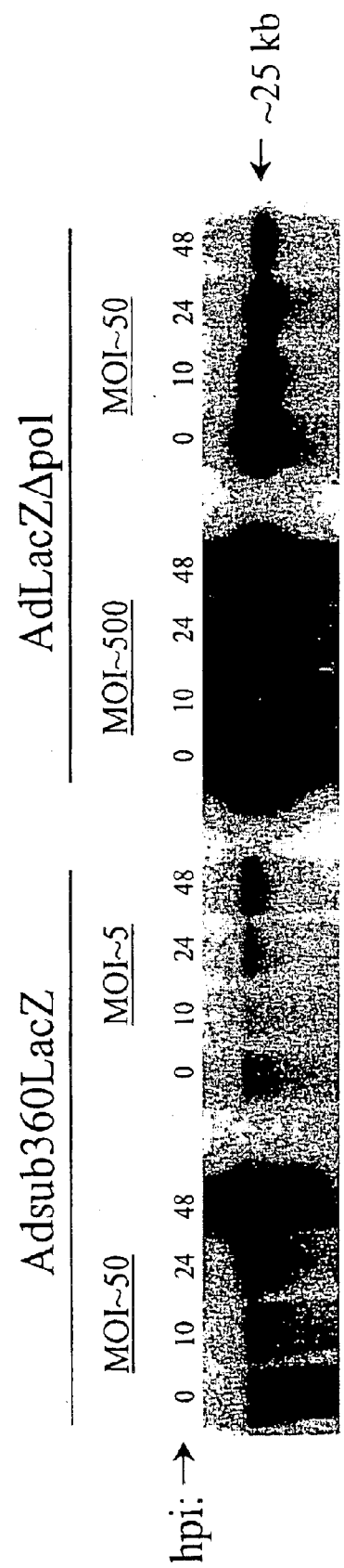
FIG. 3 shows AdLacZΔpol DNA replication after infection of B-6 cells at various MOIs at 0, 10, 24, and 48 hours after infection.

The respective cell lines were infected at the multiplicity of infection (MOI) indicated in FIGS. 2 and 3 with either AdΔpol, Adsub360LacZ (E1 deletion alone), AdLacZΔpol (E1 deletion+polymerase deletion) or AdLacZΔpp (E1 deletion, polymerase deletion, and pTP gene deletion), and incubated at 37.0° C. for the indicated times. Infected cells were then harvested and DNA prepared and analyzed as previously described (Amalfitano, et al., (1996) PNAS USA 93:3352–56). The results in FIGS. 2 and 3 show that even in the presence of high levels of E1 activity the Δpol modification conveys upon the vector a severe replication blockade. This block is significantly greater than that displayed by the first-generation Adsub360LacZ vector (FIG. 3). FIGS. 2 and 3 also show, in contrast to the reports using so-called "gutted" vectors which are essentially undetectable by 12–24 hours post infection, the input genomes persist to at least 75% of input virus levels at 24 hours and at least 50% at 48 hours.

EXAMPLE 4

Ad Vector Kinetics and One Step Burst Assays

Figure 4:
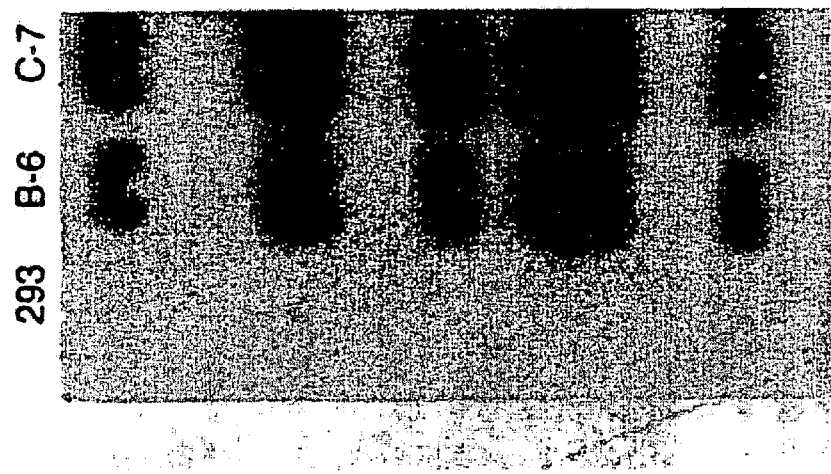
FIG. 4 shows kinetics of growth of AdLacZΔpol in 293, B-6 and C-7 cells.
Figure 5:
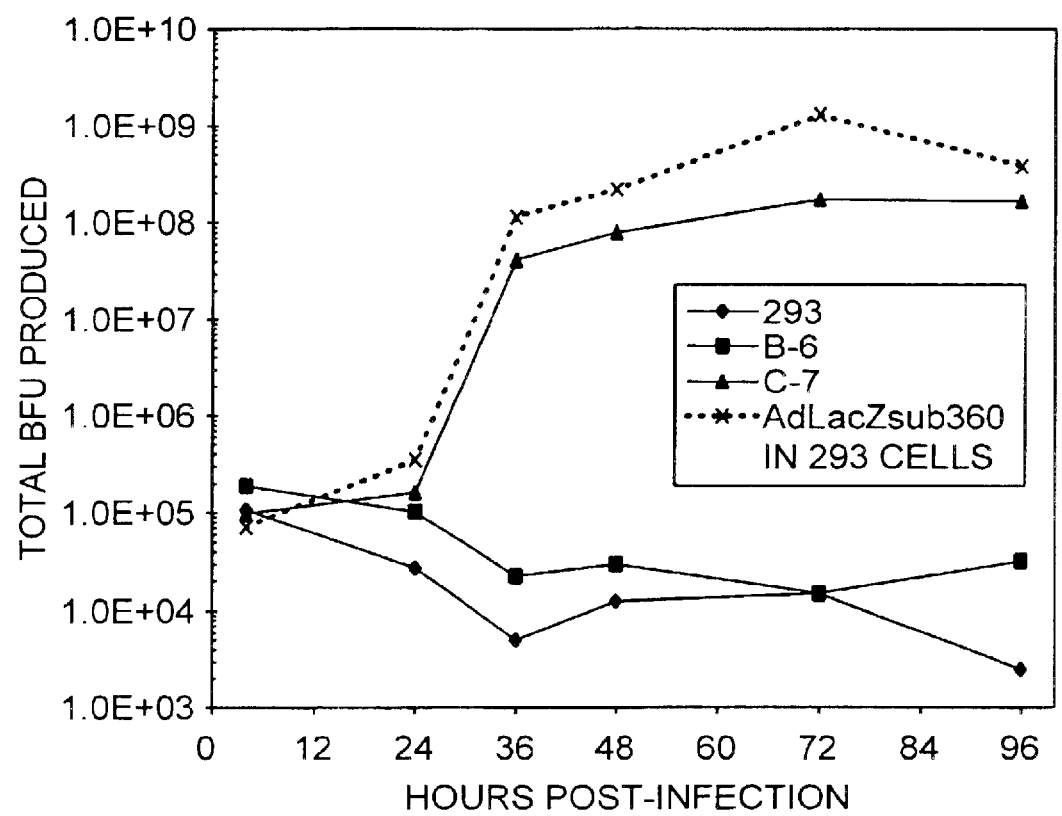
FIG. 5 shows kinetics of growth of AdLacZΔpp in cell lines 293, B-6 and C-7 and Adsub360LacZ in line 293.

Kinetics assay: Tissue culture dishes (60 mm) containing $2 \times 10^6$ 293 cells (express E1 protein), B-6 cells (express E1 and polymerase proteins), or C-7 cells (express E1, polymerase, and pTP proteins) were infected with AdLacZΔpol at an MOI of 0.01 β-galactosidase forming units (BFU) per cell or with AdLacZΔpp at an MOI of 0.5 β-galactosidase forming units (BFU) per cell. Cells and media were harvested from the dishes after incubation at 37.0° C. for the times indicated in FIGS. 4 and 5. The number of BFU produced was then determined by limiting dilution infection of C-7 cells or LP-293 cells. Eighteen hours later infected cells were stained for β-galactosidase activity, and the number of transducing particles was quantified by visual inspection of blue staining cells. The BFU generated in the original lysate was then determined by multiplying the number of stained nuclei by the appropriate dilution. An identical infection of 293 cells with Adsub360LacZ was included to compare the kinetics of growth of the AdLacZΔpp vector to the first-generation, Adsub360LacZ vector. Results are shown in FIGS. 4 and 5.

One step burst assay: $2 \times 10^6$ 293 or B-6 or C-7 cells were respectively infected with AdLacZΔpol, Adsub360LacZ or AdLacZΔpp (in triplicate) at an MOI of 5, incubated at 37.0° C. for 40 hours (Adsub360LacZ infection of 293 cells and AdLacZΔpol of B-6 cells) or 60 hours (AdLacZΔpp infection of C-7 cells), and the total BFU generated was determined by limiting dilution assay, as previously described for the kinetic assays.

EXAMPLE 5

Ad Vector Late Gene-Expression Studies

Figure 6:
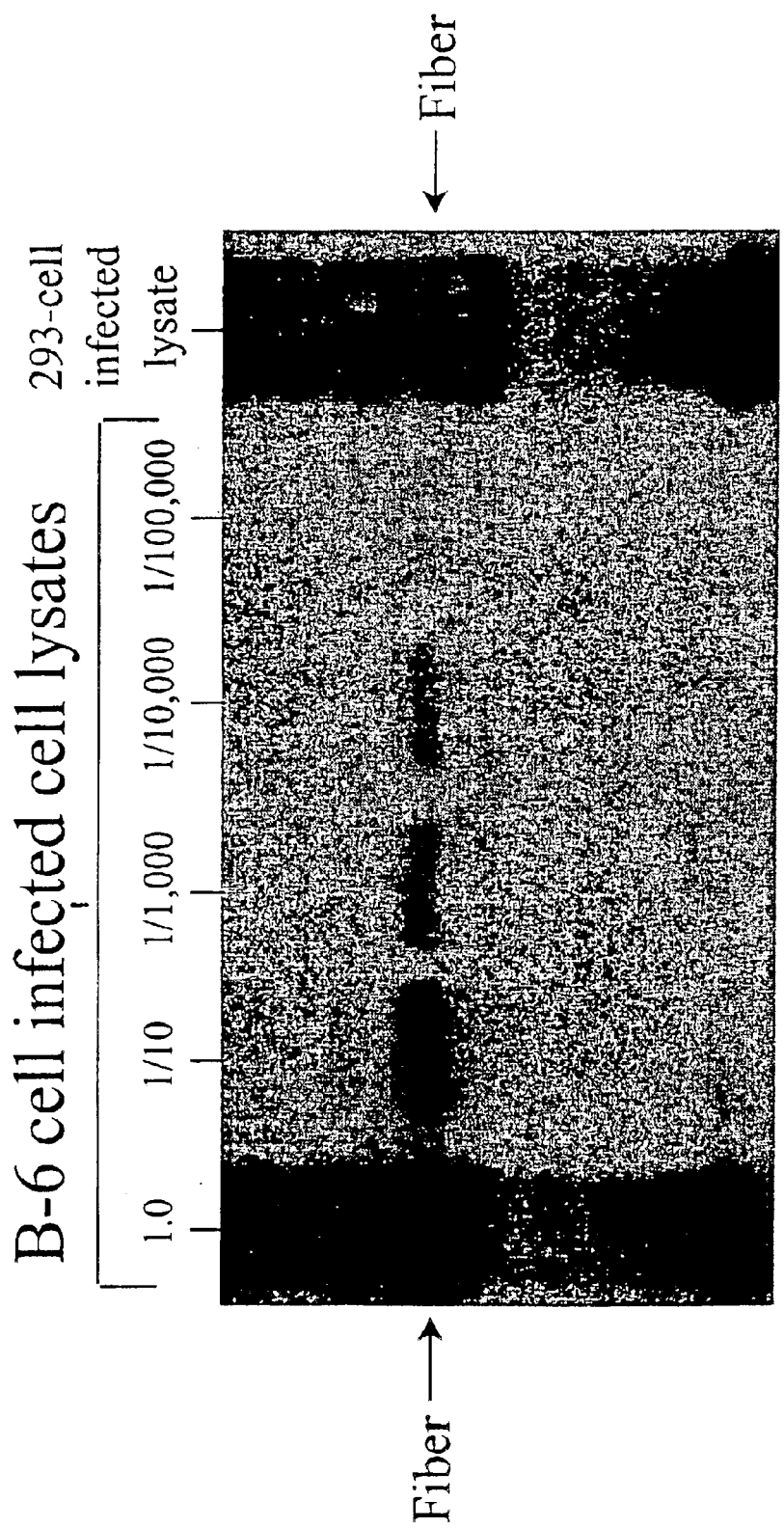
FIG. 6 shows AdLacZΔpol fiber protein synthesis after infection of 293 cells at MOI of 1.5 BFU.
Figure 7:
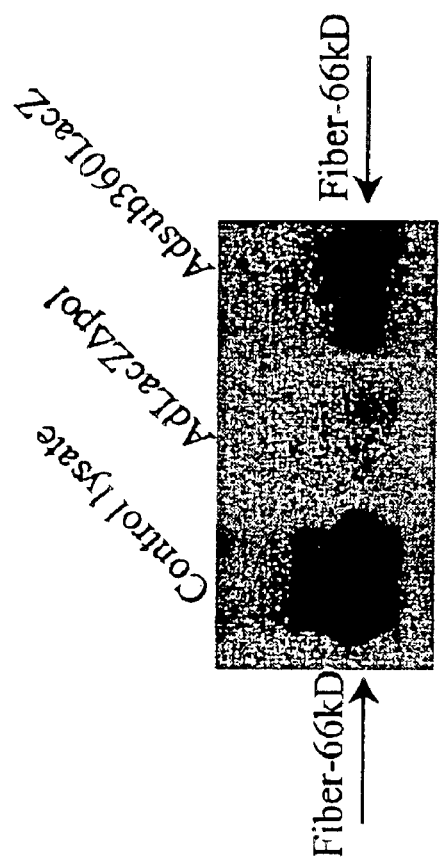
FIG. 7 shows AdLacZΔpol fiber protein synthesis after infection of B-6 cells at MOI of 1.5 BFU.
Figure 8:
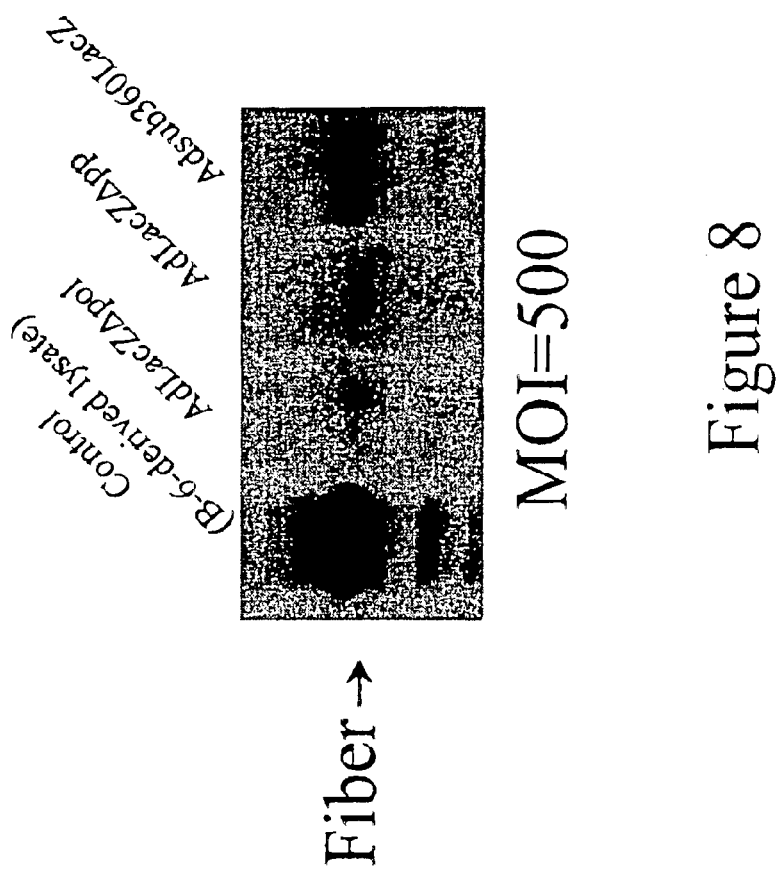
FIG. 8 shows the lack of expression of the adenovirus late gene product, fiber protein, in HeLa cells infected with AdLacZΔpol and AdLacZΔpp compared with Adsub360LacZ.

LP-293 cells, B-6 cells, or HeLa cells were infected with either AdΔpol, Adsub360LacZ, AdLacZΔpol or AdLacZΔpp at the indicated MOIs in FIGS. 6, 7 and 8 and incubated at 37.0° C. for 40–48 hours. Infected cells were harvested, rinsed with PBS, and lysed in Tris Cl (pH 6.8), 4% sodium-dodecyl sulfate, 10% glycerol, and 10% B-mercaptoethanol. Protein extracts were freeze thawed three times, DNA sheared, and protein concentrations determined via the Bradford assay utilizing the Coomassie Plus staining reagent (Pierce, Rockford, Ill.). Equivalent amounts of each protein lysate were heated to 100.0° C. for two minutes and electrophoretically separated in a 10% SDS-polyacrylamide gel. The separated proteins were wet-transferred to a Biotrace NT membrane (Gelman Sciences, Ann Arbor, Mich.) and probed with a rabbit polyclonal antibody (supplied by R. Gerard, University of Texas Southwestern, Dallas, Tex. generated against the knob portion of the 66 kD Ad-fiber protein monomer. Bound antibody was detected with the ECL detection system (Amersham Life Sciences, Arlington Heights, Ill.).

EXAMPLE 6

In Vivo Administration of AdLacZΔpol

Sixty 150 mm tissue culture plates containing ~$2.5 \times 10^7$ C-7 cells were infected with the AdLacZΔpol virus at an approximate MOI of 5, and incubated at 37.0° C. for 40 hours. The infected cells were harvested, resuspended in 10 mm Tris.Cl (pH 8.0), sonicated, and the virus purified by two rounds of cesium chloride density centrifugation. The viral containing band was desalted over a Sephadex CL-6B column (Pharmacia Biotech, Piscataway, N.J.), glycerol added to a concentration of 12%, and aliquots were stored at −80° C. The titer of this stock was $6 \times 10^{10}$ BFU per ml. The total number of particles in this stock was $1.2 \times 10^{12}$, as determined by measurement of the O.D. 260 of an aliquot of the virus after SDS-lysis (Mittereder et al., (1996) *J. Virol.* 70:7498), therefore the bioactivity of the preparation was at a minimum of 0.05, ($6'10^{10}/1.2 \times 10^{12}$) a value similar to that achieved after isolation of first-generation Ad vectors (Id.). Seven to nine week old BALB/c mice were injected in the left tibialis anterior muscle or via the tail vein with a PBS solution containing $1 \times 10^9$ BFU of AdLacZΔpol. Five-six days after infection, the mice were sacrificed, and the muscle or liver specimens removed and frozen in OCT Compound. Cryosections were obtained, briefly fixed in a 3.7% formaldehyde/PBS solution, stained overnight for β-galactosidase activity, and rinsed in PBS and briefly post-fixed in 3.7% formaldehyde, 0.5% glutaraldehyde in PBS. Sections were then eosin counterstained and photographed. Results are shown in FIG. 9 and as described in Example 11.

EXAMPLE 7

ΔPol Vectors

Figure 10:
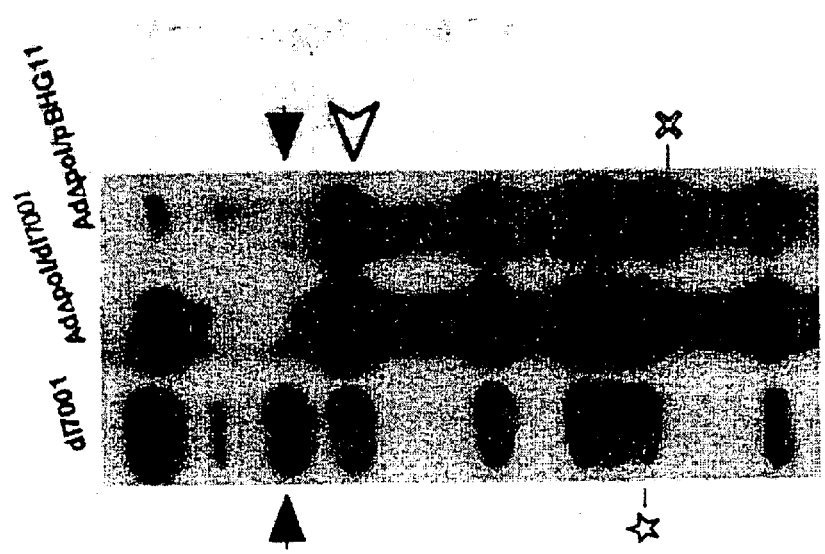
FIG. 10 shows a HindIII restriction enzyme analysis for each of the indicated adenoviruses.

The isolation of packaging cell lines that co-express the Ad E1 and polymerase genes, based upon their ability to support the growth of Ad-polymerase temperature sensitive (ts)-mutants has previously been described (Amalfitano et al., (1996) *Proc. Natl. Acad. Sci. USA* 93:3352–3356). The virus AdΔpol, constructed as described herein and as shown in FIG. 1, contains a 608 bp deletion within the polymerase gene (FIG. 1, Panel B). The Δpol deletion described in Example 1 also effectively deleted ORF 9.4, with no consequence in regard to the growth potential of the resultant viruses. Confirmation of the AdΔpol genomic structure was accomplished by restriction enzyme digestion (FIG. 10). AdΔpol had a severe replication defect when not grown in cells expressing the Ad polymerase, confirming the lack of polymerase activity secondary to the introduced 608 bp deletion (FIG. 4). Despite high levels of E1 activity (both from the AdΔpol genome as well as the E1 expressing 293 cells) AdΔpol is incapable of significant replication in cells other than the C7 cell line. This contrasts with the behavior of first generation Ad vectors in vitro and in vivo which are significantly leaky even in presumably non-permissive hosts and target cells (Lieber, A. et al., (1996) Journal of Virology 70:8944–8960, Yang, Y, et al., (1994) Nat Genet 7:362–369).

EXAMPLE 8

Isolation and Growth Kinetics of AdLacZΔpol

Figure 11:
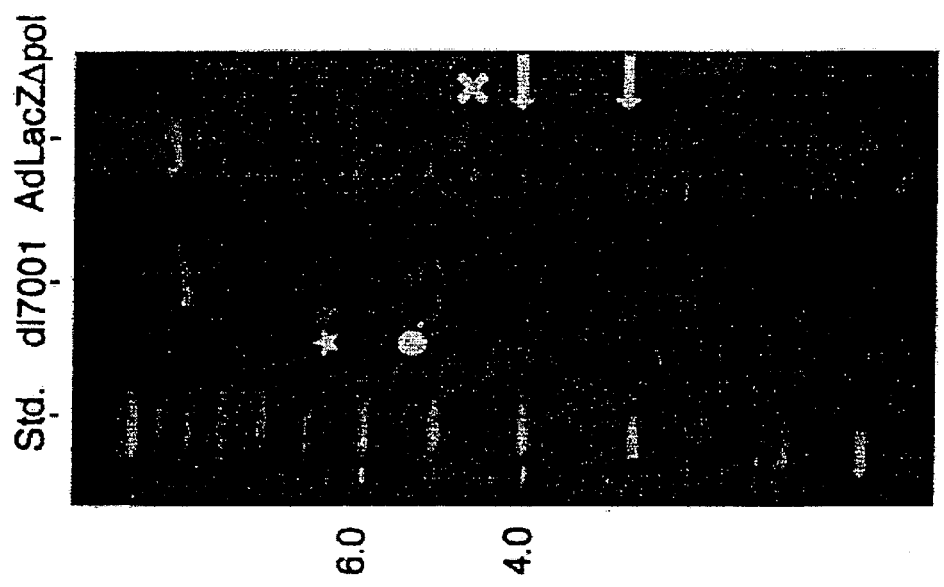
FIG. 11 shows NotI and EcoRI digests of AdLacZΔpol infected B-6 cells compared with NotI and EcoRI digested dl7001 DNA.
Figure 12:
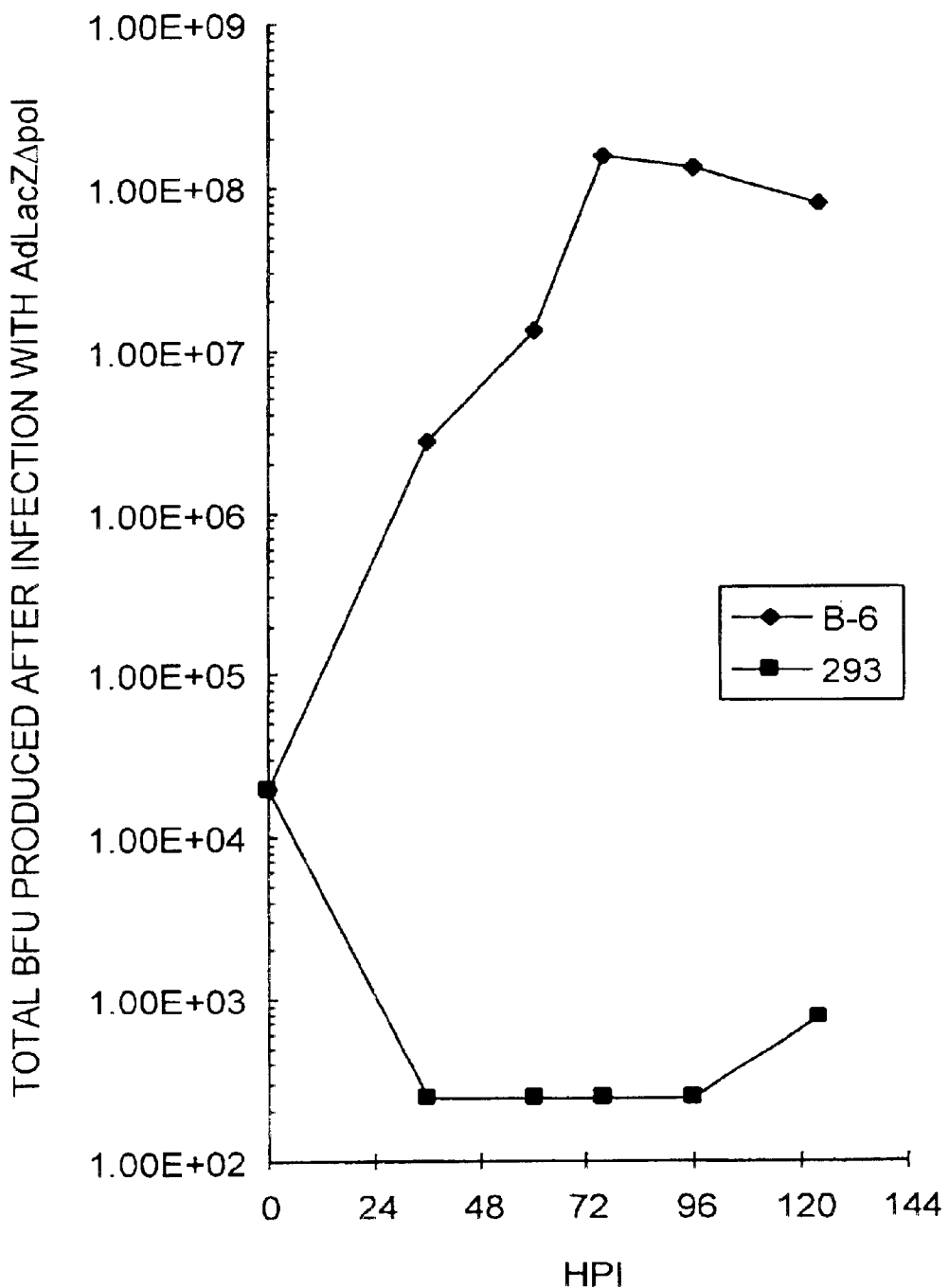
FIG. 12 shows relative growth of AdLacZΔpol when infected at an MOI of 0.01 into 293 cells (provide E1) and B-6 cells (provide E1 and pol).

To facilitate the production of [E1-, E3-, Δpol] Ad vectors, a shuttling system was engineered for their construction (FIG. 1, Panel C). Co-transfection of linearized pAdCMV/LacZ/Δpol with multiply digested dl7001 DNA-TP complex resulted in the successful isolation of AdLacZΔpol. The genomic structure of AdLacZΔpol was confirmed by restriction enzyme analysis (FIG. 11). The kinetics of AdLacZΔpol growth was then determined in 293 cells and B-6 cells (FIG. 12). Note the dramatic lack of production of infectious AdLacZΔpol in LP-293 cells, despite the presence of high levels of E1 activity in this cell line. Furthermore, one step burst assays of B-6 cells infected with AdLacZΔpol or Adsub360LacZ clearly demonstrated that the AdLacZΔpol vector could be produced to as high (or higher) a titer as the Adsub360LacZ vector. For example, when $2 \times 10^6$ B-6 cells were infected at an MOI of 5 BFU with AdLacZΔpol or Adsub360LacZ (each in triplicate) the total BFU released after a 40 hour infection was $1.18 \times 10^8 \pm 4.2 \times 10^7$ BFU for AdLacZΔpol, and $1.78 \times 10^7 \pm 8.9 \times 10^6$ BFU for Adsub360LacZ. High titer growth of the AdLacZΔpol vector in the B-6 cell line is a significant attribute of the present invention, not only for lower cost and higher efficiency clinical grade production, but also because previously described packaging cell lines designed to allow the growth of modified Ad vectors are sometimes inefficient, likely due to the toxicity of the coexpressed Ad genes (Zhou, H. S., et al., (1996) Journal of Virology 70:7030–7038).

EXAMPLE 9

AdLacZΔpol is Blocked in Replication

Infection of B-6 cells allowed high level replication of the AdLacZΔpol genomes; however, an identical infection of 293 cells demonstrated a dramatic block of replication (FIG. 2). This result confirmed that, even in the presence of high levels of E1 activity, the Δpol modification of the present invention conveys upon the vector a severe replication blockade. Despite a lack of significant replication, the AdΔpol and AdLacZΔpol genomes were still present at near input levels 24 hours post-infection in 293 cells, and decreased only after 48 hours post-infection. Supporting these observations, high titer infection of HeLa cells (lacking both E1 and polymerase activities) with AdLacZΔpol demonstrated a significantly greater replication block than displayed by the first generation Adsub360LacZ vector (FIG. 3).

Despite the lack of replication demonstrated above, the AdLacZΔpol persisted to at least 75% of input virus levels within 24 hours of HeLa cell infection, and dropped to 50% of input virus by 48 hours after infection (FIG. 3). This result is in contrast to a report utilizing "gutted Ad vectors" that are also devoid of much of the Ad genome (Lieber, et al., (1996) J. Virol. 70:8944–60). In the latter report, 50% of the "gutted Ad vector" genomes were degraded within 5 hours of transduction of cells both in vitro and in vivo, and was essentially undetectable by 12–24 hours post transduction. Id. Consequently, unlike earlier massively deleted "gutted" Ad vectors, Δpol Ad vectors of the present invention severely blocked in their ability to replicate (even in the presence of excessive levels of E1 activity), but unlike gutted Ad vectors, this blockade does not simultaneously result in a rapid loss (destabilization) of their genomes.

EXAMPLE 10

AdLacZΔpol Late Gene Expression is Blocked in Noncomplementing Cell Lines

Cell types 293 and B-6 were infected with AdLacZΔpol and assessed for viral late gene expression, as determined by fiber protein accumulation. As shown in FIG. 6, there is at least a 10,000 fold reduction in the ability of the AdLacZΔpol vector to produce the fiber protein after infection of 293 cells, in contrast to infection of the polymerase-complementing B-6 cell line. Further, HeLa cells when infected with the AdLacZΔpol virus do not produce detectable fiber protein (FIG. 7). In contrast, fiber expression is readily detected after infection of HeLa cells with the Adsub360LacZ. Together, these results demonstrated another benefit of the AdLacZΔpol vector, a significantly decreased expression of viral late genes, secondary to the severe replication blockade afforded by the presence of the Δpol in the modified vector. Ad late gene products such as the fiber protein are potent antigenic epitopes in vivo, therefore decreased expression of the late, E1, and polymerase gene products may result in a greater efficacy for AdΔpol vectors in vivo.

EXAMPLE 11

In Vivo Transduction with the AdLacZΔpol Vector $1\times10^9$ BFU of AdLacZΔpol were injected intravenously (for liver transduction) or into the left tibialis anterior muscle of 7–9 week old BALB/C mice. Five to six days later the respective tissues were excised and stained for β-galactosidase activity. As demonstrated in FIG. 9, the AdLacZΔpol vector is capable of extensive transduction and expression of the bacterial β-galactosidase gene in liver tissues. The same result was achieved after intramuscular administration of AdLacZΔpol. Therefore, despite the additional replication blockade provided by the deletion of both the E1 and polymerase genes in the AdLacZΔpol vector, efficient transduction and transgene expression occurred in these tissues. This again is in contrast to some recently described helper virus-dependent Ad vector systems, whose modified mini-genomes were rapidly eliminated in vivo, before significant transgene expression occurred (Lieber, A. et al., (1996) Journal of Virology 70:8944–8960).

EXAMPLE 12

Construction of Multiply-Deleted ΔpTP Ad Vectors

Figure 13:
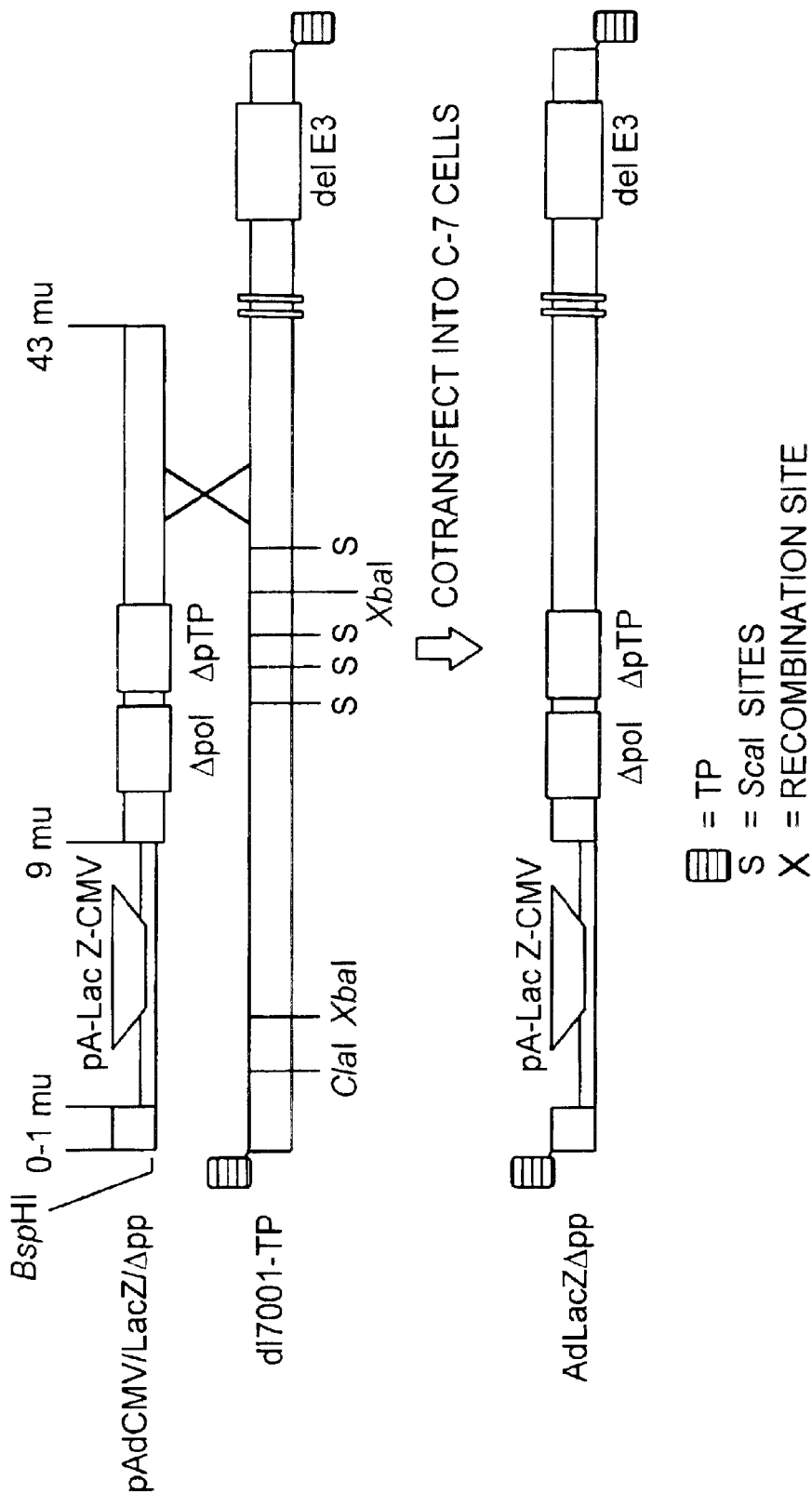
FIG. 13 shows a diagrammatic representation of the steps used to isolate AdLacZΔpp.

The construction of the pAdCMV/LacZ/Δpol shuttling plasmid and the E1, E3, and polymerase deleted vector AdLacZΔpol has been described in Example 1 and Example 2. To create a shuttle plasmid with deletions in the preterminal protein region, the pAdCMV/LacZ/Δpol shuttle plasmid is digested with BspE1 (releasing a ~2.0 kb subfragment encoding the 3' end of the pTP gene) and reinserted into a previously modified BspE1 subfragment that contains a deletion within the pTP coding region. The resulting shuttling plasmid pAdCMV/LacZ/Δpp was isolated. This plasmid is similar to pAdCMV/LacZΔpol, except that it also contained a 433 bp deletion within the 3' end of the pTP gene (FIG. 13). The 433 bp pTP deletion spans nucleotides 9198–9630 of the Ad5 genome. This fact was confirmed by sequencing across the deletion. Creation of the pAdCMV/LacZΔpp resulted in the deletion of a significant portion of the pTP coding region, and spanned the 3' portion of the pTP gene that encodes the critical serine residue required for pTP binding to the 5' end of the Ad genome, as well as other critical pTP functions (Schaack J, et al., (1990) Genes Dev 4:1197–208, Webster A, et al., (1997) Journal of Virology; 71:6381–9).

Ten micrograms of pAdCMV/LacZ/Δpp linearized with BspHI (restriction site within 60 bp of the left end of the Ad virus) was $CaPO_4$- cotransfected into C-7 cells with 500 ng of XbaI, ClaI, and ScaI digested dl7001 virion DNA, and processed as described in Example 2 above. Isolation of the multiply deleted, AdLacZΔpp recombinant vector was subsequently confirmed by 1) β-galactosidase conversion of the chromogenic substrate X-gal in cells transduced by the vector 2) DNA restriction mapping of the vector genome, and 3) by multiple functional studies (see below).

In order to grow the multiply-deleted Ad vectors of the present invention, a packaging cell line is required which can transcomplement all of the essential gene functions deleted in the vectors. We have demonstrated that the B-6 and C-7 cell lines, isolated and characterized for their ability to complement temperature sensitive polymerase (B-6 and C-7) and pTP mutants (C-7) (Amalfitano, A., et al., (1996) PNAS USA 93:3352–3356) also complement polymerase, IVa2 and/or pTP deletion mutants.

EXAMPLE 13

Transcomplementation of Δpp Ad Vectors by C-7 Cells

The present investigations have found that ΔTP and Δpol Ad vectors can be packaged when grown in cell lines selected for their ability to support the growth of adenovirus strains with temperature sensitive (ts) mutations within the polymerase or pTP genes, e.g., the C-7 cell line (Amalfitano et al., (1997) *Gene Ther.* 4:258).

Figure 14:
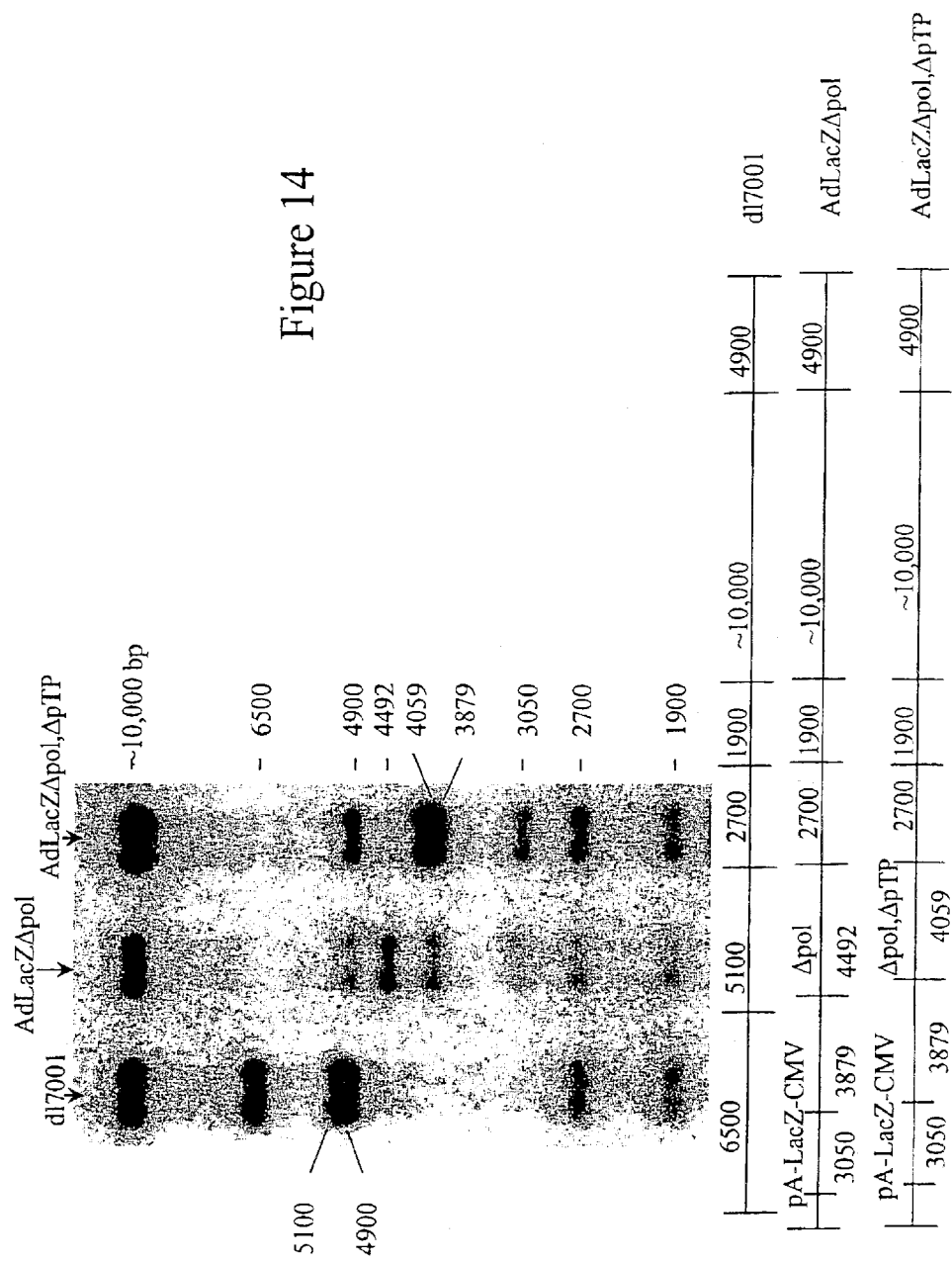
FIG. 14 shows restriction enzyme analysis to confirm the genomic structure of Δpol, ΔpTP (referred to as AdLacZΔpp) and compares it to other adenovirus vectors of known genome structure.
Figure 15:
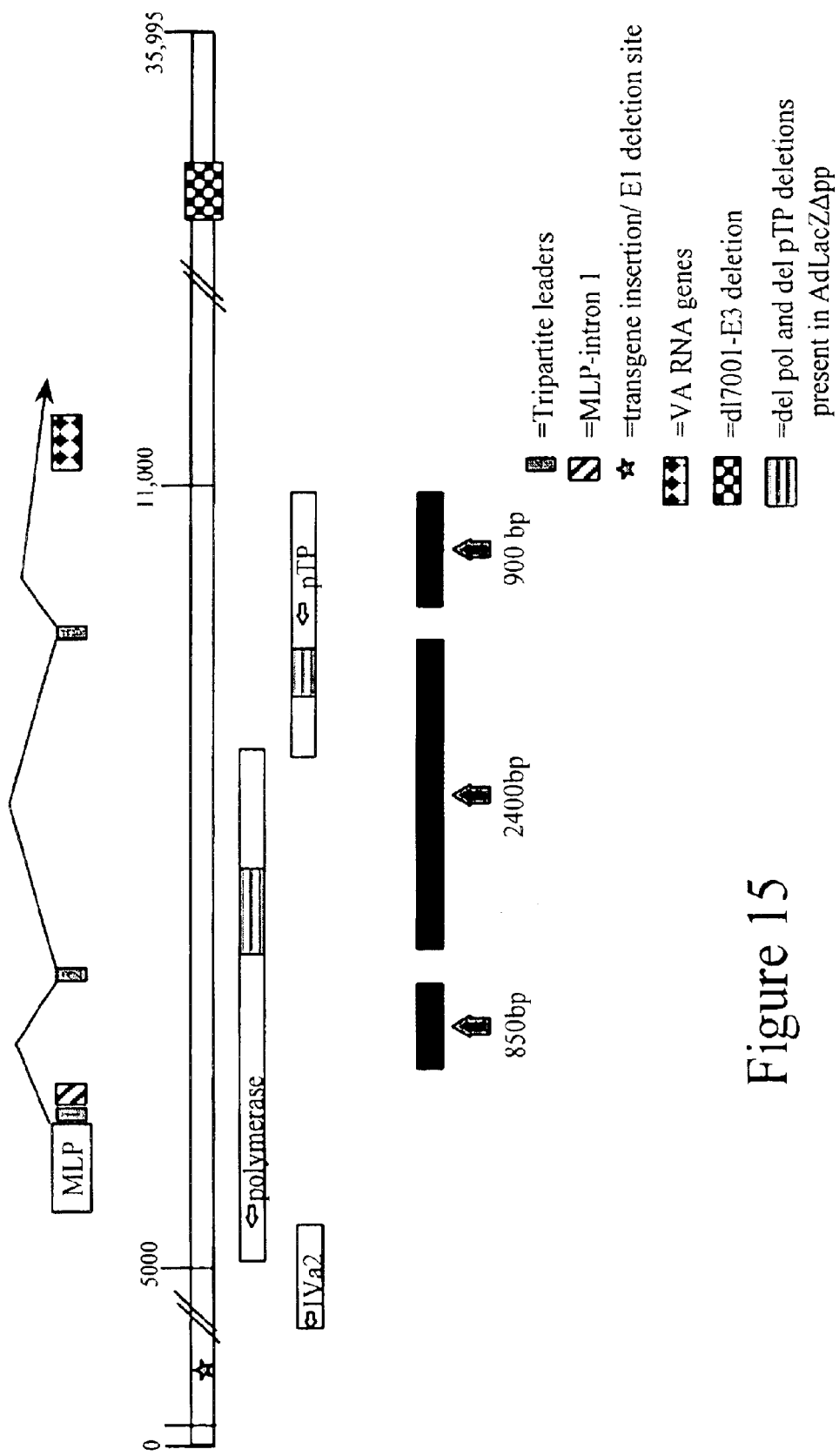
FIG. 15 is a schematic representation of the portion of the adenovirus genome encoding the polymerase and preterminal protein open-reading frames, and indicating the areas deleted in the AdLacZΔpp vector.

Ad vectors that simultaneously lack the Ad E1, E3, polymerase, and pTP gene activities are capable of high level growth on such strains, such as the preferred C-7 strain. A shuttling system was developed to facilitate the production of a multiply deleted Ad vectors. Targeted homologous recombination after co-transfection of the linearized pAdCMV/LacZ/Δpp shuttle plasmid with multiply digested dl7001 DNA resulted in the successful generation of a unique Ad vector simultaneously deleted for the E1, E3, polymerase, and pTP gene activities, referred to as AdLacZΔpp (FIG. 13). Restriction enzyme analysis was utilized to confirm the genomic structure of AdLacZΔpp (FIG. 14). Note that in comparison to the AdLacZΔpol vector (deleted for portions of the E1, E3, and polymerase genes), the AdLacZΔpp vector genome contains an additional 433 bp deletion, that represented the location of the pTP-specific deletion (FIG. 15). The deletion within the pTP open reading frame eliminates the critical portion of the protein absolutely required for normal function, and completely inactivates pTP activities in resultant vectors containing this deletion.

To demonstrate this inactivation, the growth kinetics of AdLacZΔpp were evaluated when transcomplementation was attempted in 293, B-6, or C-7 cells (FIG. 5). Despite the presence of high levels of E1 activity in the 293 cell line, or of both E1 and polymerase gene activities in the B-6 cell lines, no infectious AdLacZΔpp was produced after infection of either cell line, even after prolonged incubation times. This result demonstrated that polymerase and pTP gene functions were disabled in the AdLacZΔpp vector, and that this blockade could only be relieved when the vector was grown in the multiply-transcomplementing C-7 cell line. The kinetics of growth of AdLacZΔpp in C-7 cells was slightly delayed when compared to the growth of the first generation vector Adsub360LacZ in 293 cells, although final titers were only slightly reduced compared to the first generation vector. For example, one step burst assays of C-7 cells infected with AdLacZΔpp at an MOI of 5 produced a titer of $1.0 \times 10^8 \pm 3.3 \times 10^7$ BFU (n=3) as compared to Adsub360LacZ vector titer production of $2.0 \times 10^8 \pm 3.7 \times 10^7$ BFU in 293 cells (n=3). High titer growth of the AdLacZΔpp vector in the C-7 packaging cell line was extremely significant. This result demonstrates that the vectors of the present invention can be produced to high titer without the need for a contaminating, transcomplementing helper virus.

Figure 16:
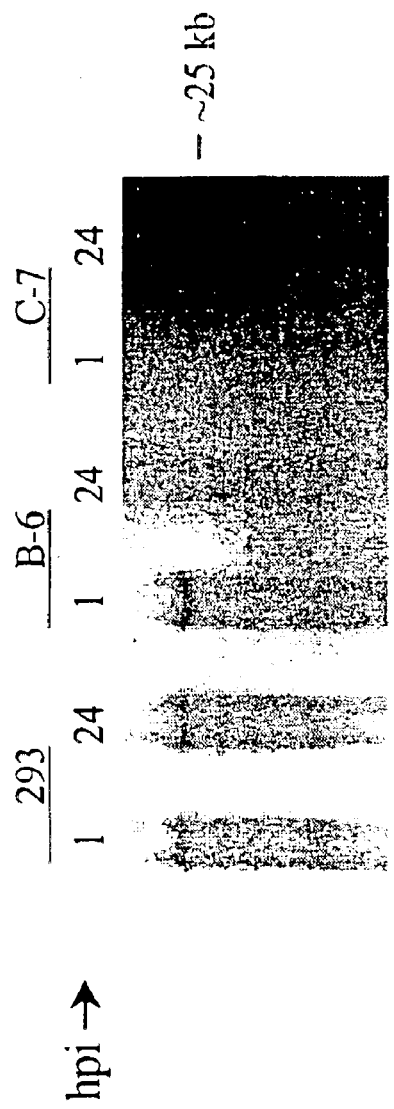
FIG. 16 shows the level of replication in AdLacZΔpp when grown in the packaging cell line C-7 which provides E1, pol and pTP gene activity as compared with packaging cell lines 293 (provides only E1) and B-6 (provided E1 and pol).
Figure 17:
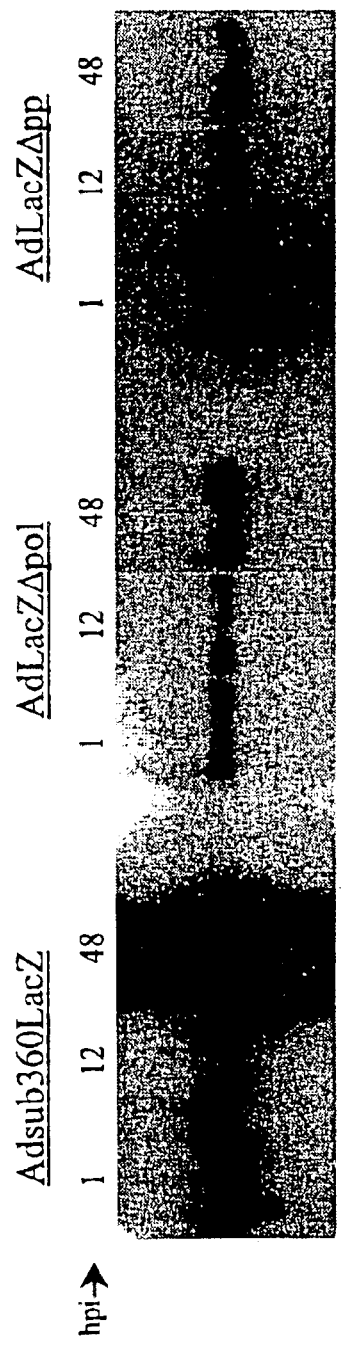
FIG. 17 shows the level of replication of Adsub360LacZ, AdLacZΔpol, or AdLacZΔpp when grown in HeLa cells, which lack E1, polymerase, and pTP activities. The AdLacZΔpol and AdLacZΔpp genomes persisted 48 hours after infection.

Infection of 293 or B-6 cells with AdLacZΔpp demonstrated that the Δpp deletion introduced a dramatic block to replication of the AdLacZΔpp genome in the respective cell lines (FIG. 16). However, an identical infection of C-7 cells allowed high level replication of the AdLacZΔpp genome. The example demonstrates that the Δpp deletion conveyed upon the vector a severe replication blockade, even in the presence of E1 activity in 293 cells, or of both E1 and polymerase activities in B6 cells. This is in contrast to previously reported studies with the ts pTP mutant sub-100, which is temperature sensitive due to an in-frame amino acid addition within the amino-terminus of the pTP protein (Amalfitano A, et al, (1997) *Gene Ther.,* 4:258). In this previous study, the sub-100 mutant demonstrated a replication defect that was effectively transcomplemented by the presence of the polymerase protein. Id. Clearly, the presence of the 433 bp pTP deletion significantly inhibited AdLacZΔpp genome replication, due to complete elimination of critical pTP functions. In addition, the input AdLacZΔpp genomes remained present at near input levels 24 hours post infection in 293 or B-6 cells. The same result was also confirmed after infection of HeLa cells (lacking E1, polymerase, and pTP activities) with AdLacZΔpp (FIG. 17). In contrast to the significant replication observed after infection of HeLa cells with the first generation vector Adsub360LacZ, the AdLacZΔpp input genomes failed to replicate and persisted at near input levels for up to 48 hours after HeLa cell infection (FIG. 17). This result demonstrates that absence of pTP gene activities (and a complete lack of replication) in the multiply-deleted Ad vectors of the present invention did not result in a destabilization and/or a rapid loss of the multiply-deleted vector genomes.

EXAMPLE 14

ΔTP Deletions Prevent Ad Late Gene Expression

Many DNA viruses (polyoma, simian virus-40, Ad) have life cycles that are highlighted by early and late phases. Usually the early phase reflects the expression of viral genes required for replication of the viral genome. The late phase reflects the high level expression of viral structural proteins after viral genome replication has commenced. For adenovirus, the expression of the late genes is dependent on the physical replication of the genome, an event that acts in cis to activate the viral major late promoter (MLP) (Thomas et al., (1980) *Cell* 22:523).

The results described herein demonstrate that the ΔTP deletion mutant also prevent Ad late gene expression. The late gene expression blockade was demonstrated after HeLa cells were infected with the AdLacZΔpp vector (FIG. 8). Fiber protein expression (fiber mRNA transcripts are derived from initiation at the MLP) was readily detected after infection of HeLa cells with the Adsub360LacZ vector, previously shown to be capable of replication in 293 cells. In contrast, infection of HeLa cells with the AdLacZΔpp vector did not result in detectable fiber expression.

EXAMPLE 15

In Vivo Administration of AdLacZΔpp

Sixty, 150mm tissue culture plates containing $\sim 2.5 \times 10^7$ C-7 cells were infected with the AdLacZΔpp virus at an approximate MOI of 5, and incubated at 37.0° C. for 48 hours. Virus from the infected cells was isolated by CSCl₂ banding as described in Example 11. Amounts of infectious vector obtained were essentially equivalent to that obtained with first generation Ad vectors. The concentrated virus was desalted after overnight dialysis in phosphate-buffered saline (PBS) at 4.0° C., glycerol added, and aliquots stored at −20° C. Seven to nine week old severe-combined immune deficient (SCID) or C57Bl/6 mice were injected intravenously with a PBS solution (typically 150–200 uL) containing $4 \times 10^9$ BFU of the respective vectors. All animal experiments were carried out as previously approved by the Duke University Animal Care and Use Committee. Three days after infection, the mice were sacrificed, and liver specimens were frozen in OCT Compound. Cryosections were obtained, briefly fixed in a 3.7% glutaraldehyde/PBS solution, stained overnight for β-galactosidase activity, and photographed, as described in Example 11.

EXAMPLE 16

Results of In Vivo Administration of AdLacZΔpp

Figure 18:
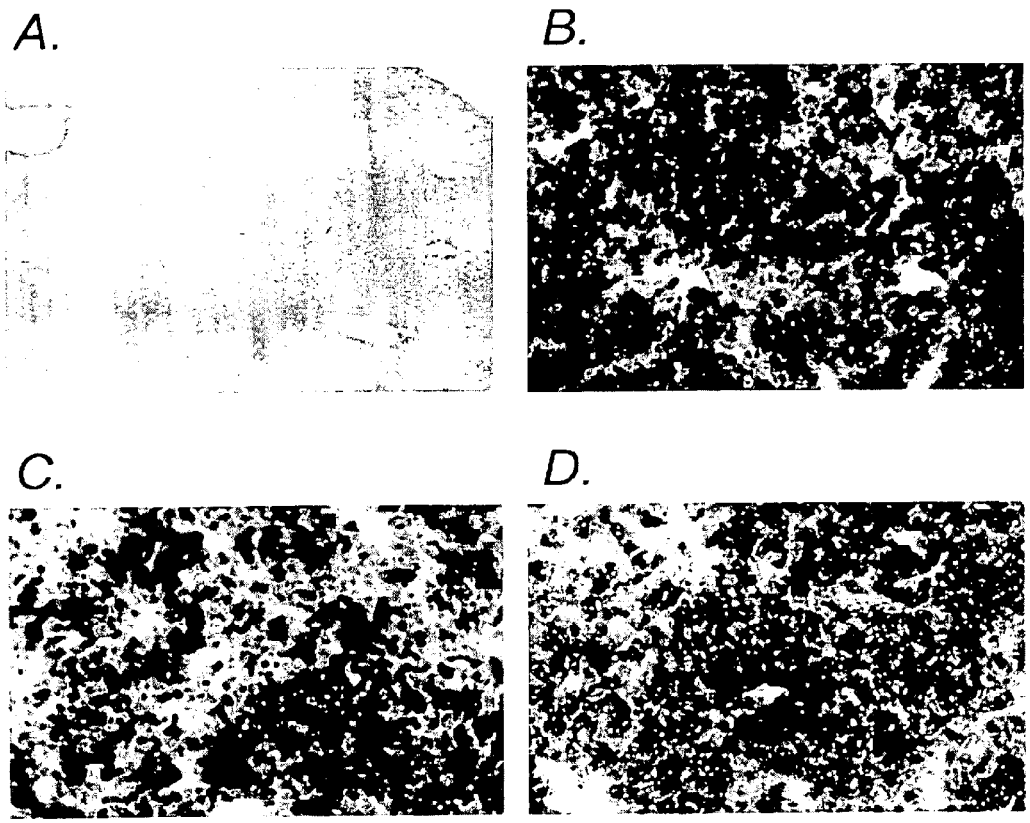
FIG. 18 shows expression of the LacZ genes in vivo after introduction of Adsub360LacZ (Panel B), AdLacZΔpp (Panel C) or AdLacZΔpol (Panel D) or mock infection (Panel A) into 7- to 9-week-old SCID or C57B1/6 immune deficient mice.

The multiply deleted Ad vectors of the present invention are capable of in vivo transduction with modified Ad vectors. 4×10⁹ β-galactosidase forming units (BFUs) of the AdLacZΔpp vector were respectively injected intravenously (for liver transduction) into 7–9 week old severe combined immune deficient (SCID) or C57BI/6 female mice. Similar injections were carried out with the first-generation vector Adsub360LacZ, and with AdLacZΔpol. Three days later liver tissues were excised and stained for β-galactosidase activity. As demonstrated in FIG. 18, the AdLacZΔpp vector is capable of extensive transduction and expression of the bacterial β-galactosidase gene in liver tissues of injected SCID mice (also in C57BI/6 mice, data not shown). The level of transduction was essentially equivalent to that demonstrated with the use of other, less extensively modified vectors (FIG. 18). Therefore, efficient transduction and transgene expression occurred in hepatic tissues using vectors according to the present invention despite the deletion of the E1, polymerase and pTP genes in the AdLacZΔpp vector.

The inability of first-generation Ad vectors to persist after transduction of immune-competent hosts has been the major barrier to Ad mediated gene therapy paradigms. We have analyzed a unique Ad vector in an hepatic model of neoantigen transduction utilizing immune-competent mice. Hepatic gene transfer of bacterial β-galactosidase via an Ad vector deleted for both E1 and polymerase activities resulted in extended persistence of the vector genome to greater than two months (experiment duration). In comparison, use of a traditional [E1-] Ad vector encoding the same transgene resulted in a rapid loss of all transduced cells within 1 month of transduction. The extended persistence of the modified vector was substantiated by a number of observations that included: i) extended durations (>1 month) of transduced bacterial Ū-galactosidase enzyme activities in 75–100% of the hepatocytes, ii) an extended duration of transcription (>1 month) from the transgene, and iii) the extended persistence of significant amounts of the vector genome (4.4 vector genomes/hepatocyte) at 28 and 56 dpi. In addition, utilization of the modified vector significantly decreased the hepatotoxicity usually associated with hepatic transduction by Ad vectors, as demonstrated by decreased serum levels of AST at 3 dpi. We also demonstrated that wide-spread persistence of the modified vector genome in hepatic tissues at 28 and 56 dpi actually represented only a fraction of the input vector genomes present at 3 hours post infection (<14%) a result that has been. demonstrated by other groups after Ad vectors are allowed to persist in vivo, ie: Ad mediated transduction of immune-incompetent animals.(Brough et al. (1997) *J. Virol.* 71:9206; Worgall et al., (1997) *Hum. Gene Ther.* 8:37). Finally, each of these improvements were accomplished in adult animals that were neither tolerized to the bacterial β-galactosidase neoantigen, nor treated with potentially toxic agents that nonspecifically blunted the immune system.

Several recent reports have suggested that the immunogenicity of the transgene encoded by Ad vectors is primarily responsible for the transience of Ad vectors in vivo (Chen et al., (1997) *Proc. Natl. Acad. Sci. USA* 94:1645); Clemens et al., (1996) *Gene Ther.* 3:965; Morral et al., (1997) *Hum. Gene Ther.* 8:1275; Lusky et al., (1998) *J. Virol.* 72:2022; Gao et al., (1996) *J. Virol.* 70:8934; Tripathy et al., (1996) *Nature Med.* 2:545). This view is substantiated by the observation that both null Ad vectors and Ad vectors encoding homologous transgenes can persist in immunecompetent animals. (Morral et al., (1997) *Hum. Gene Ther.* 8:1275; Tripathy et al., (1996) *Nature Med.* 2:545; Gao et al., (1996) *J. Virol.* 70:8934). We have therefore specifically chosen to evaluate the ability of the [E1-,polymerase-] Ad vector to transduce the highly immunogenic bacterial β-galactosidase transgene into C57BL/6 mice. Several groups have previously demonstrated that Ad mediated transduction of the bacterial β-galactosidase gene results in a lack of Ad vector persistence (eliminated with one month) in a variety of C57BL/6 tissues. (Morral et al., (1997) *Hum. Gene Ther.* 8:1275; Mcclane et al., (1997) *Pancreas* 15:236; Michou et al., (1997) *Gene Ther.* 4:473; Dedieu et al., (1997) *J. Virol.* 71:4626; Gao et al., (1996) *J. Virol.* 70:8934; Muhlhauser et al., (1996) *Gene Ther.* 3:145; Dematteo et al., (1996) *Gene Ther.* 3:4). The demonstration that a significantly modified [E1-,polymerase-] Ad vector can overcome the barrier to neoantigenic transduction in this model challenges the hypothesis that the transgene is the primary (or only) determinant of Ad vector persistence in vivo. The fact that other modes of gene transfer (such as MV or direct DNA transfer) can also allow for persistence of neoantigenic transgenes (including bacterial β-galactosidase) in immune-competent animals further substantiates this view, independent of our findings.(Xiao et al., (1996) *J. Virol.* 70:8098; Wolff et al., (1992) *Gene Ther.* 1:363)

Recognizing that both vector and transgene encoded epitopes contribute to Ad vector elimination, we hypothesize that there may be two distinct immune responses initiated after Ad mediated transduction, that we will refer to as either "hit#1" or "hit#2". Specifically, first-generation Ad vector-derived gene expression is responsible for "hit#1", while neoantigen expression (after Ad-mediated transduction) in immunecompetent, nontolerant animals is responsible for "hit #2". The simultaneous presence of both "hits" early after Ad vector administration results in a "two-hit" hyperstimulation of the host immune response that results in the complete elimination of all Ad-transduced cells, and in some instances may also break tolerance to self-antigens. (Tripathy et al., (1996) *Nature Med.* 2:545) The "two-hit" hypothesis can therefore accommodate our observation that modified Ad vectors can overcome the immunogenicity of transduced neoantigens, as well as explain why null Ad vectors and Ad vectors encoding homologous transgenes can also persist in immunecompetent animals, since in each of these situations only one "hit" of the "two hits" required to eliminate Ad infected cells are elicited. The "two-hit" phenomenon may be due to several features unique to normal Ad biology, including the recent demonstration that Ad vectors appear to efficiently infect antigen presenting cells (APCs) while AAV based vectors do not (Jooss et al., (1998) *J. Virol.* 72:4212). Finally, this hypothesis does not preclude the possibility that the Ad-vector (hit#1) stimulus may be potent enough to provoke an immune-response to presumably homologous transgenes (in some instances), a situation analogous to the observation that Ad vector transduction can sometimes even break tolerance to self-antigens. (Tripathy et al., (1996) *Nature Med.* 2:545).

EXAMPLE 17

Creation of IVa2 Vector

The C7 adenovirus packaging cell line was created with the use of a portion of the adenovirus genome which not only included the full length polymerase coding region but also included a full length version of the IVa2 gene. In the introduced DNA, the IVa2 gene was also present in such a manner that it was flanked by a potent CMV promoter/enhancer on its 5' end and a polyadenylation signal on the 3' end (Amalfitano, et al., (1997) *Gene Therapy* 4:258–263). Consequently, it was possible that the cell line might also be capable of expressing ample quantities of the IVa2 protein to allow transcomplementation of Ad IVa2 deletion mutants. We have determined that this is in fact the case, by creation of such deletion mutants and growing them to high titer on C7 cells. Therefore it is now possible, according to the methods of the present invention, to create and propagate, without helper virus, Ad vectors containing a IVa2 deletion. Such vectors might also have deletions in E1, polymerase and other deletions discussed herein and still be capable of growth to high titer on the C7 packaging cell line.

To create the Ad IVa2 deletion vector, a deletion was introduced into an adenovirus shuttling plasmid containing essentially nucleotides 0–358 of the adenovirus left end, an AscI site, followed by the adenovirus sequences between map units 9 and 43 of the adenovirus genome. The shuttling plasmid was then re-engineered by deleting out adenovirus DNA sequences that encompass not only the 3' end of the polymerase gene, but also a substantial portion of the IVa2 gene. This was achieved by restriction enzyme digestion and subcloning (effectively eliminating nt 4830–5766 of the Ad5 genome, between AccI and Bst1107I sites) to generate the final shuttling plasmid referred to a pAdAscLΔIVa2, Δpol (FIG. 36). pAdAscLΔIVa2, Δpol contains a 942 bp deletion at about nucleotides 4830 to 5766 and a second deletion of about 608 nucleotides at about nucleotide 7274 to 7881 (as well as deleted E1 and E3 regions), effectively knocking out both IVa2 and polymerase function.

This shuttling plasmid was then co-transfected into the C7 packaging cell lines. Obviously the only way to generate such a virus would be if the packaging cell line produced enough IVa2 gene product to trans-complement the missing IVa2 gene activity in the resultant vector. We isolated such a virus, called [E1-, E3-, IVa2-, pol-]Ad and demonstrated by restriction enzyme digestion that its genome is indeed deleted for the IVa2 region. This virus is a unique vector demonstrating the potential of the cell line to trans-complement any virus that is deleted for the IVa2 regions of genes.

Other deleted adenoviruses carrying deletions in the IVa2 region as well as other deletions can be generated using other shuttle vectors of the present invention by routine modifications of the techniques described above to generate the [E1-, E3-, IVa2-, pol-]Ad.

Shuttle plasmids pAdAscLΔIVa2 (FIG. 19; deletion of about 942 bp at about nucleotides 4830 to 5766 of Ad5 genome in addition to deleted E1 and E3 regions), pAdAscLΔIVa2, Δpp (1.6) (FIG. 36; deletion of about 942 bp at about nucleotides 4830 to 5766, a deletion of about 608 bp at about nucleotides 7274 to 7881, and a deletion of about 955 bp at about nucleotides 8631 to 9585 of the Ad5 genome in addition to deleted E1 and E3 regions), and pAdAscLΔIVa2, Δpp (2.4) (FIG. 37; deletion of about 942 bp at about nucleotides 4830 to 5766, a deletion of about 608 bp at about nucleotides 7274 to 7881, and a deletion of about 2312 bp at about nucleotides 7274 to 9585 of the Ad5 genome in addition to deleted E1 and E3 regions) have been created. These shuttle plasmids are used to create the corresponding deleted adenoviruses using any technique known in the art, for example, the method described above to generate [E1-, E3-, IVa2-, pol-]Ad. The vector [E1-, E3-, IVa2-]Ad is generated from pAdAscLΔIVa2 (this vector also lacks polymerase function). [E1-, E3-, IVa2-, pol-, pTP-(1.6)]Ad and [E1-, E3-, IVa2-, pol-, pTP-(2.4)]Ad are generated from pAdAscLΔIVa2, Δpp (1.6) and pAdAscLΔIVa2, Δpp (1.6), respectively, using routine techniques known in the art or the methods disclosed herein.

It is now possible to increase carrying capacity of adenovirus vectors by simple deletion of the entire IVa2 region of genes. This will significantly increase the versatility of Ad vectors be providing an increased ability to carry larger gene constructs for potential gene therapy applications. Larger gene constructs are desirable since regulatory elements, specific enhancer promoter elements, and/or larger genes can only be accommodated by adenovirus vectors that have sufficient physical carrying capacity.

EXAMPLE 18

100K Deletion

In certain situations even additional transgene carrying capacity is desirable. Further, deletion of genetic material coding for virus specific proteins may further reduce the antigenic profile of the vectors and promote increased in vivo efficacy. One region in which such deletions proved to be possible is known as the 100K region of the adenovirus genome.

This region of the adenovirus genome encodes a protein known as 100K due to its apparent molecular weight when observed in protein electrophoresis gels. The 100K protein encoded by the adenovirus acts as a scaffolding protein during final virion assembly in a host cell. The 100K protein is not incorporated into the final virus particle. Finally, the 100K protein has a number of other functions which includes transport of other viral structural proteins from the cytoplasm into the nucleus of the host cell. This transport function includes the transport of the viral hexon protein. The hexon protein is a major structural subunit of the viral capsid. It has been demonstrated in past literature that lack of 100K activity results not only in lack of detectable 100K protein in infected cells but also destabilization of hexon monomers which results in their rapid degradation in the cytoplasm as well. It is important to recognize that that these previous observations were obtained with the use of hexon (temperature sensitive) mutants. These are mutant viruses that have a single point mutation within the nucleotide sequence of the 100K protein which makes the mutant viruses only viable at 32° C. and mutant at a temperature of 39° C.

The benefits of creating an adenovirus with the 100K gene deleted are multiple. Deletion of the 100K gene increases carrying capacity of resultant vectors that included this deletion significantly, (perhaps up to 10%) translating to approximately an additional 3000 base pairs of carrying capacity in an adenovirus vector. In addition, if 100K deletions can be included in adenovirus vectors that are deleted for other regions of the adenovirus genome as described elsewhere herein. The addition of these additional deletions significantly improves the virus' in vivo gene transfer biological profile. This is because the resultant viral vector that is modified by multiple gene deletions including deletion of 100K has a decreased ability to express multiple viral genes, including lack of expression of the hexon protein secondary to hexon monomer destabilization due to lack of 100K activity. Finally, a vector deleted for 100K has a decreased potential to generate replication competent adenovirus. This is because multiple recombination events would be required to regenerate a wild-type adenovirus. This is in contrast to conventional E1 deleted adenovirus vectors which only require a single recombination event to occur between the adenovirus vector and the resident E1 sequences present in human 293 cells to generate a wild-type adenovirus.

A 100K expressing cell line was constructed by constructing a plasmid containing the 100K coding sequence of adenovirus subcloned between a CMV enhancer promoter element and a polyadenylation sequence to create a 100K transgene cassette. The resulting plasmid pcDNA3+100K (pcDNA3 obtained from Invitrogen Corp.) was linearized by restriction digestion and transfected into human 293 cells using the calcium phosphate transfection technique. The pcDNA3+100K plasmid not only encoded the 100K transgene cassette but also a transgene cassette encoding G-418R resistance. Therefore after transfection cells were exposed to the cytocidal agent G418 and cell clones that were resistant to G418 were subcloned and expanded. These subclones represented cells that had integrated the 100K expressing plasmid into their genome, and were also expressing high levels of the G418 resistance transgene. Approximately 20–25 clones that were G418 resistant were subcloned and propagated.

Subsequently each clone was exposed to a virus known as H5ts116 (obtained from the laboratory of Dr. Ginsburg at the Columbia University). This virus contains a mutation in the 100K gene region that is temperature sensitive. That is the virus only grows to high levels at a temperature of 32° but not at 39°. The 100K temperature sensitive mutant virus was used to screen each of the G418 resistant cell lines as follows. Each of the cell lines was infected with the H5ts116 virus at the non-permissive temperature of 39° C. Theoretically, any cell line which could produce high levels of the 100K protein would allow growth of the mutant virus even at the non-permissive temperature of 39° C. One G418 resistant cell clone referred to as K-16 was found to allow growth of the virus H5ts116 at the non-permissive temperature of 39° C.

Figure 20:
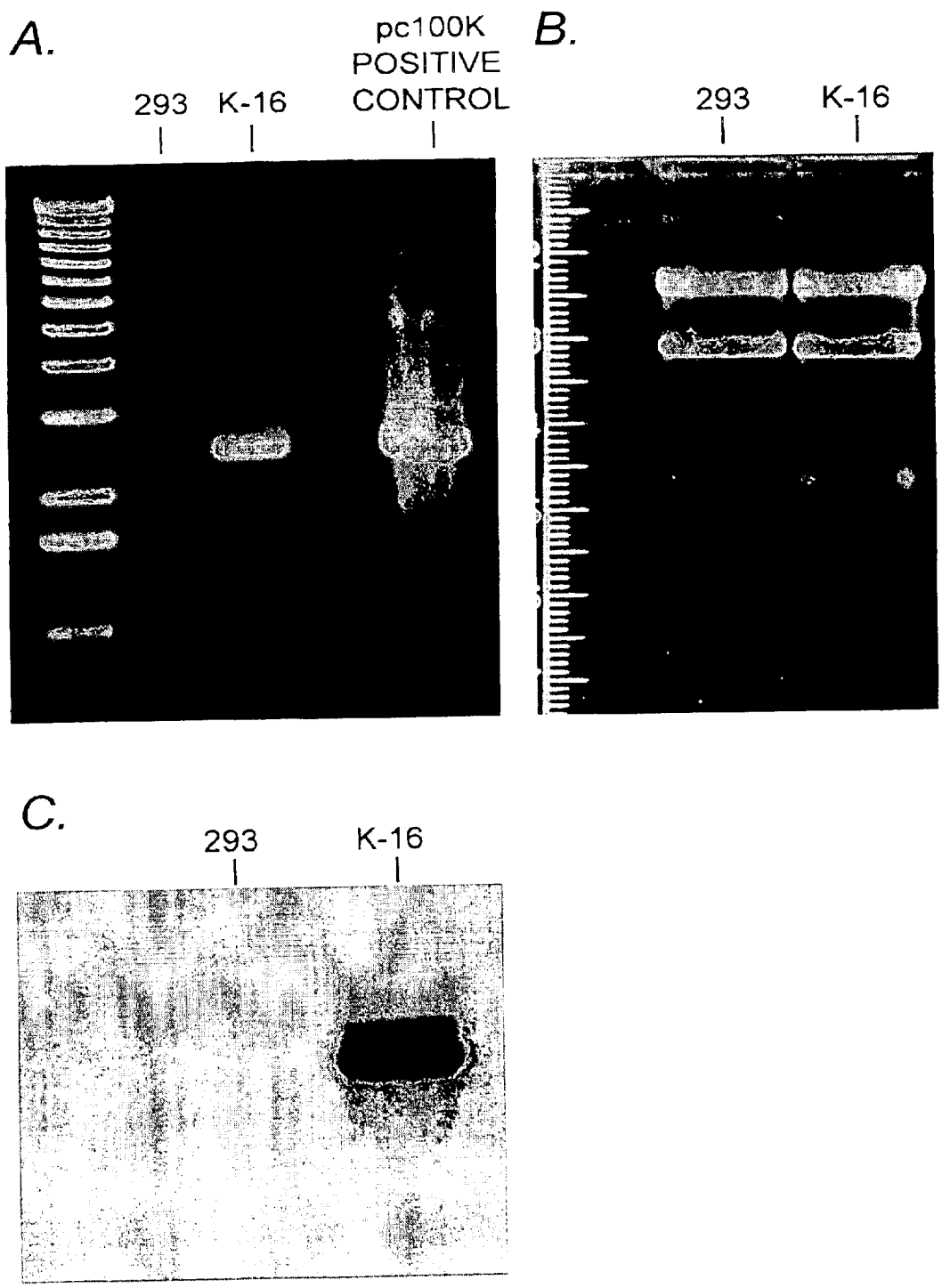
FIG. 20 shows the results of PCR amplification of K-16 and 293 (Panel A) genomic DNA using primers specific to the 100K region. Panel B shows that equivalent amounts of amplified DNA were loaded in each lane. Panel C shows a Northern blot analysis of 293 and K-16 total RNA using a 100K specific probe.

This cell line, K-16, was expanded and investigated more thoroughly. The K-16 cell line had integrated into its genome the 100K sequences confirming that it indeed was capable of expressing a functional 100K protein. In addition, K-16 cells were producing very high amounts of 100K protein specific RNA molecules. This again demonstrated that the cell lines were producing very high levels of 100K and confirmed the cells were capable of growing the virus H5ts116 at non-permissive temperature (FIG. 20). FIG. 20 shows the results of PCR amplification of genomic K-16 DNA using 100K specific primers (Panel A). Equivalent amounts of mRNA from the 293 cell line and the K-16 line were originally electrophoresed and transferred (FIG. 20, Panel B). But as shown by Panel C, only the K-16 cell derived mRNA contained sequences specific for 100K. Panel C shows the presence of the mRNA band in K-16 after probing with a 32-P labeled DNA fragment specific for 100K.

Finally, Table I, below, shows that only the K-16 cell line permits cytopathic growth at the restrictive temperature of adenovirus H5ts116 which contains a temperature sensitive mutation in the gene coding for the 100K protein. In addition, since K-16 was derived from human 293 cells which constitutively produce adenovirus E1 gene products, we have confirmed that the co-expression of the E1 genes and the 100K genes is not cell toxic. This latter fact is advantageous because it allows production according to the methods of the present invention, of a vector that is simultaneously deleted not only for the adenovirus E1 genes but also for the adenovirus 100K genes.

TABLE I

Growth of H5ts116 on K-16 Cells and 293 Cells

| Cell Type | H5ts116 infection @ 32.0° C. | H5ts116 infection @ 39.0° C. |
|---|---|---|
| 293 Cells (E1+) | +++ | 0 |
| K-16 Cells (E1+, 100K+) | +++ | +++ |

Key:
0 = no cytopathic effect;
+++ = all cells undergo cytopathic effect

In addition, we have also introduced the 100K expression plasmid into the C7 packaging cell line which already expresses the E1 gene product as well as the adenovirus polymerase and preterminal protein genes. This adenovirus packaging cell line can simultaneously transcomplement vectors deleted for the E1 polymerase, preterminal protein, IVa2, and 100K gene regions.

Figure 21:
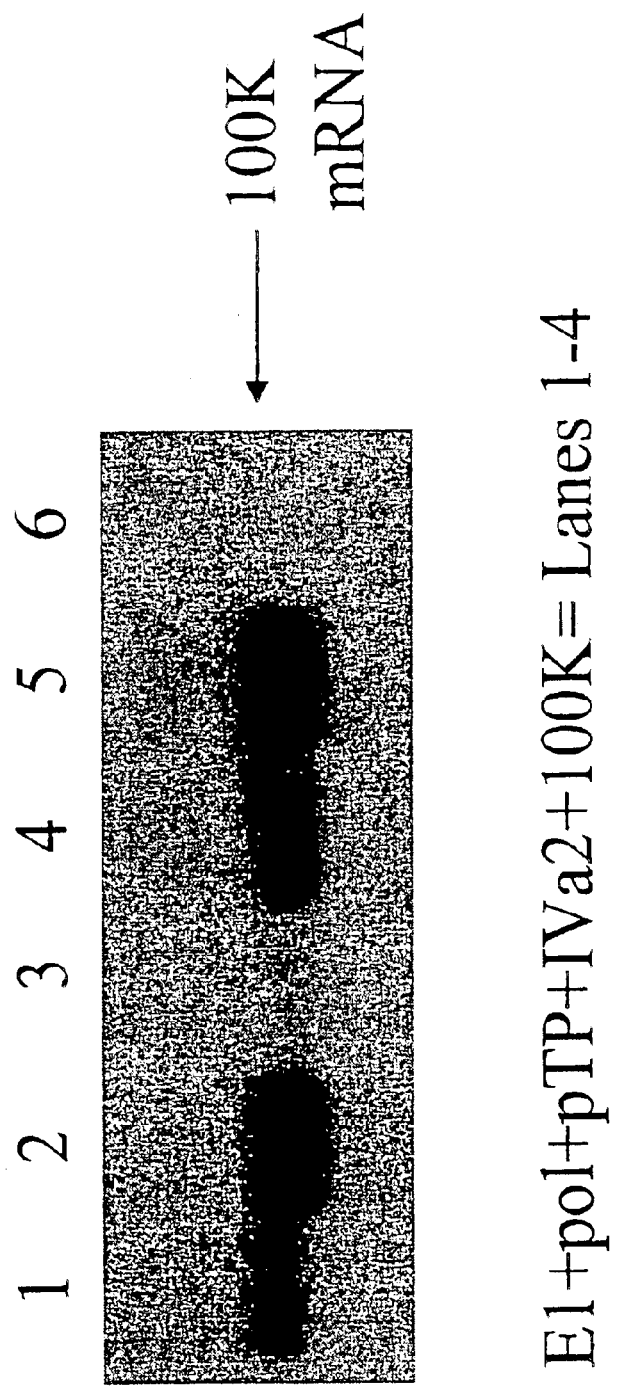
FIG. 21 shows a Northern blot using a 100K specific probe of RNA isolated from C7 cells constitutively expressing the 100K gene (lanes 1–4), as well as a cell line expressing E1 alone (lane 6) or E1 and E1 and 100K (land 5).

We have demonstrated via Northern Blot analyses that we can achieve high level expression of the 100K gene in C7 cells. FIG. 21 shows 32-P labeled 100K DNA probes of cell mRNA from four isolates of C7 cells into which the 100K plasmid was introduced. Each lane represents an individual cell line. Total RNA from each cell line was electrophoresed, blotted and probed with 32-P labeled 100K specific DNA. C7 cells expressing the 100K gene can be used to produce vectors with a combination of E1, Δpol, ΔpTP, IVa2 and/or 100K deletions. Vectors deleted for all of these regions may have improved characteristics for utilization in gene therapy applications since the viruses would have substantially increased carrying capacity, a decreased ability to generate replication competent adenovirus, and finally, an improved in vivo biological profile since they would lack the ability to express multiple viral gene products.

EXAMPLE 19

In Vivo Administration of Ad Δpol Vectors

Ad Δpol Vector Administration: The construction of the modified AdLacZΔpol vector (deleted for both E1 and polymerase activities) as well as Adsub360LacZ, and their high-titer production was as described in Example 1 and 2. Six-8 week old immune-competent C57BL/6 mice (Jackson Laboratory, Bar Harbor, Me.) were intravenously (iv) injected with 200 μl of a PBS solution containing $4 \times 10^9$ β-galactosidase forming units (BFU) of either AdLacZ-sub360 or AdLacZΔpol and subsequently sacrificed at the indicated time points. At least three animals were analyzed pertime point, except animals administered Adsub360LacZ at 56 days-post-infection (dpi), where n=2. All animal procedures and subsequent analyses were performed as approved by the Duke University Institutional Animal Care and Use Committee. Liver and plasma samples harvested from each of the animals were processed as described below.

In-situ Bacterial β-Galactosidase Determination: Liver specimens were embedded in OCT compound, and snap-frozen in liquid-nitrogen cooled isopentane. 10 μm frozen sections were obtained with a Leica cryostat and briefly cross-linked in a 0.5% glutaraldehyde/PBS solution for 5 min. The fixed sections were then placed into 1 mM $MgCl_2$ PBS for 20 min., and incubated overnight at 37.0° C. in a solution containing 5 mM potassium ferricyanide, 5 mM potassium ferrocyanide, 1 mM $MgCl_2$ and 1 mg/ml of the chromogenic X-gal substrate. The stained sections were counterstained with eosin, dehydrated, mounted in Permount, and photographed.

Bacterial β-Galactosidase Activity Determinations: Total protein was extracted from liver tissues by freezing in liquid nitrogen, followed by homogenization in lysis buffer (100 mM potassium phosphate pH 7.8, 0.2% Triton X-100, 0.5 mM DTT) and centrifugation at 14,000 RPM. The protein concentrations in the liver extracts was determined via the BCA protein assay kit (Pierce: Rockford, Ill.). Twenty-five micrograms of protein from each sample was incubated at 37° C. for 1 hour with 1 mM $MgCl_2$, 45 mM β-mercaptoethanol, 0.264 μg of o-nitrophenyl-β-D-galactopyranoside (ONPG), and 50 mM sodium phosphate solution at pH 7.5. The reaction was stopped with 0.5M $NaCO_3$, and the absorbance of each sample was determined at a wavelength of 420 nm. Bacterial β-galactosidase standards (Sigma, St. Louis, Mo.) diluted in lysis buffer were used to generate a standard curve, and the β-galactosidase levels detected in each extract was determined by comparison with the standard curves.

RNA isolation and analysis: Mouse liver total RNA was extracted utilizing the RNA Isolation Kit R-5500 (PGC Scientific, Frederick, Md.) as per the manufacturer's specifications. Approximately twenty micrograms of each RNA sample was separated in a 0.8% formaldehyde-agarose gel, transferred to a nylon membrane, and probed with a [α-$^{32}$P] dCTP-labeled DNA probe capable of hybridizing to bacterial β-galactosidase mRNA transcripts derived from either vector. The probed membranes were washed, and exposed to radiographic film. Densitometric analysis of all exposed films was done with the NIH-Image software package. Quantitative comparison of expression levels was achieved by comparing the ratios of LacZ mRNA detected, to the total RNA loaded (as determined by 18 s rRNA quantitation) for each sample.

DNA isolation and analysis: DNA was extracted as previously described, with some modifications (Amalfitano et al., (1996) Muscle Nerve 19:1549). Briefly, 100 mg of minced mouse liver tissue was mixed with 600 μl of TNES buffer (10 mM Tris-Cl pH 7.5,400 mM NaCl, 100 mM EDTA and 0.6% SDS) and 17.5 μl of proteinase K (20 mg/ml). After overnight incubation at 37° C., 167 μl of 5M NaCl was added and the samples were centrifuged at 14,000 RPM for 10 min. The supernatant was treated with RNase A (5 μg/ml) and extracted with phenol-chloroform. Total DNA was precipitated with 95% ethanol, washed in 70% ethanol, air dried and resuspended in TE buffer. Twenty micrograms of total liver DNA from each mouse were digested with EcoRI, electrophoretically separated in a 0.7% agarose gel, and transferred onto a nylon membrane. Control samples of 20 μg of liver DNA extracted from non-infected animals spiked with either 1 or 10 copies of AdLacZΔpol virus genomes/hepatocyte genome were also included as internal standards. The membrane was crosslinked, and hybridized to a [α-$^{32}$P] dCTP labeled DNA probe (~6 kb EcoRI subfragment of AdLacZΔpol) capable of detecting either vector. The membrane was washed and subsequently exposed to autoradiography films as previously described (Amalfitano et al., (1998) J. Virol. 72:926).

Histopathological studies: Mouse liver tissues were fixed in 10% neutral formalin and embedded in paraffin. 5 μm thick paraffin sections were stained in hematoxylin-eosin, observed under microscope, and representative sections were photographed at equivalent magnifications.

Detection of aspartate aminotransferase (AST): Blood samples from each of the infected mice were harvested via retro-orbital bleeding, and plasma isolated after brief centrifugation. Plasma AST levels were measured in duplicate by using Sigma® AST diagnostic kit 505 according to the manufacturer's specifications. Plasma samples collected from 6 age-matched, uninfected C57BL/6 mice were also analyzed and depicted.

EXAMPLE 20

Figure 22:
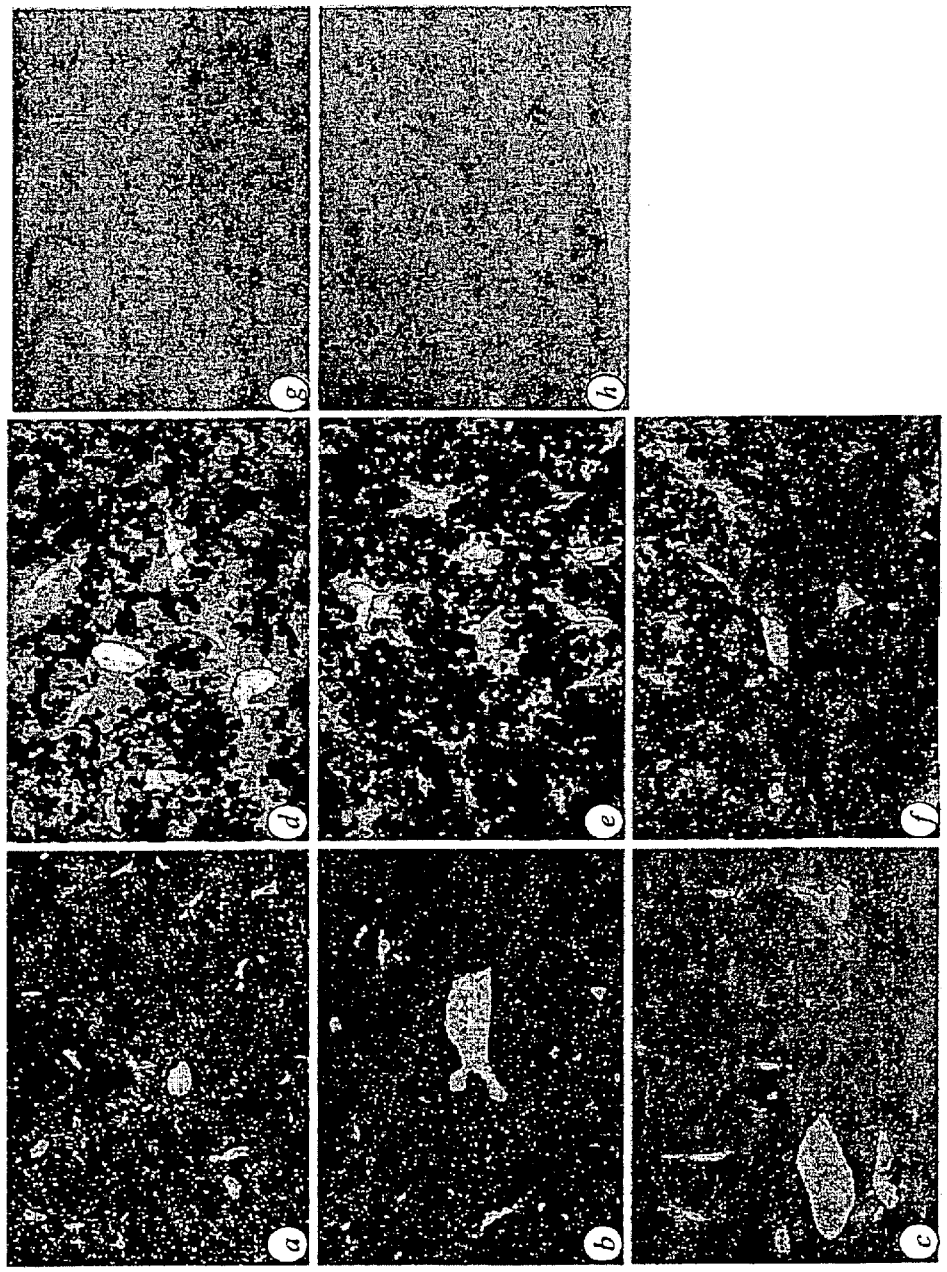
FIG. 22 shows persistence of LacZ neoantigen expression after AdLacZΔpol transduction at various days post infection. Each panel represents an individual animal. Transduction was accomplished with Adsub360LacZ in panels a, c and g and with AdLacZΔpol in panels b, d, e, f and h.

Persistence of Bacterial β-Galactosidase Activity After Hepatic Transduction of Immunocompetent, Nontolerant Mice As described in Example 1, we have isolated a packaging cell line that supports the high level growth of a modified Ad vector ("AdLacZΔpol"—deleted for both E1 and polymerase activities) that encodes the highly immunogenic transgene, bacterial β-galactosidase. The ability of AdLacZΔpol to allow for sustained transduction of bacterial β-galactosidase derived enzyme activity was compared with that of a first-generation, [E1-] Ad vector. C57BL/6 mice are an immune-competent strain of mouse that has been repeatedly demonstrated to be non-tolerant of the bacterial β-galactosidase transgene (see, e.g., Morral et al., (1997) Hum. Gene Ther. 8:1275; McClane et al., (1997) Pancreas 15:236; Michou et al., (1997) Gene Ther. 4:473). After the intravenous administration of $4 \times 10^9$ β-galactosidase forming units (BFU) of Adsub360LacZ (E1 deleted) transduction of nearly 100% of the liver hepatocytes was achieved, as visualized by widespread staining with the X-gal chromogen (FIG. 22, Panel A). Dramatically, by 28 days post-infection (dpi) no X-gal staining cells remained (FIG. 22, Panel C). As expected, the same result was noted at 56 dpi (FIG. 22, Panel G). These results were in agreement with previous reports demonstrating that transduction of C57BL/6 mouse hepatocytes with [E1-] Ad vectors encoding neoantigens are rapidly eliminated within one month of initial administration (see, e.g., Morral et al., (1997) Hum. Gene Ther. 8:1275; McClane et al., (1997) Pancreas 15:236; Michou et al., (1997) Gene Ther. 4:473).

In contrast, an identical infection of C57BL/6 mice with the AdLacZΔpol vector (E1 and polymerase deleted) resulted in high level and wide-spread expression of bacterial β-galactosidase both at 3 dpi (FIG. 22, Panel B) as well as at 28 dpi (FIG. 22, Panels D–F). Each of the latter panels represented individual test animals. Review of multiple sections demonstrated that 75–100% of the hepatocytes were still X-gal stained at 28 dpi, indeed the only cells not stained in the sections were periportal inflammatory cells (see below). This result demonstrated that utilization of the modified Ad vector allowed for an avoidance of the immune responses that normally eliminate most of the cells transduced by Ad vectors encoding neoantigens in immunecompetent animals. However, X-gal staining of AdLacZΔpol transduced livers at 56 dpi demonstrated a lack of X-gal staining in all liver sections in each of the treated groups of animals (FIG. 22, Panel H).

Figure 23:
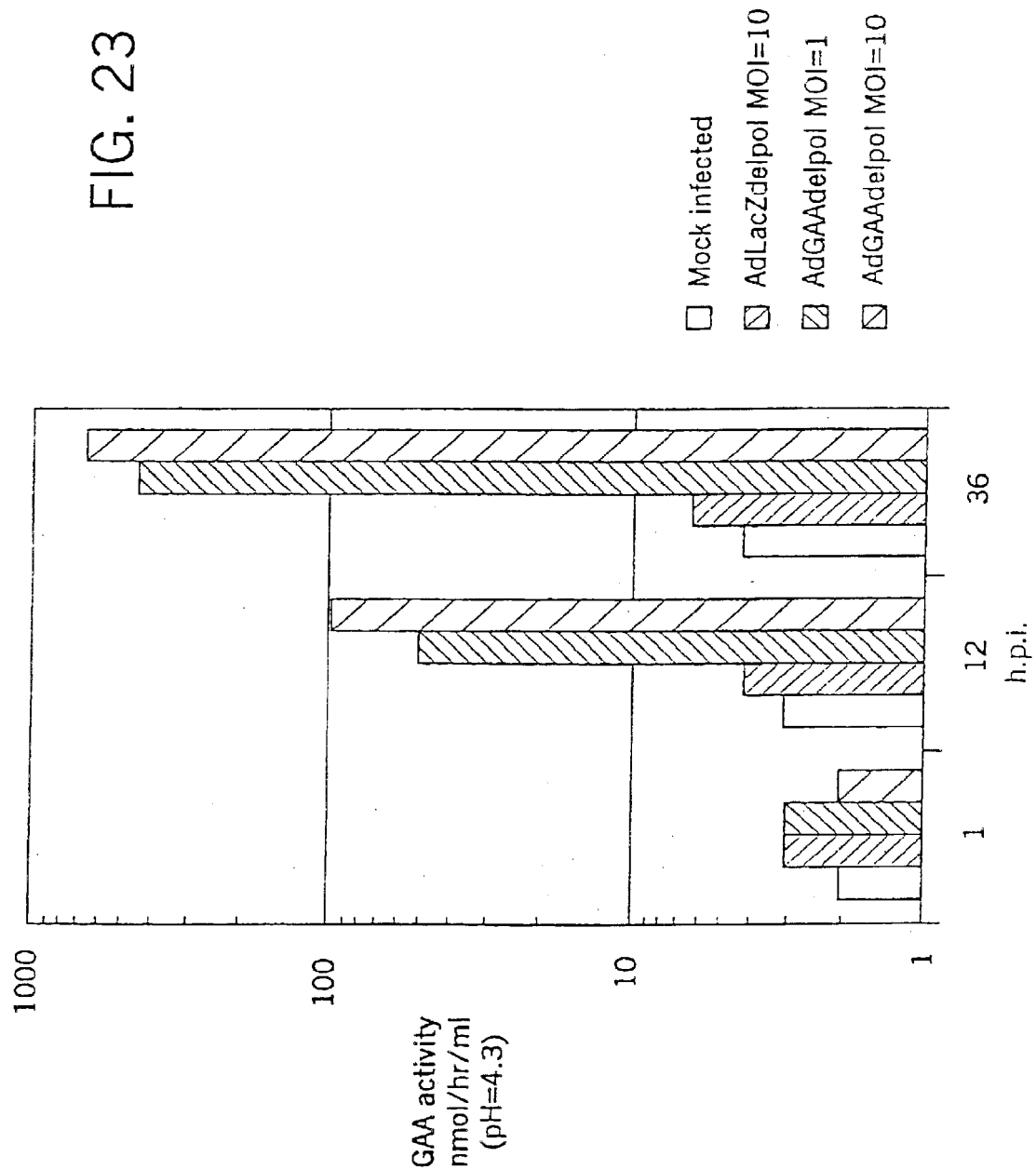
FIG. 23 shows the quantification of bacterial β-galactosidase levels in transduced hepatic tissues after transduction by first generation adenovirus LacZ vectors and Ad LacZ vectors of the present invention.

The X-gal staining data was also quantified by direct measurement of bacterial β-galactosidase activity in liver-derived protein extracts from each of the experimental animal sets (FIG. 23). Again, at 28 dpi substantial amounts of bacterial β-galactosidase activity were detected only with the use of AdLacZΔpol vector. Absolute levels of bacterial β-galactosidase activity had significantly decreased (~92% drop) between 3 and 28 dpi in the AdLacZΔpol treated animals, a decrease that directly correlated with reduced amounts of bacterial β-galactosidase mRNA expression (see below). Furthermore, a lack of bacterial β-galactosidase activity in liver tissues from 56 dpi animals confirmed the previous in-situ results. The lack of expression of bacterial β-galactosidase activity at 56 dpi in AdLacZΔpol treated animals was therefore explored further.

EXAMPLE 21

Figure 24:
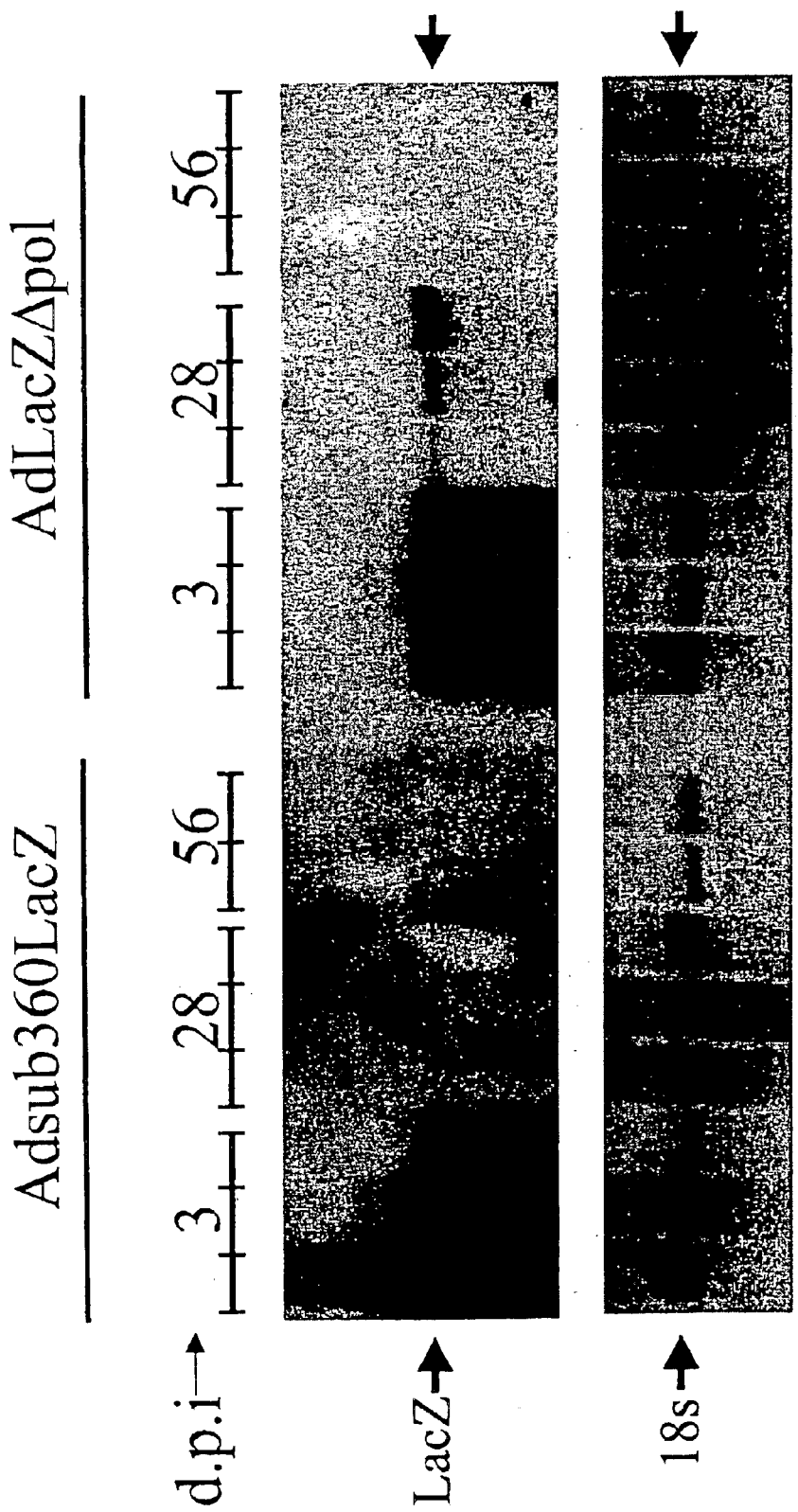
FIG. 24 shows β-galactosidase RNA expression in tissues of animals infected with Adsub360Lac Z or AdLacZΔpol.
Figure 25:
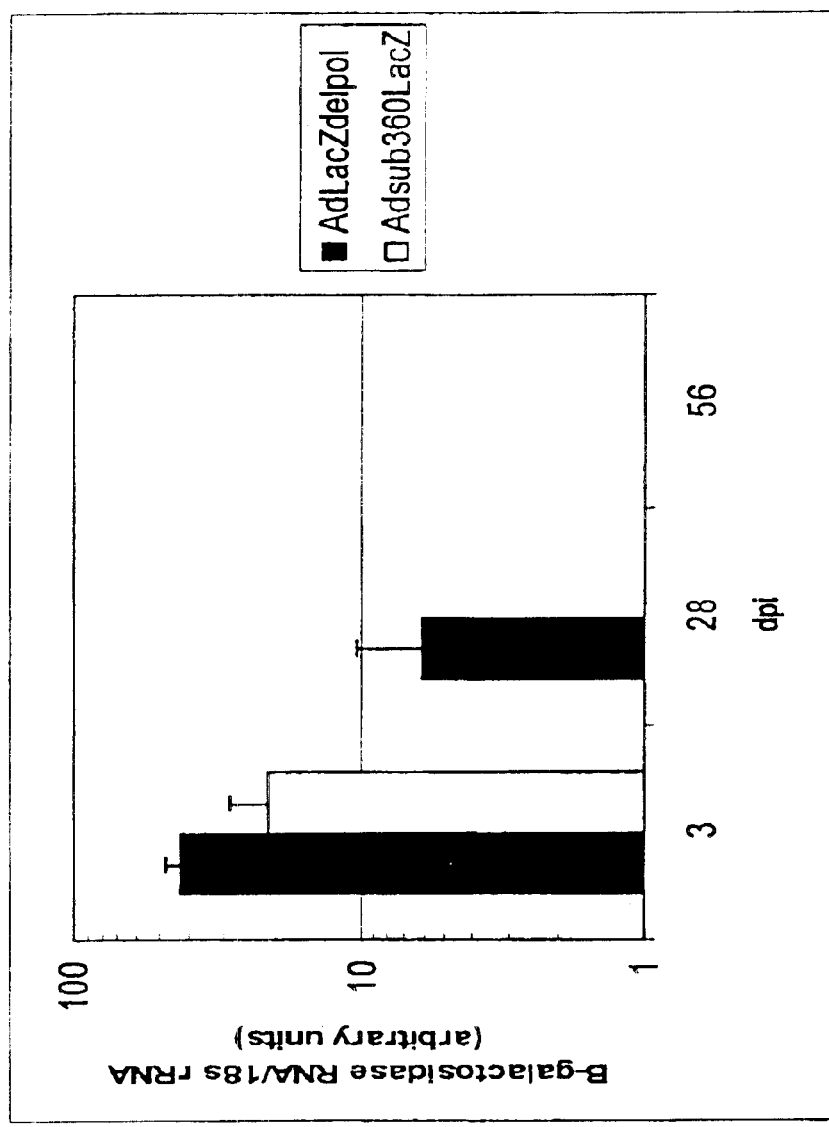
FIGS. 25 represents quantification of β-galactosidase RNA expression in tissues of animals infected with Adsub360LacZ or AdLacZΔpol.

Lack of Transgene Activity at 56 dpi is not Due to a Lack of Modified Vector-Genome Persistence Total RNA extracted from liver sections derived from each of the experimental animals was isolated and analyzed with a bacterial β-galactosidase specific probe (FIGS. 24 and 25). In each animal, lack of X-gal staining correlated with a lack of detectable bacterial β-galactosidase mRNA expression. Specifically, by 28 dpi only AdLacZΔpol treated animals had significant levels of bacterial β-galactosidase specific RNA remaining. Though present, the average amount of bacterial β-galactosidase specific RNA in AdLacZΔpol treated animals at 28 dpi was approximately 86% of the levels noted at 3 dpi, a decrease that correlated with the approximately 92% drop in enzyme activity noted at 28 dpi (FIG. 23). Notably, at 56 dpi AdLacZΔpol treated animals had a complete absence of bacterial β-galactosidase specific RNA, a result that correlated with a complete lack of enzyme activity.

Figure 26:
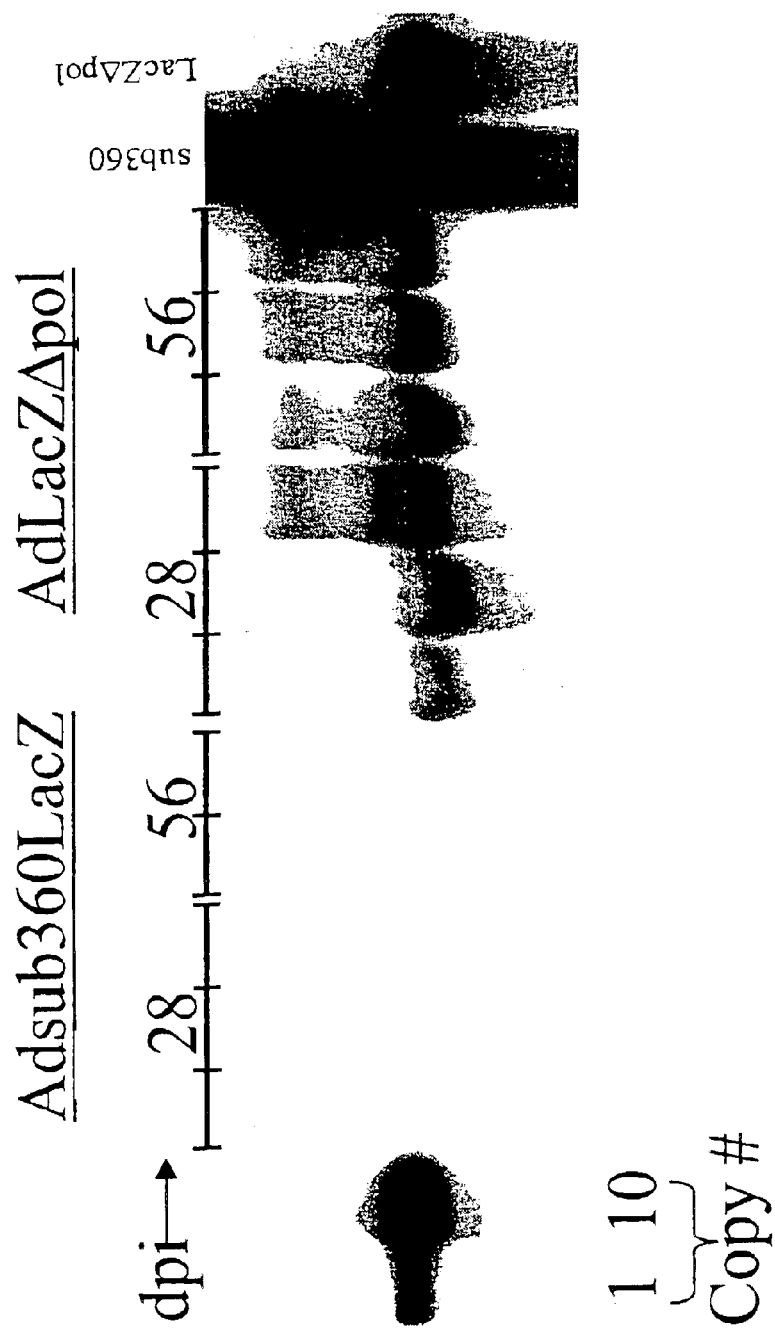
FIG. 26 shows the greater persistence of the vector genome DNA of AdLacZΔpol as compared with Adsub360LacZ.

To determine whether the lack of transgene specific RNA expression at 56 dpi was due to a lack of AdLacZΔpol genome persistence, total DNA was extracted from each of the experimental animals and probed with an Ad specific probe (FIG. 26). As expected, Adsub360LacZ DNA was not detectable at 28 or 56 dpi. However, we were readily able to detect significant amounts of vector specific-DNA sequences in AdLacZΔpol treated animals both at 28 and 56 dpi. Since up to 100% of the AdLacZΔpol transduced hepatocytes were X-gal stained at 28 dpi, the amount of vector DNA detected at 28 and 56 dpi was a reflection of persistent and widespread hepatic transduction. Consequently the rapid loss of X-gal staining, bacterial β-galactosidase enzyme activity, and bacterial β-galactosidase mRNA expression at 56 dpi was not due to a lack of vector persistence, but was rather due to a lack of transgene derived RNA expression from the persistent vector genomes. Quantitation by densitometry demonstrated that the absolute levels of vector DNA detected both at 28 and 56 dpi averaged ~4.4 copies of the AdLacZΔpol genome per hepatocyte, a result consistent with the widespread X-gal staining data presented in FIG. 22, Panels D–F. Interestingly, this DNA represented at most 14% of the input vector DNA noted at 3 hours post-infection (data not shown), a result consistent with previous observations in immune-incompetent mice. The latter studies have demonstrated that a significant amount of input Ad vector genomes are cleared by innate mechanisms present in the liver within 24 hours of infection, independent of immune responses directed to the vector or transgene. (Brough et al., (1997) *J. Virol.* 71:9206; Worgall et al., (1997) *Hum. Gene Ther.* 8:37).

EXAMPLE 22

Inflammatory Responses to Modified Ad Vectors

Figure 27:
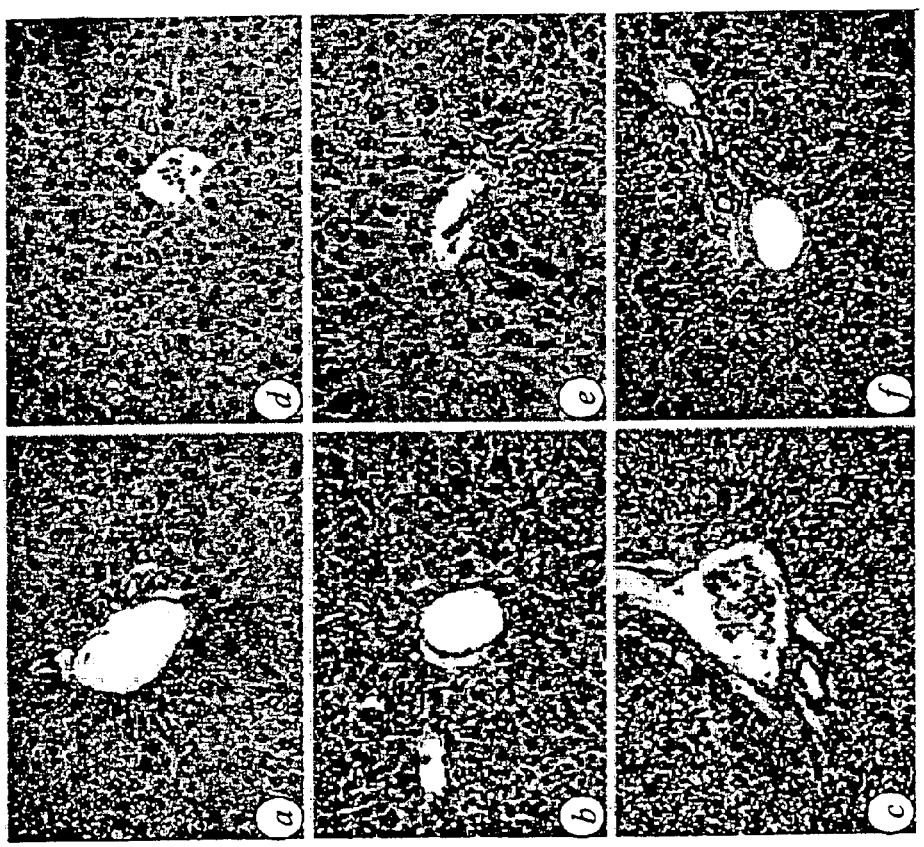
FIG. 27 shows levels of inflammation after hepatic transduction with either Adsub360LacA or AdLacZΔpol by haemotoxylin and eosin stained sections. Panels a, b and c are Adsub360LacZ infected mice. Panels d, e and f are from AdLacZΔpp infected mice.
Figure 28:
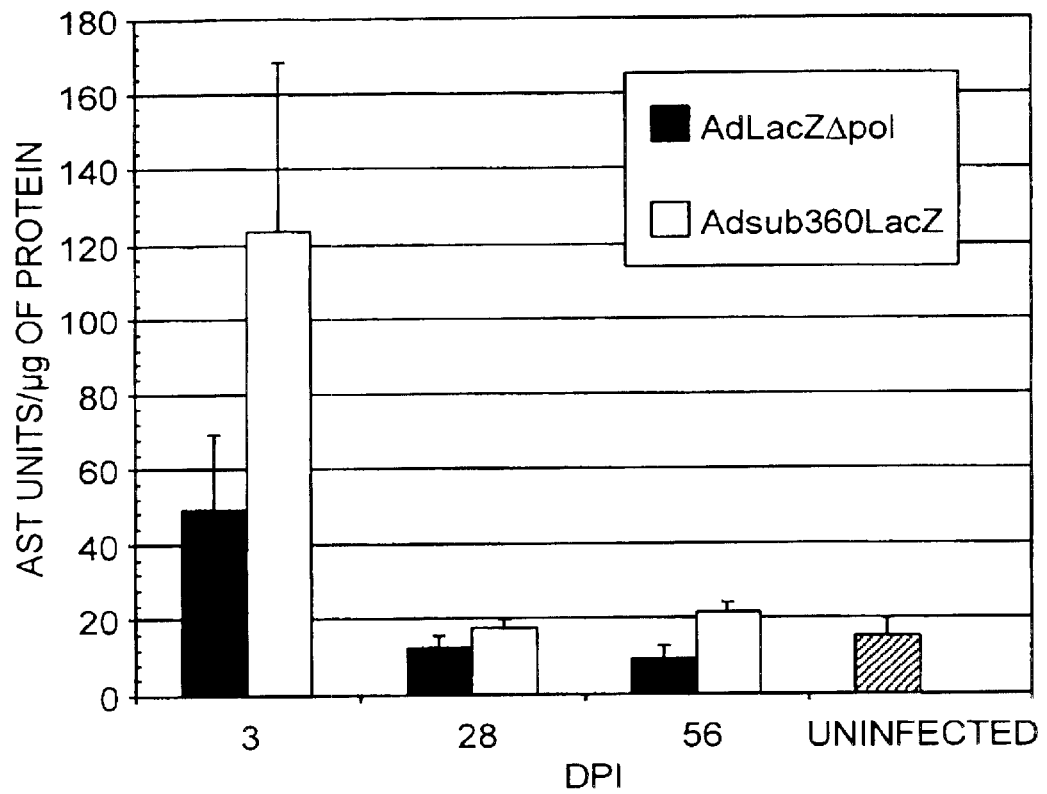
FIG. 28 shows plasma aspartate aminotransferase (AST) analysis of hepatic cells of the mice which had been administered Adsub360LacZ or AdLacZΔpol vectors, reflecting decreased AST levels in the Δpol vector as compared to the first generation vector.

Histopathological evaluation demonstrated that a significant cellular-inflammatory infiltrate was evident in both sets of treated animals by 28 and 56 dpi (FIG. 27). Since both vectors elicit similar reactions at 28 and 56 dpi, the inflammatory infiltrates may have been directed to stimuli common to both vector preparations. The infiltrates contained lymphocytes, macrophages, and occasional plasma cells. In contrast, at 3 dpi, levels of serum AST (released by damaged hepatocytes) were significantly less (p=0.01) in AdLacZΔpol treated animals than in animals infected with the first-generation Ad vector (FIG. 28). After 28 dpi, however, both experimental animal sets returned to base line serum AST activities. It was significant that at 3 dpi, the decreased serum AST levels noted after AdLacZΔpol hepatic transduction positively correlated with the lack of elimination of AdLacZΔpol transduced hepatocytes noted at 28 and 56 dpi.

EXAMPLE 23

Isolation of the GAA Transgene

The acid α-glucosidase full length cDNA (Hoefsloot, L. H. et al. (1988) EMBO Journal 7, 1697–1704), was excised with EcoRI from the pSHAG2 vector (Hoefsloot, L. H. et al. (1990) Biochem. J. 272, 485–492), isolated on an agarose gel, and ligated into the multicloning site of the widely used and commercially available mammalian expression vector pcDNA3 (Invitrogen, San Diego, Calif.). Because EcoRI is used as a cloning site there are two possible ligation products, with opposite orientations. The plasmid which has the GAA transcription in the direction under the control of the CMV promoter was selected by restriction enzyme digestion according to the predicted map. The resultant plasmid was called pcDNA3-GAA and contains the CMV promoter.

The cDNA was also cloned as a polycistronic construct in the EcoRI restriction site of the pMT2 vector (Kaufman, R. J., (1990) *Methods Enzymol.* 185, 537–566; Kaufman, R. J., (1990) *Methods Enzymol.* 185, 487–511), and called pMT2-GAA. A 1714 base pair fragment containing the DHFR gene under the control of the adenovirus major late promoter, the TPL (adenovirus tripartite leader) the intervening sequence (IVS) and the SV40 poly A site, but not the SV40 enhancer, was excised by BamHI, and isolated on an agarose gel. This fragment was ligated into the compatible BglII restriction site of the pcDNA3-GAA plasmid. In this selected plasmid, called pJW55, the orientation of the transcription of GAA and of DHFR is the same.

A 567 bp fragment of the GAA cDNA, starting from 18 bp 5' of the ATG start codon and ending 529 bp into the coding sequence of acid α-glucosidase, was prepared by PCR amplification using the sense oligonucleotide primer GAA224(+) TCC AGG CCA TCT CCA ACC AT (SEQ ID NO: 1) and the antisense oligonucleotide primer GAA751 (−)TCT CAG TCT CCA TCA TCA TCA CG (SEQ ID NO:2). This fragment contains the natural SacI site of the GAA cDNA which site occurs 320 bp into the acid α-glucosidase coding sequence. The 567 bp fragment was ligated into the pCRII plasmid using the TA cloning technique and following the instructions of the supplier (Invitrogen, San Diego, Calif.). This results in two possible cloning products with opposite orientations. We chose the one that has the GA224(+) site close to the HindIII site of the original PCRII plasmid. This plasmid is called pCRII-1. The orientation and the DNA sequences were confirmed by DNA sequencing and restriction enzyme digest mapping. pCRII-1 contained the HindIII site 5' relative to the ATG start codon as well as the natural SacII site at 320 bp into the coding sequence of acid α-glucosidase.

Following digestion of pCRII-1 with both HindIII and SacII, a fragment containing nucleotides 892–1496 is isolated on agarose gel. This fragment contains the nucleotides 279–670 of the original GAA cDNA. The ASCII site is 314 nucleotides downstream of the ATG start site. The HindIII site is derived from the multiple cloning site of the original plasmid vectors pCRII and pcDNA3.

The pcDNA3-GAA vector is similarly digested with both HindIII and ASCII, and the large plasmid fragment isolated on agarose gel. The small fragment contains the beginning of the acid α-glucosidase gene, including the entire untranslated sequence prior to the ATG start codon and extending through the 3' end of the SacII cleavage site, which is bp 670 of the gene sequence. This small fragment is discarded. The large fragment contains that portion of the acid α-glucosidase gene sequence beginning on the 5' end of the SacII cleavage site at bp 671 and extending through the final bp of the gene which remains attached to the plasmid backbone.

The fragment containing nucleotides 279 through 670 of the original GAA cDNA isolated from the pCRII-1 digestion is now ligated into the large plasmid fragment isolated from the pcDNA3-GAA digestion, creating the plasmid vector pcDNA3–5'sGAA, which contains the 5' shortened version of GAA.

A fragment (nucleotides 898–4439) containing this newly created shortened cDNA is excised from pcDNA3–5'sGAA by digestion with the restriction enzymes KpnI and XhoI. In pJW55 the full-length GAA cDNA insert is removed by digestion with KpnI and Xho1 (nucleotides 2611–6355), and the plasmid backbone isolated on agarose gel. The shortened cDNA isolated from pcDNA3–5'sGAA is then ligated into the compatible Kpn1-Xho1 sites of this plasmid backbone creating pJW-5'sGAA. Both Kpn1 and Xho1 sites are derived from the original pcDNA3 plasmid multiple cloning site and are unique in both pJW55 and pcDNA3–5'sGAA. The resulting pJW-5'sGAA plasmid has the 5' shortened non-translated sequence of GAA under the CMV promoter as well as the DHFR gene under the adenovirus Major Late promoter. The cDNA insert starts at nucleotide 2611 and ends at nucleotide 6153.

EXAMPLE 24

Creation of Ad Vector with hGAA Transgene

Plasmid pcDNA3GAA was digested by XmnI, and the approximately 4.5 kb fragment containing the transgene cassette was blunt ended with T4 DNA polymerase and subcloned into the shuttling plasmid of the present invention, pAdAscLΔpol (Example 2) which is designed for the construction of Ad vectors deleted for the E1, E3 and polymerase gene functions. The resulting plasmid pAdAscLΔpolhGAA was co-transfected via the calcium phosphate technique (Jones et al. (1978) Cell 13:181; Mittereder et al., (1996) J. Virol. 70:7498) into the adenovirus packaging cell line C-7, simultaneously with XbaI, ClaI and ScaI digests of adenovirus virion DNA from dl7001. Recombinant vector clones were expanded and confirmed to contain the hGAA gene by restriction enzyme digestion of vector derived DNA (Jones et al. (1978) Cell 13:181), as well as by multiple functional analyses (see Examples below). Cesium chloride purified AdhGAAΔpol vector was produced after infection (MOI was ~10) of 60, 150 mm tissue culture plates containing C-7 cells (expressing the adenovirus E1, polymerase, and preterminal protein). All vector titers were confirmed by plaque forming unit (PFU) assay of serial dilutions of the vector preparations of C-7 cells.

EXAMPLE 25

In Vivo Administration of AdhGAAΔpol

Intravenous Administration: 1×10$^9$ pfu of AdhGAAΔpol vector was intravenously administered (via the retro-orbital sinus) into 6.5-month-old C57BL/6 (wild-type) mice or 2-month-old GAA-KO mice ($6^{neo}/6^{neo}$). (Clemens et al., (1996) Gene Ther. 3:965). At the respective time points post-injection, plasma or tissue samples were obtained and processed as described below. All animal procedures were done in accordance with the Duke University Animal Care and Use Committee guidelines.

Measurement of Tissue/Plasma GAA Activity and Glycogen Accumulation: Tissues were snap frozen in liquid nitrogen, homogenized in water, and insoluble proteins were removed by centrifugation. The protein content of the resultant lysates was quantified by the Bradford assay. For plasma GAA activity detection, blood samples were collected by retro-orbital sampling into heparinized capillary tubes, followed by plasma isolation. GAA activity in each of the tissues or plasma was assessed by measurement of 4-methylumbelliferyl-α-D-glucoside cleavage at pH 4.3, as previously described (Amalfitano et al., (1997) Gene Ther. 4:258). Glycogen content was determined by treatment of tissue extracts with A. niger amyloglucosidase and measurement of glucose released. All extracts were also assessed for background glucose release, i.e., in the absence of the A. niger amyloglucosidase. Final glycogen content values were then determined after untreated glucose levels were subtracted from the glucose content of each of the amyloglucosidase treated tissue extracts (n=4 for C57Bl/6 mice, n=3 for GAA-KO mice, n=3 for Ad treated GAA-KO mice).

Morphological Assessment of Tissues: Sections were placed in embedding compound and snap frozen in liquid nitrogen-cooled isopentane. Ten micron sections of the tissues were collected with a Leica cryomicrotome, PAS stained, and visualized with a Leica microscope and digital camera.

RNA Analysis: Total RNA was isolated from portions of mouse tissues after homogenization in 4.0 M guanidinium thiocyanate and cesium chloride purification. 12.5 μg of total RNA from each tissue was electrophoretically separated in a 1% formaldehyde-agarose gel, blotted onto a nylon membrane, UV crosslinked, and probed with a $^{32}$P-labelled 3.3 kb fragment containing the hGAA cDNA. The probed membranes were washed, exposed to autoradiographic film, and photographed.

Immunoblot Detection of hGAA: Respective mouse tissues were frozen, homogenized, centrifuged to remove insoluble proteins, and protein content of the supernatants was measured by the Bradford assay. Equivalent amounts of protein were electrophoretically separated in a 10% polyacrylamide-SDS gel, transferred to a nylon membrane, and probed with a rabbit anti-human GAA polyclonal antibody. Detection of the bound anti-hGAA antibody was visualized with the ECL detection system (Amersham). For direct detection of hGAA precursor in plasma, 2.5 μL of each sample was electrophoretically separated, followed by anti-hGAA antibody probing of the immunoblot as described above.

EXAMPLE 26

Construction of the AdhGAAΔpol Vector—Results

Figure 29:
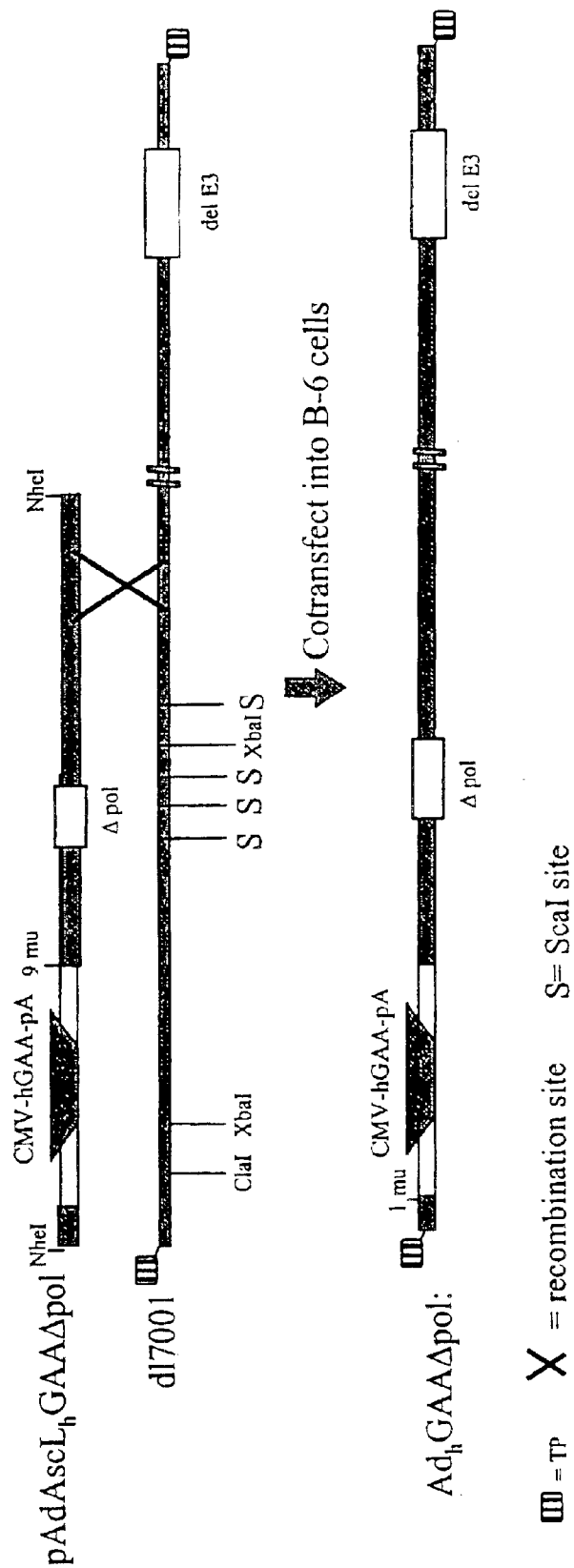
FIG. 29 shows the construction of the AdhGAAΔpol vector.
Figure 30:
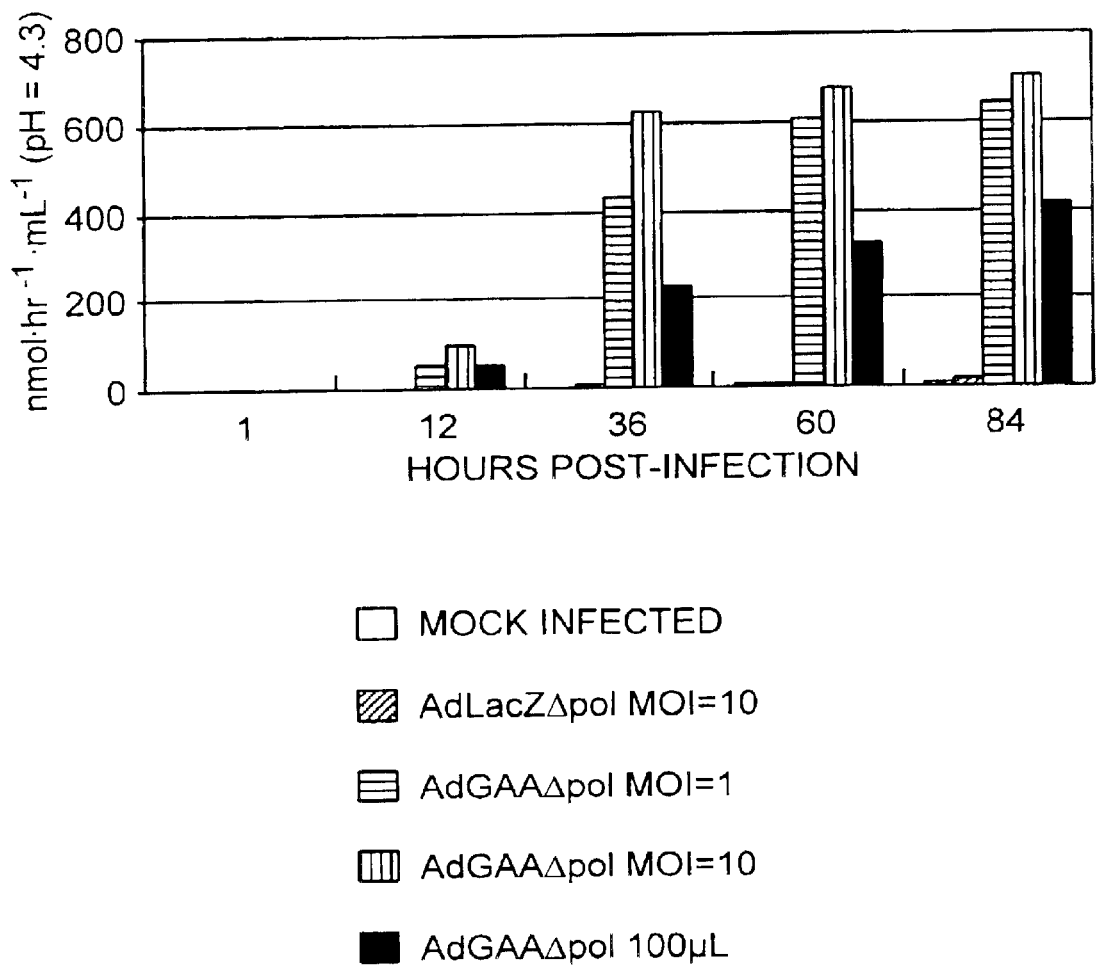
FIG. 30 shows hGAA activities after infection of 293 cells with AdhGAAΔpol.

The production and clonal purification of modified Ad vectors deleted for both the Ad E1 and polymerase genes has previously been described (Jones et al. (1978) Cell 13:181). These vectors have the ability to allow for prolonged persistence after hepatocyte infection, despite neoantigen gene transfer (Ilan et al., (1997) Proc. Natl. Acad. Sci. USA 94:2587). The construction of the AdhGAAΔpol vector was carried out as described in Example 24, and is depicted in FIG. 29. Restriction enzyme mapping of DNA derived from the purified vector confirmed that it contained the CMV-hGAA transgene cassette (data not shown). Further analysis demonstrated that the AdhGAAΔpol vector was capable of high level expression of the hGAA enzyme activity (as assessed by cleavage of 4-methyl-umbelliferyl-α-D glucoside) after infection of cultured human 293 cells (FIG. 30). Importantly, the supernatant overlying the infected human cells accumulated increasing amounts of hGAA activity with time, suggesting that AdhGAAΔpol infection resulted in both high level expression and sustained secretion of an active hGAA enzyme.

EXAMPLE 27

Hepatic Targeting of the AdhGAAΔpol Vector and GAA Secretion

Figure 31:
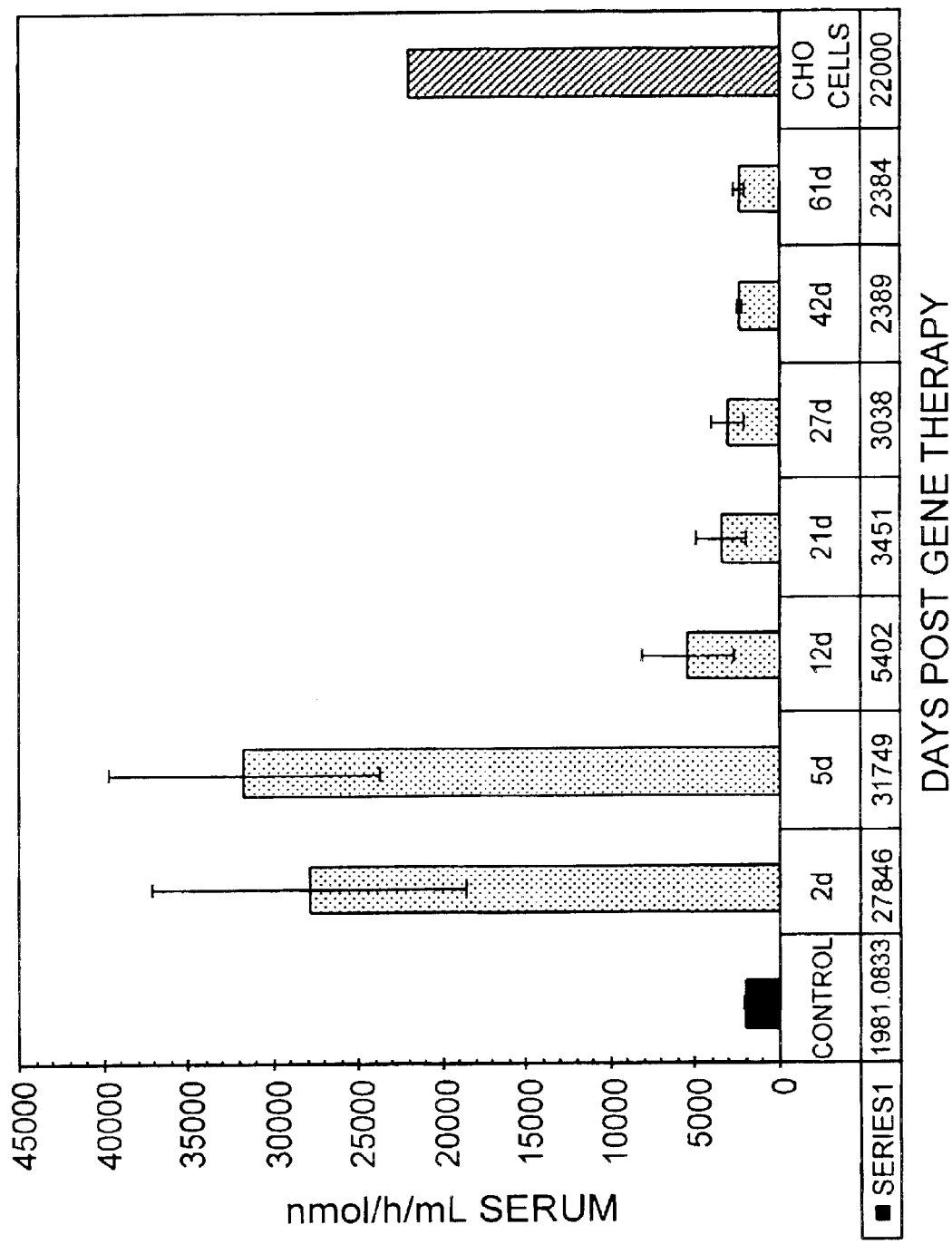
FIG. 31 shows hGAA enzyme levels after AdhGAAΔpol infection of c57BI/6 mice (wild type).

Ad vectors preferentially transduce hepatocytes after intravenous administration. The hypothesized model for GSD-II treatment that capitalizes upon hepatic targeting of Ad vectors was investigated as follows: High level production and secretion of hGAA in the plasma was demonstrated after the intravenous injection of $1 \times 10^9$ plaque forming units (pfu) of AdhGAAΔpol into wild-type mice (FIG. 31). Extremely high levels of GAA activity were detected in the plasma as early as two days after infection, although the levels diminished with time. In hepatocytes, a rapid down-regulation of CMV enhancer activity occurs, and may have contributed to the decreased GAA activities detected in the plasma, although production of murine antibodies to the human enzyme may have also been present. (Ilan et al., (1997) Proc. Natl. Acad. Sci. USA 94:2587; Kaplan et al., (1997) Hum. Gene Ther. 8:45; Kay et al., (1995) Nat. Genet. 11:191).

Figure 32:
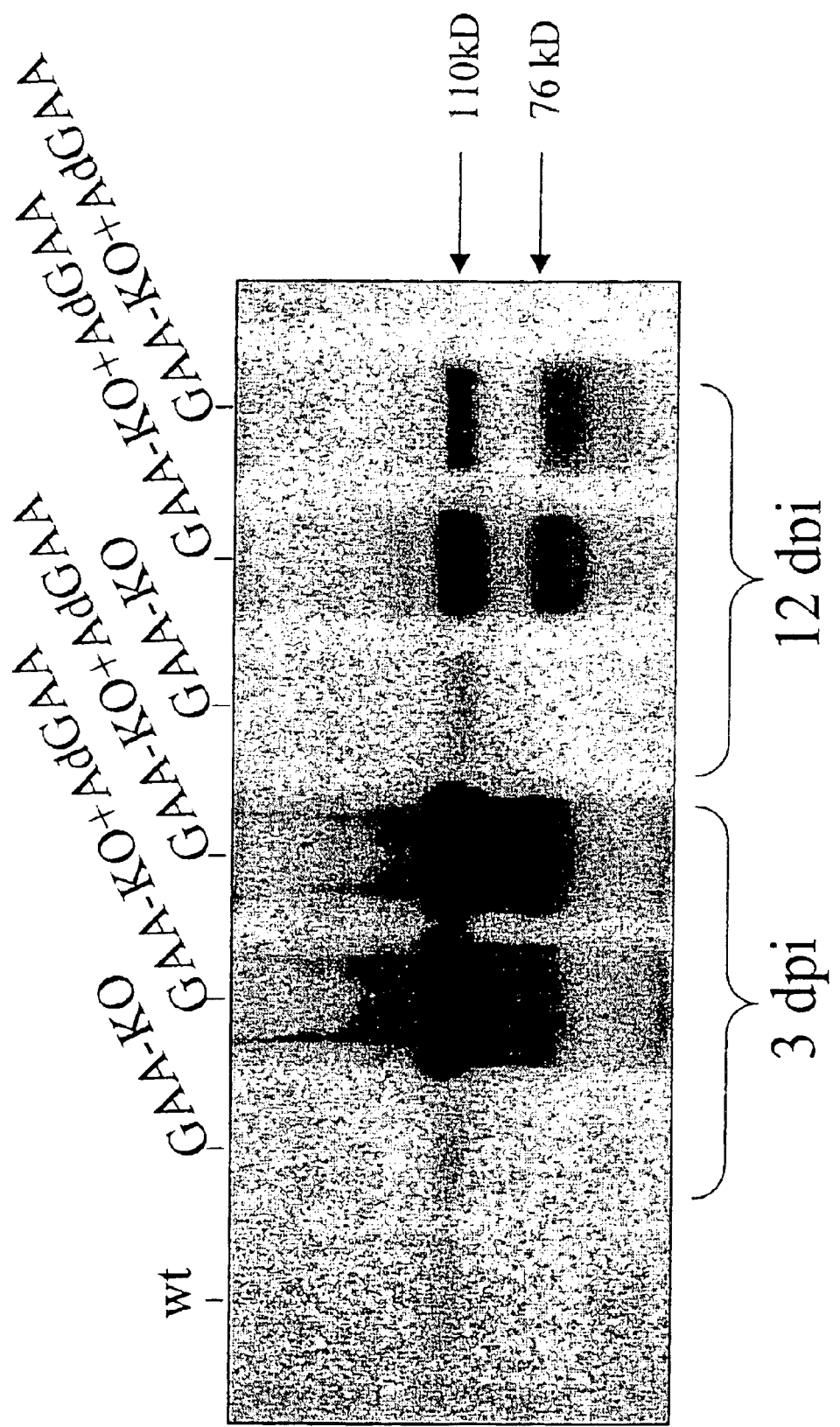
FIG. 32 shows hGAA immunoblot detection of various isoforms of GAA after infection of GAA knockout (KO) mice with AdhGAAΔpol.

Intravenous injections of the AdhGAAΔpol vector into the GAA-KO mouse were also done to ascertain the effectiveness of the secreted hGAA to reduce glycogen accumulations in affected skeletal and cardiac muscle. The GAA-KO mouse was previously generated by targeted knockout of the murine GAA gene and has a phenotype that includes systemic glycogen accumulations in the cardiac and skeletal muscles, as well as progressive clinical myopathy. (Clemes et al., (1996) Gene Ther. 3:965). After intravenous injection of the AdhGAAΔpol vector, high levels of enzyme activity were demonstrated in the plasma of the GAA-KO mice (FIG. 32). Importantly, protein immunoblot analysis of plasma demonstrated that the predominant form of hGAA detected in the treated animals at 3 days post infection (dpi) had a molecular weight of ~110 kD, a size equivalent to the precursor (unprocessed) form of hGAA (FIG. 32) (Kochanek et al., (1996) Proc. Natl. Acad. Sci. USA 93:5731). In addition, a significant amount of the processed from of the enzyme (~77 kD) was also detected in the plasma. This may be the result of proteolysis of the mature GAA in the plasma, or release of the mature form of hGAA from infected hepatocytes.

EXAMPLE 28

Assessment of hGAA Distribution in the GAA-KO Mouse

Figure 33:
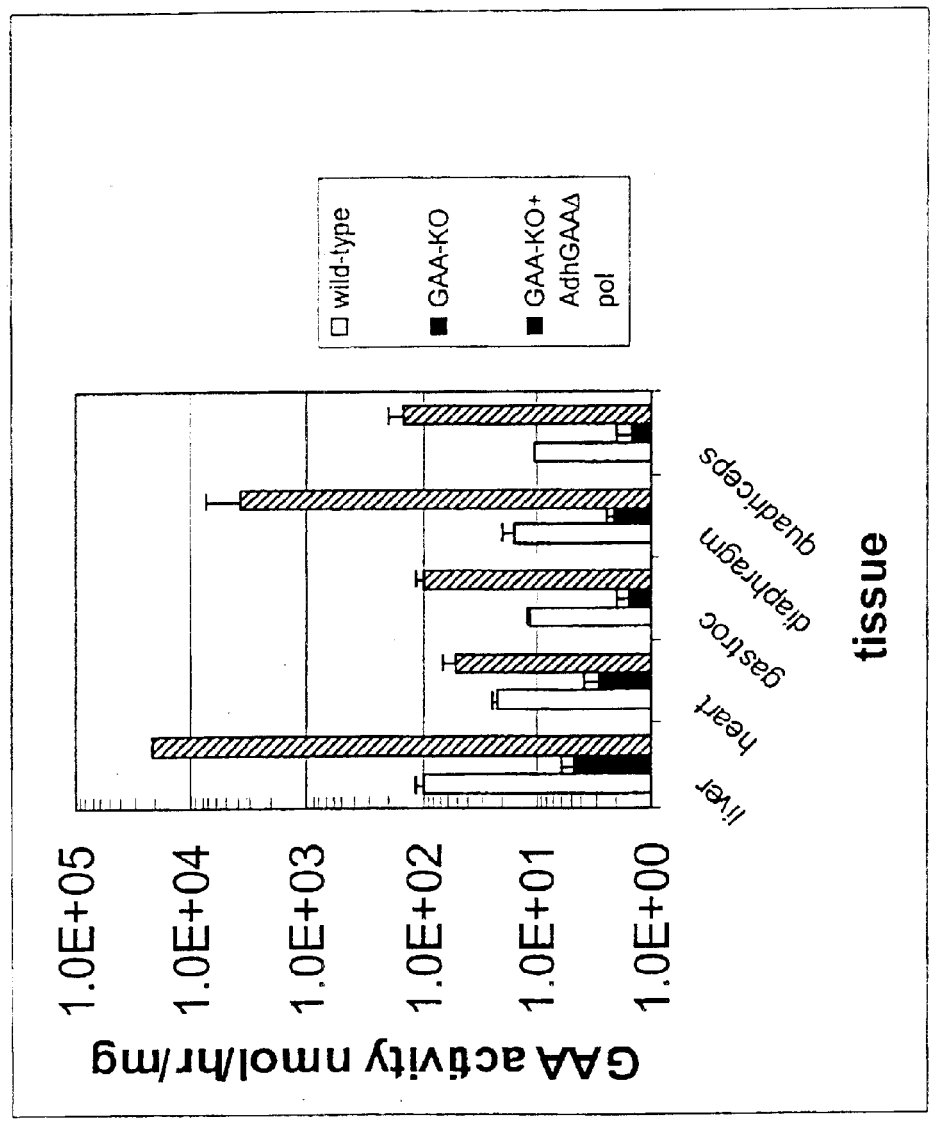
FIG. 33 shows GAA activity in various tissues of GAA knockout mice 12 days after treatment with AdhGAAΔpol.
Figure 34:
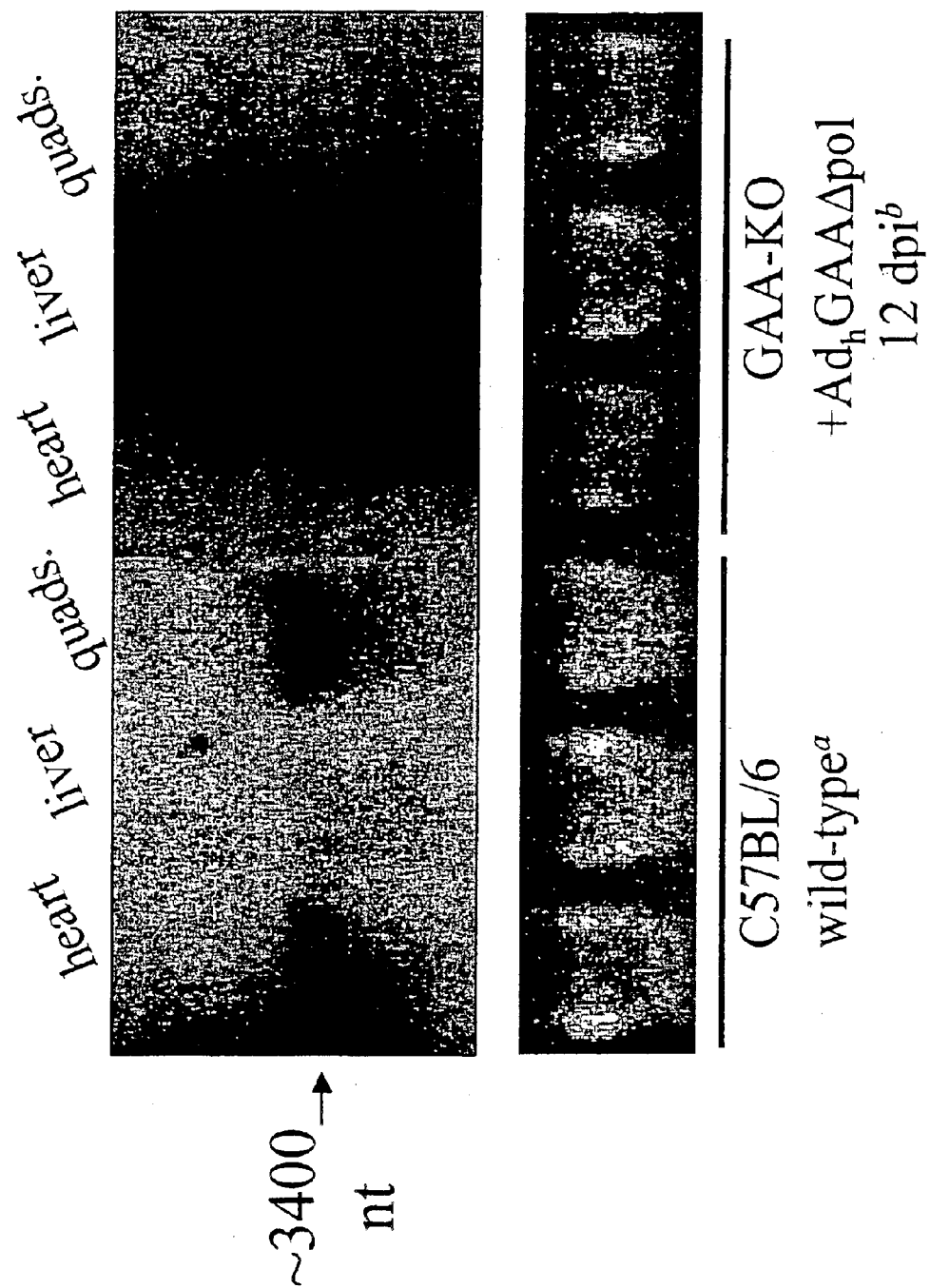
FIG. 34 shows a Northern blot analysis of RNA isolated from various tissues from wild-type and GAA-KO animals administered AdhGAAΔpol at 12 days d.p.i using a GAA-specific probe.

After treatment with the AdhGAAΔpol vector, GAA-KO animals were sacrificed and tissues were analyzed for the presence of GAA activity. A pilot study demonstrated that at 4 dpi GAA activity was detected in multiple muscle tissues of AdhGAAΔpol treated GAA-KO mice, but glycogen levels had only minimally begun to decrease (data not shown). By 12 dpi GAA activity levels in the quadriceps, gastrocnemius, diaphragm, and cardiac muscles of the Ad treated GAA-KO animals were all significantly elevated when compared to the enzyme levels detected in untreated GAA-KO mice (FIG. 33). Even more dramatically, the muscle GAA enzyme activity levels detected in the treated animal exceeded those detected in wild-type mice (FIG. 33) to confirm that the GAA activity detected in the muscles of treated animals was not due to de novo biosynthesis of GAA in the muscles, RNAs derived from various tissues were also analyzed (FIG. 34). Despite the fact that the heart and quadriceps muscles of AdhGAAΔpol treated GAA-KO mice contained high levels of GAA activity, GAA specific RNA transcripts were detected only in the liver, and not in either of the muscle tissues. Note that in a wild-type mouse, GAA mRNA was readily detected in muscle tissues, despite the fact that the enzyme activities in these tissues were lower than in the AdhGAAΔpol treated animal. Immunoblot analysis of protein extracts derived from the liver, cardiac, and quadriceps muscles of the Ad treated GAA-KO mice also demonstrated that the liver had high levels of the precursor form of hGAA present, while the cardiac and quadriceps muscles did not (data not shown). Based upon these observations, we concluded that the enzyme activities detected in the muscle tissues of the AdhGAAΔpol treated animals was most likely derived exogenously, i.e., via uptake of precursor GAA secreted by the liver.

EXAMPLE 29

Figure 35:
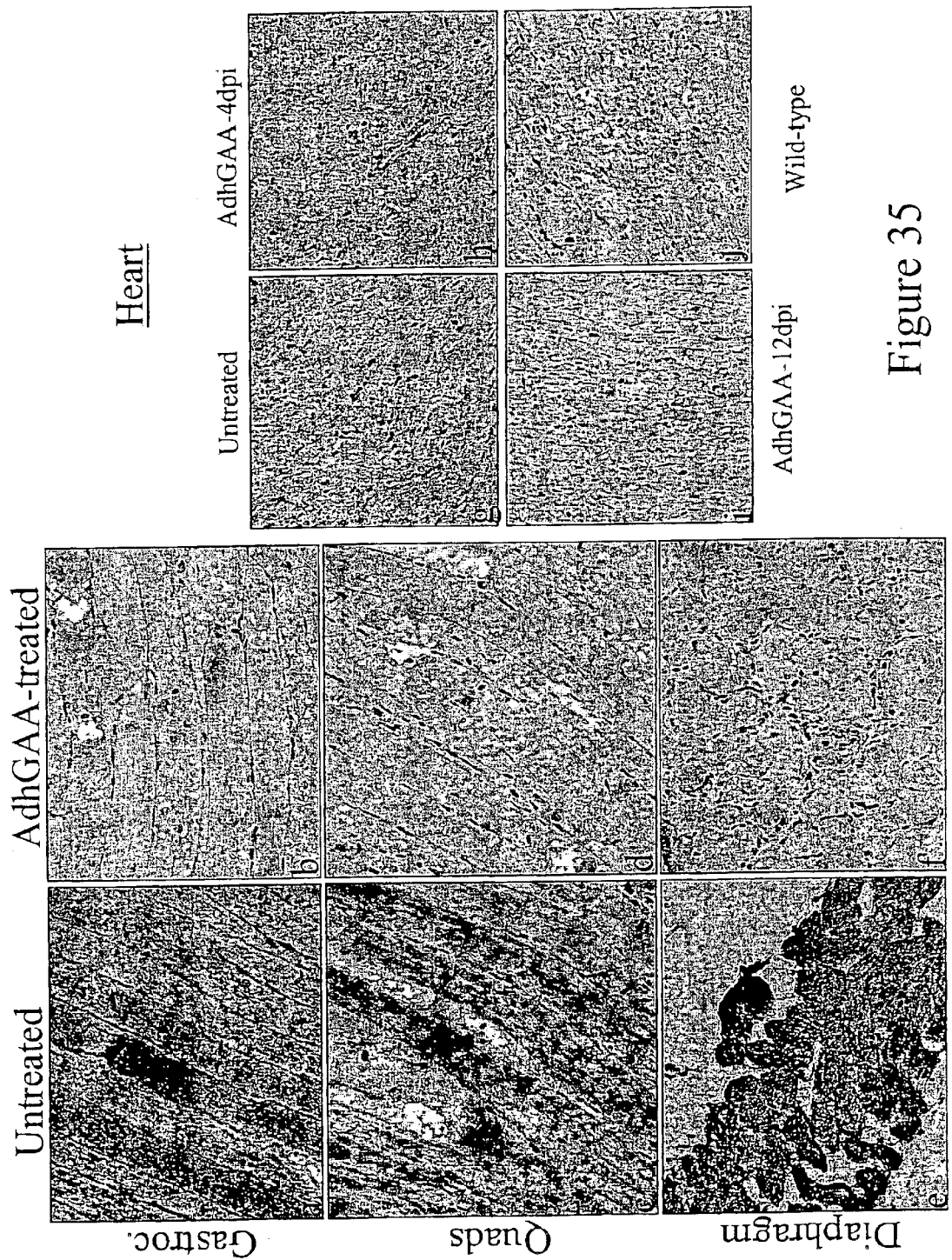
FIG. 35 shows glycogen levels by PAD staining in various tissues of GAA knockout mice 12 days after treatment of the animals with AdhGAAΔpol.

Systemic Reversal of Muscle Glycogen Accumulation in GAA-KO Mice after AdhGAAΔpol This study was undertaken to confirm that the enzyme activities detected in the muscles of the Ad treated GAA-KO mouse resulted in correct lysosomal targeting of the enzyme. Previous studies have demonstrated that exogenously administered precursor GAA can target to lysosomes and act to reduce intra-lysosomal glycogen accumulations in both the AMD quail, and the GAA-KO mouse (Amalfitano et al., (1997) Gene Ther. 4:258; Armentano et al., (1997) J. Virol. 71:2408). Correct lysosomal targeting of the hepatocyte secreted hGAA should also result in a reduction of glycogen accumulation in a number of muscles in the AdhGAAΔpol treated GAA-KO mice. In situ periodic acid-Schiff (PAD) staining for glycogen accumulation in multiple muscles of untreated and AdhGAAΔpol vector treated GAA-KO mice were evaluated (FIG. 35). In each of the respective muscle tissues both granular and diffuse forms of glycogen accumulation (these staining patterns represented accumulation of glycogen in lysosomes and cytoplasm, respectively) were significantly reduced in the AdhGAAΔpol vector treated GAA-KO mice, in comparison to the staining observed in untreated GAA-KO mice. This result was also confirmed after quantification of total intra-cellular glycogen levels in a variety of tissues derived from the treated mice (Table II). The heart and diaphragm muscles appeared to be especially responsive to the AdhGAAΔpol treatment, an important observation since cardiac and/or respiratory muscle involvement are the primary causes of mortality in the various forms of GSD-II. Also of note, exogenous administration of a breast mile-derived form of hGAA did not significantly correct the glycogen accumulations noted in the muscles of GAA-KO mice until 6 months after initiation of therapy, suggesting that hepatically secreted hGAA may be a more potent form of the enzyme (Cox et al., (1993) *Nature* 364:725). These results confirmed that the increased GAA activities noted in the multiple muscles of AdhGAAΔpol vector treated GAA-KO mice resulted in lysosomal targeting of the enzyme, and phenotypic correction of the primary defect in GSD-II, namely significant reductions in muscle cell glycogen accumulation.

It was further observed that in GAA knockout mice less than 2% of wild-type levels of GAA are present in a variety of muscle tissues analyzed, facilitation detection of the exogenously produced hGAA. High levels of hGAA activity were again noted in the serum of infected GAA-KO animals after intravenous administration. Levels similar to that noted after infection of wild type mice. Furthermore, the isoform of the enzyme detected in the serum consisted of substantial amounts of the unprocessed 110 kD precursor form of hGAA, in addition to the processed 76 kD isoform, based upon immunoblotting results (FIG. 32). Importantly, it is the precursor form of GAA that is predicted to be amenable to mannose-6-phosphate uptake mechanisms present in both skeletal and cardiac muscle cells. In further substantiation of this data, even though GAA activities were significantly diminished (less than 90% of wild-type levels) in a variety of tissues in the GAA knockout animals, those animals receiving the AdhGAAΔpol vector of the invention had extremely high levels of GAA activity (exceeding the activities detected in wild-type animals) in all tissues analyzed (FIG. 33). These results demonstrate that after a single, intravenous administration of a modified Ad vector allowing for the extended expression of hGAA, systemic distribution of hGAA to the muscle tissues primarily affected in Pompe's disease can be achieved.

The presence of significant amounts of the precursor hGAA enzyme in the serum of AdhGAA treated animals results in what we believe to be receptor mediated uptake (mannose-6-phosphate or other) and intra-cellular, lysosomal targeting of hGAA. Quantitative measurements of glycogen content of the tissues as determined by enzyme activity assay confirmed that the treated animals showed dramatically reduced glycogen accumulation 12 days after treatment (FIG. 35). It is important to note that despite decreased presence of precursor enzyme in the serum of treated animals at 12 dpi (FIG. 32) glycogen content of the tissues was still significantly reduced, concomitant with persistent GAA enzyme activity in the same tissues at 12 dpi. Therefore this data confirmed that intravenous administration of a modified Ad vector can allow for sustained levels of lysosomal enzymes to be released into the systemic circulation, with subsequent uptake into target tissues where the enzyme can act to correct tissue pathology.

These results demonstrate that the liver can serve as an exocrine gland, that adenovirus vectors of the present invention can infect up to 100% of liver cells after a single intravenous administration, and that sufficient quantities of hGAA are excreted by the infected liver cells to cause dramatically increased enzyme levels of both 76 kD and 110 kD enzyme isoforms in the animal's serum and, finally, that the enzyme is readily taken up by skeletal and cardiac muscle cells of the animal resulting in a dramatic reduction in glycogen accumulations.

TABLE II

| | Glycogen Content (μmole/mg) | | |
|---|---|---|---|
| Tissue | Wild-type | GAA-KO | GAA-KO + AdhGAAΔpol |
| Heart | .0078 ± .0130 | 2.4100 ± .9200 | .0032 ± .0045 |
| Diaphragm | .0390 ± .0350 | .9300 ± .3300 | .1100 ± .1600 |
| Quadriceps | 0 ± 0 | .8800 ± .1200 | .1290 ± .0400 |
| Gastrocnemius | .0365 ± .0260 | .9300 ± .0700 | .1170 ± .1380 |
| Liver | .4600 ± .3800 | .2300 ± .0170 | .0206 ± .0200 |

EXAMPLE 30

Production of Deleted Adenovirus Vectors via Bacterial Homologous Recombination

Here we describe another strategy to rapidly generate multiply deleted recombinant adenoviruses. This strategy approach uses the plasmid pAdEasy1 (an Ad5 viral backbone that is E1 and E3 deleted with a bacterial origin of replication) and a second shuttle plasmid that contains homologous regions to the pAdEasy plasmid as initially described by He et al, (1998) *Proc. Natl. Acad. Sci. USA* 95:2509; U.S. Pat. No. 5,922,576. The homologous regions in the shuttle plasmid flank a multiple cloning site where subcloned transgenes are ligated. When these two plasmids are co-introduced into bacteria (bacteria that allow for increased frequencies of homologous recombination between DNA molecules generally) recombination between the homologous regions of the plasmids results in the generation of a full length adenovirus vector genome, but as a bacterial plasmid containing a bacterial origin of replication and a selectable marker (e.g., kanamycin resistance) Once isolated, the full length vector plasmid is digested with PacI to release the Ad derived genome sequences from the bacterial plasmid sequences, and introduced directly into the appropriate trans-complementing mammalian cell line to begin propagation of the transgene encoding vector.

As originally described by He et al, the pAdEasy system can only generate [E1-, E3-, and/or E4-] Ad vectors. We improved the method of He et al. in order to allow for the construction of Ad vectors deleted not only for E1, E3 and/or E4 genes but also for the polymerase, pTP, 100K, and/or the IVa2 genes.

To facilitate the cloning of deletions we had already generated in Ad5 into pAdEasy1, this plasmid was digested with BamHI to divide the plasmid roughly in half. The larger of the two Bam HI fragments was allowed to re-ligate to itself to form pAdΔBamHI(Δ21696–33422), The pAdΔBamHI(A21696–33422) plasmid contains pAdEasy1 derived sequences except the AdEasy1 sequences 21696–33422. The smaller of the two BamHI fragments contains pAdEasy1 derived sequences 21696–33422 including the E3 deletion, and was cloned into the BamHI site of pcDNA3 (any bacterial plasmid containing BamHI sites and an antibiotic marker could be utilized at this step, pcDNA3 was utilized in this instance) to form pAd(21696–33422). The final daughter plasmids pAdΔBamHI(Δ21696–33422) and pAd(21696–33422) are used as templates for the introduction of other deletions into the Ad genome. Once a deletion has been introduced into either of the two plasmids, (see below) the pAdEasy derived sequences from each plasmid are re-ligated (via BamHI restriction ezyme digestion, isolation of the appropriate subfragments of DNA, and ligated) to form a new parent pAd vector now containing all desired deletions in addition to the original E1 and E3 deletions present in the He et al. constructs. The multiply deleted pAd plasmid is capable of being recombined with any of the shuttle plasmids described by He et al, to generate full Ad vector genomes that are deleted for E1, E3, as well as the polymerase, preterminal protein, IVa2, and/or 100K genes separately, or simultaneously.

EXAMPLE 31

Generation of the Polymerase Deletion within a Parent pAd Plasmid and Subsequent Vector Production pAdΔBamHI(Δ21696–33422) was digested with MunI, and the subfragments of DNA between nucleotides 4036–9158 were replaced with a homologous subfragment of DNA derived from MunI partial digestion of pAdAscLΔpol (Example 2) to successfully produce polymerase deleted Ad vectors. The partial MunI DNA subfragment of pAdAscLΔpol contains the previously described deletion of the polymerase gene (nt. 7274–7882 of the Ad5 genome). The resultant plasmid pAdΔBamHI (Δ21696–33422) Δpol was digested with BamHI, and the ~12 kb BamHI subfragment (encompassing Ad sequences 21696–33422) after BamHI digestion of pAd(21696–33422) was ligated directionally into pAdΔBamHI(Δ21696–33422) Δpol to generate pAdΔpol. This plasmid has been recombined with shuttle plasmids (as described by He et al., (1998) *Proc. Natl. Acad. Sci. USA* 95:2509) containing marker genes (e.g., bacterial β-galactosidase) as well as several versions of the human lysosomal α-glucosidase (GAA) gene (e.g., the 3.3, e.g., h5'sGAA sequence described in Example 23, and 3.8 kb, the GAA sequence from pcDNA3-GAA in Example 23, versions encoding the human GAA precursor, without and with 5' flanking sequences, as described in Van Hove et al., (1996) *Proc. Natl. Acad. Sci. USA* 93:65) flanked by either the CMV enhancer/promoter, or the Elongation factor 1-alpha enhancer/promoter. Homologous recombination between the pAdΔpol and the respective shuttle plasmids resulted in the successful isolation of full length multiply deleted [E1-, E3-,pol-]Ad vector genomes containing the respective transgenes. PacI digestion of the vector genome containing plasmids, followed by transfection into E1 and polymerase expressing cell lines (e.g., B6 or C7) resulted in the successful production and propagation of the desired multiply deleted Ad vectors, only in the respectively transcomplementing cell lines.

EXAMPLE 32

Generation of the Polymerase and Preterminal Protein Deletions within a Parent pAd Plasmid and Subsequent Vector Production pAdΔBamHI(Δ21696–33422) Δpol, was digested with BspEI, effectively cleaving the plasmid into three subfragments, the largest was isolated and ligated to the 2050 bp BspEI subfragment of the plasmid pAdAscLΔpolΔpTP (also referred to a pAdAscLΔpp (1.6)). The 2050 bp subfragment of pAdAscLΔpol, ΔpTP encompasses the pTP deletion (nt 8631–9197). The resultant plasmid pAdΔBamHI(Δ21696–33422) Δpol,ΔpTP was digested with BamHI, and the ~12 kb BamHI subfragment (encompassing Ad sequences 21696–33422) present after BamHI digestion of pAd(21696–33422) was ligated directionally into pAdΔBamHI(Δ21696–33422) Δpol, ΔpTP, to generate pAdΔpol,ΔpTP. This plasmid has been recombined with shuttle plasmids (as described by He et al., (1998) *Proc. Natl. Acad. Sci. USA* 95:2509) containing marker genes (e.g., bacterial β-galactosidase) as well as several versions of the human lysosomal α-glucosidase (GAA) gene encoding the human GAA precursor, without and with 5' flanking sequences (e.g., the 3.3 and 3.8 kb versions, for example, the h5'sGAA and GAA sequences in Example 23), as described in Van Hove et al., (1996) *Proc. Natl. Acad. Sci. USA* 93:65) flanked by either the CMV enhancer/promoter, or the Elongation factor 1-alpha enhancer/promoter. Homologous recombination between the pAdΔpol, ΔpTP and the respective shuttle plasmids resulted in the successful isolation of full length multiply deleted [E1-,E3-,pol-,pTP-]Ad vector genomes containing the respective transgenes. PacI digestion of the vector genome containing plasmids, followed by transfection into E1, polymerase, and preterminal protein expressing cell lines (e.g., C7) resulted in the successful production and propagation of the desired multiply deleted Ad vectors only in the respectively transcomplementing cell lines.

EXAMPLE 33

Figure 36:
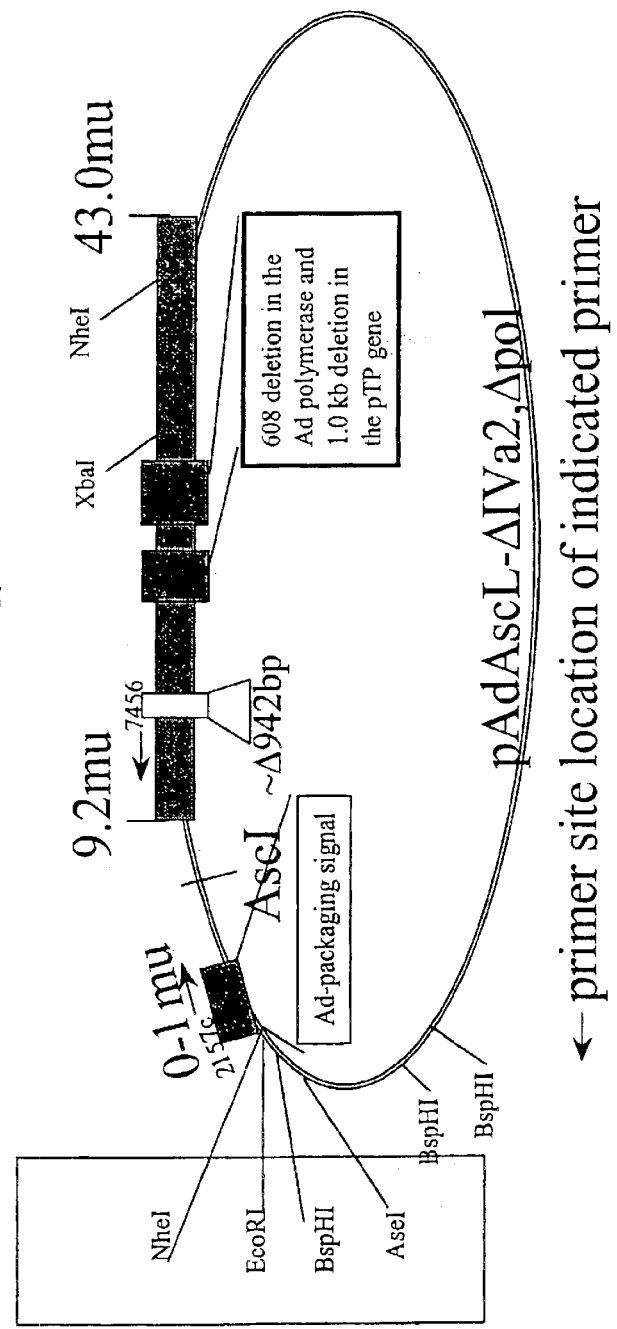
FIG. 36 shows the structure of shuttle plasmid pAdAscL-ΔIVa2, Δpp-1.6 kb.

Generation of the IVa2, Polymerase, and Preterminal Protein Deletions within a Parent pAd Plasmid pAdΔBamHI(Δ21696–33422) Δpol, was digested with MunI, and the subfragments of DNA between nucleotides 4036–9158 were replaced with a homologous subfragment of DNA derived from MunI partial digestion of pAdAscLΔIVa2, Δpol, ΔpTP (also called pAdAscLΔIVa2, Δpp (1.6); FIG. 36) to successfully produce E1, polymerase, pTP, and IVa2 deleted Ad vectors. The partial MunI DNA subfragment of pAdAscLΔIVa2, Δpol, ΔpTP contains the previously described deletion of the polymerase gene (nt. 7274–7882 of the Ad5 genome) the preterminal protein gene (nt 8631–9197 of the Ad5 genome), and the IVa2 deletion (nt 4830–5766 of the Ad5 genome). The resultant plasmid pAdΔBamHI(Δ21696–33422) ΔIVa2, Δpol,ΔpTP was digested with BamHI, and the ~12 kb BamHI subfragment (encompassing Ad sequences 21696–33422) released after BamHI digestion of pAd(21696–33422) was ligated directionally into pAdΔBamHI(Δ21696–33422) ΔIVa2, Δpol, ΔpTP, to generate pAdΔIVa2, Δpol, ΔpTP. The vector [E1-, E3-, (Va2-, pol-, pTP-(1.6)]Ad is generated following the techniques provided herein or other techniques known in the art.

This plasmid is recombined with any of the previously described shuttle plasmids (containing for example marker genes, the GAA genes, or any other DNA sequence) to generate the respectively deleted Ad vectors in the appropriate trans-complementing cell lines.

Routine modifications of the techniques described in the preceding paragraphs are used to generate [E1-, E3-, IVa2-] Ad, [E1-, E3-, IVa2-, pol-]Ad, and [E1-, E3-, IVa2-, pol-, pTP-(2.4)]Ad from the shuttle plasmids pAdAscLΔIVa2 (FIG. 19), pAdAscLΔIVa2, Δpol (FIG. 38), and pAdAscLΔIVa2, Δpp (2.4) (FIG. 37), respectively.

EXAMPLE 34

Generation of the 100K Deletion within a Parent pAd Plasmid and Subsequent Vector Production pAdΔBamHI(21696–33422) a 17.1 kb plasmid containing Ad derived sequence that also encompass the entire 100K gene, was digested with Nhe I to generate three DNA subfragments. Nhe I restriction digestion removes a 687 bp fragment within the 100K gene between sequences 24999 to 25686 of the Ad5 genome. An additional Nhe I site at sequence 31509 of the Ad5 genome liberates a 3143 bp fragment as well as the remaining 13,302 bp fragment of the pAd(21696–33422) plasmid. Careful attention was given to ensure that the 687 bp deletion does not interfere with other potential reading frames that overlap 100K or lie on the opposite coding strand of 100K. To generate pAd (21696–33422) Δ100K, the 13,302 bp Nhe I digested pAd (21696–33422) subfragment was ligated to the 3143 bp Nhe I fragment. This plasmid was digested with BamHI, and the DNA subfragment was ligated in the correct orientation into BamHI digested pAdΔBamHI(Δ21696–33422), to generate pAdΔ100K. The pAdΔ100K has been recombined with shuttle plasmids that contained marker genes (e.g., the bacterial B-galactosidase flanked by the CMV enhancer/promoter).

Homologous recombination between the pAdΔ100K and the respective shuttle plasmids resulted in the successful isolation of full length multiply deleted [E1-,100K-] Ad vector genomes containing the respective transgenes. PacI digestion of the vector genome containing plasmids, followed by transfection into E1, and 100K expressing cell lines resulted in the successful production and propagation of the desired, multiply deleted Ad vectors. These viruses were found to have a 50 fold increased ability to propagate and produce infectious transducing units in the E1 and 100K expressing cell lines, as compared to cells only expressing the E1 genes, confirming that the 100K deletion is a significant deletion that incapacitates vectors containing it.

This pAdΔ100K plasmid is recombined with any of the previously described shuttle plasmids (containing for example marker genes, the GAA genes, or any other DNA sequence) to generate the respectively deleted Ad vectors in the appropriate trans-complementing cell lines.

EXAMPLE 35

Generation of the IVa2, Polymerase, Preterminal Protein, and 100K Deletions Within a Parent pAd Plasmid for Subsequent Vector Production pAdΔBamHI(Δ21696–33422) ΔIVa2, Δpol, ΔpTP is digested with BamHI. The polymerase, preterminal protein, and IVa2 deletions are ligated into the BamHI subfragment of pAd(21696–33422) Δ100K encompassing the 100K deletion to generate pAdΔIVa2, Δpol, ΔpTP, Δ100K. The vector [E1-, E3-, IVa2-, pol-, pTP-(1.6), 100K-]Ad is generated following the techniques provided herein or other techniques known in the art.

This plasmid is recombined with any of the previously described shuttle plasmids (containing for example marker genes, the GAA genes, or any other DNA sequence) to generate the respectively deleted Ad vectors in the appropriate trans-complementing cell lines.

EXAMPLE 36

Adh5'sGAAΔpol, Ad/EF1-α/hGAAΔpol, and Ad/EF1-α/h5'sGAAΔpol

Using routine modifications of the methods described in Example 30 regarding production of adenovirus vectors using bacterial homologous recombination AdhGAAΔpol (CMV promoter) Adh5'sGAAΔpol (CMV promoter), and Ad/EF1-α/hGAAΔpol (EF1-α promoter) have been generated. The 5'sGAA sequence is the sequence of pcDNA3–5'sGAA (Example 23), which lacks most of the 5' untranslated sequences of the hGAA gene. In addition, using routine modifications of the methods described herein, Ad/EF1-α/h5'sGAAΔpol (EF1-α and shorted hGAA gene) is generated.

These vectors are administered to mice or other subjects in vivo, including mammalian subjects, in particular, human subjects. In particular, these vectors are administered to subjects with GAA deficiency to achieve a therapeutic effect (as described hereinabove).

In particular, these vectors are administered to wild-type or GAA-KO mice and tissue/plasma GAA activity and glycogen accumulation/depletion is monitored as described in Example 25.

EXAMPLE 37

AdhGAAΔpp, Adh5'sGAAΔpp, Ad/EF1-α/hGAAΔpp, and Ad/EF1-α/h5'sGAAΔpp

Using routine modifications of the methods described in Example 30 regarding the production of adenovirus vectors using bacterial homologous recombination AdhGAAΔpp (CMV promoter) and Adh5'sGAAΔpp (CMV promoter) have been generated. The Δpol, ΔpTP deletions are as described in Example 3 for AdLacZΔpp (deletions from about nucleotides 7274 to 7881 and from about nucleotides 9198 to 9630 of the Ad5 genome). The 5'sGAA sequence is the sequence of pcDNA3–5'sGAA (Example 23), which lacks most of the 5' untranslated sequences of the hGAA gene. In addition, using routine modifications of the methods described herein, Ad/EF1-α/hGAAΔpp (EF1-α promoter) and Ad/EF1-α/h5'sGAAΔpol (EF1-α and shorted hGAA gene) are generated.

These vectors are administered to mice or other subjects in vivo, including mammalian subjects, in particular, human subjects. In particular, these vectors are administered to subjects with GAA deficiency to achieve a therapeutic effect (as described hereinabove).

In particular, these vectors are administered to wild-type or GAA-KO mice and tissue/plasma GAA activity and glycogen accumulation/depletion is monitored as described in Example 25.

All patent publications cited in this specification are hereby incorporated by reference in their entirety as if each individual publication was specifically and individually indicated to be incorporated by reference.

As will be apparent to those skilled in the art to which the invention pertains, the present invention may be embodied in forms other than those specifically disclosed above without departing form the spirit or essential characteristics of the invention. The particular embodiments of the invention described above are, therefore, to be considered as illustrative and not restrictive. The scope of the invention is as set forth in the appended claims rather than being limited to the examples contained in the foregoing description.

---

That which is claimed is:

1. A propagation-defective adenovirus vector comprising a recombinant adenovirus genome comprising a heterologous nucleotide sequence, wherein the genome lacks a coding sequence for a functional adenovirus 100K protein, and wherein said adenovirus vector can be propagated in a transcomplementing cell in the absence of a helper.

2. The adenovirus vector of claim 1, wherein said adenovirus genome further lacks an E1 region or comprise an E1 region comprising one or more deletion(s) therein.

3. The adenovirus vector of claim 1, wherein said adenovirus genome further lacks an E3 region or comprises an E3 region comprising one or more deletion(s) therein.

4. The adenovirus vector of claim 1, wherein of said adenovirus genome comprises a 100K region comprising a deletion at about nucleotides 24,990 to 25,687 of the adenovirus serotype 5 genome or a corresponding region of the genome of adenoviruses of other serotypes.

5. The adenovirus vector of claim 2, wherein said adenovirus vector is disclosed herein as [E1⁻, 100K]Ad.

6. The adenovirus vector of claim 1, wherein said heterologous nucleotide sequence is operatively associated with expression control sequences.

7. The adenovirus vector of claim 6, wherein said expression control sequences include a promoter.

8. The adenovirus vector of claim 7, wherein said promoter is selected from the group consisting of liver-specific, muscle-specific, and brain-specific promoters.

9. The adenovirus vector of claim 7, wherein said promoter is selected from the group consisting of the CMV promoter, albumin promoter, EF1-α promoter, PγK promoter, MFG promoter, and Rous sarcoma virus promoter.

10. The adenovirus vector of claim 1 wherein said adenovirus genome further comprises an adenovirus E1A enhancer sequence.

11. The adenovirus vector of claim 1, wherein said heterologous nucleotide sequence encodes a protein or peptide.

12. The adenovirus vector of claim 11, wherein said protein or peptide is a therapeutic protein or peptide.

13. The adenovirus vector of claim 11, wherein said protein or peptide is an immunogenic protein or peptide.

14. The adenovirus vector of claim 11, wherein said protein or peptide is a reporter protein or peptide.

15. The adenovirus vector of claim 1, wherein said heterologous nucleotide sequence encodes an antisense nucleotide sequence or non-translated DNA.

16. The adenovirus vector of claim 11, wherein said protein or peptide is a lysosomal protein.

17. The adenovirus vector of claim 11, wherein said protein or peptide is associated with a metabolic disorder.

18. The adenovirus vector of claim 11, wherein said protein or peptide is associated with a lysosomal storage disease.

19. The adenovirus vector of claim 18, wherein said protein or peptide is selected from the group consisting of β-galactosidase, β-hexosaminidase A, β-hexosaminidase B, GM₂ activator protein, glucocerebrosidase, arylsulfatase A, galactosylceramidase, acid sphingomyelinase, acid ceramidase, acid lipase, α-L-iduronidase, iduronate sulfatase, heparan N-sulfatase, α-N-acetylglucosaminidase acetyl-CoA, glucosaminide acetyltransferase, N-acetylglucosamine-6-sulfatase, arylsulfatase B, β-glucuronidase, α-mannosidase, β-mannosidase, α-L-fucosidase, N-aspartyl-β-glucosaminidase, α-neuraminidase, lysosomal protective protein, α-N-acetylgalactosaminidase, N-acetylglucosamine-1-phosphotransferase, cystine transport protein, sialic acid transport protein, the CLN3 gene product, palmitoyl-protein thioesterase, saposin A, saposin B, saposin C, and saposin D.

20. The adenovirus vector of claim 17, wherein said protein or peptide is associated with a glycogen storage disease.

21. The adenovirus vector of claim 20, wherein said protein or peptide is selected from the group consisting of glucose 6-phosphatase, lysosomal acid α glucosidase, glycogen debranching enzyme, branching enzyme, muscle phosphorylase, liver phosphorylase, phosphorylase kinase, muscle phosphofructokinase, glycogen synthase, phosphoglucoisomerase, muscle phosphoglycerate kinase, phosphoglycerate mutase, and lactate dehydrogenase.

22. A propagation-defective adenovirus vector comprising a recombinant adenovirus genome comprising a heterologous nucleotide sequence encoding a lysosomal acid α-glucosidase, wherein the genome lacks a coding sequence for a functional adenovirus 100K protein, and wherein said adenovirus vector can be propagated in a transcomplementing cell in the absence of a helper.

23. The adenovirus vector of claim 22, wherein said adenovirus genome comprises a polymerase region comprising a deletion at about nucleotides 7274 to 7881 of the adenovirus serotype 5 genome or a corresponding region of the genome of adenoviruses of other serotypes.

24. The adenovirus vector of claim 22, wherein said adenovirus comprises a preterminal protein region comprising a deletion at about nucleotides 9198 to 9630 of the adenovirus serotype 5 genome or a corresponding region of the genome of adenoviruses of other serotypes.

25. The adenovirus vector of claim 22, wherein said adenovirus genome (a) lacks a polymerase region or comprises a polymerase region comprising one or more deletions therein and (b) lacks a preterminal protein region or comprises a preterminal protein region comprising one or more deletions therein.

26. The adenovirus vector of claim 22, wherein said heterologous nucleotide sequence is operatively associated with a promoter.

27. The adenovirus vector of claim 26, wherein said promoter is selected from the group consisting of liver-specific and muscle-specific promoters.

28. The adenovirus vector of claim 26, wherein said promoter is selected from the group consisting of the CMV promoter, albumin promoter, EF1-α promoter, PγK promoter, MFG promoter, and Rous sarcoma virus promoter.

29. The adenovirus vector of claim 22, wherein said lysosomal acid α-glucosidase is human lysosomal acid α-glucosidase.

30. The adenovirus vector of claim 22, wherein said adenovirus genome comprises a 100K region comprising a deletion at about nucleotides 24,990 to 25,687 of the adenovirus serotype 5 genome or a corresponding region of the genome of adenoviruses of other serotypes.

31. The adenovirus vector of claim 22, wherein said adenovirus genome comprises a IVa2 region comprising a deletion at about nucleotides 4830 to 5766 of the adenovirus serotype 5 genome or a corresponding region of adenoviruses of other serotypes.

32. An isolated mammalian cell comprising the adenovirus vector of claim 1.

33. The cell of claim 32, wherein said adenovirus comprises one or more heterologous nucleotide sequences encoding a protein or peptide.

34. An isolated mammalian cell comprising the adenovirus vector of claim 22.

35. An isolated mammalian cell comprising an isolated DNA comprising a nucleotide sequence encoding an adenovirus 100K protein, wherein said isolated DNA is stably integrated into the genome of said cell, and wherein said cell can propagate an adenovirus genome that essentially lacks expression of a functional 100K protein.

36. The cell of claim 35, wherein said cell is a K-16 cell.

37. The cell of claim 35, wherein said nucleotide sequence further encodes a constitutive promoter that is operatively associated with the sequence encoding said adenovirus 100K protein.

38. The cell of claim 37, wherein said cell is a C7 cell constitutively expressing the 100K protein.

39. The cell of claim 35, wherein said nucleotide sequence encodes an inducible promoter that is operatively associated with the sequence encoding said adenovirus 100K protein.

40. The cell of claim 35, further comprising a recombinant adenovirus genome, wherein said adenovirus genome lacks a coding sequence for a functional 100K protein.

41. An isolated DNA comprising a recombinant adenovirus genome comprising a heterologous nucleotide sequence, wherein the genome lacks a coding sequence for a functional adenovirus 100K protein, and wherein said recombinant adenovirus genome can be propagated in a transcomplementing cell in the absence of a helper.

42. The isolated DNA of claim 41, wherein said adenovirus genome comprises a 100K region comprising a deletion at about nucleotides 24,990 to 25,687 of the adenovirus serotype 5 genome or a corresponding region of the genome of adenoviruses of other serotypes.

43. A vector comprising the isolated DNA of claim 41.

44. The vector of claim 43, wherein said vector is a plasmid.

45. The vector of claim 44, wherein said vector is disclosed herein as pcDNA3+100K.

46. A method of producing a propagation-defective adenovirus vector, comprising:
    introducing the propagation-defective adenovirus vector of claim 1 into a mammalian cell;
    wherein the mammalian cell expresses a functional adenovirus 100K protein and transcomplements the function(s) lacking from the adenovirus genome; and
    collecting the propagation-defective adenovirus vector produced by said mammalian cell.

47. The method of claim 46, wherein the collected adenovirus vector has a titer of at least 100 infectious units per cell.

48. The method of claim 46, wherein the adenovirus genome further lacks an E1 region or comprises an E1 region comprising one or more deletion(s) therein.

49. The method of claim 46, wherein the adenovirus genome further lacks an E3 region or comprises an E3 region comprising one or more deletion(s) therein.

50. The method of claim 46, wherein the adenovirus genome further lacks a polymerase region or comprises a polymerase region comprising one or more deletion(s) therein.

51. The method of claim 46, wherein the adenovirus genome comprises a 100K region comprising a deletion at about nucleotides 24,990 to 25,687 of the adenovirus serotype 5 genome or a corresponding region of the genome of adenoviruses of other serotypes.

52. The method of claim 51 wherein the adenovirus vector is disclosed herein as [E1$^-$, 100K]Ad.

53. The method of claim 46, wherein the mammalian cell comprises a nucleotide sequence encoding a functional adenovirus 100K protein stably integrated into the genome of the mammalian cell.

54. The method of claim 53, wherein the mammalian cell is a K-16 cell.

55. The method of claim 53, wherein the mammalian cell constitutively expresses the functional adenovirus 100K protein.

56. The method of claim 55, wherein the mammalian cell is a C7 cell constitutively expressing the functional adenovirus 100K protein.

57. A composition comprising a plurality of the propagation-defective adenovirus vector produced by the method of claim 46.

58. A method of producing a propagation-defective adenovirus vector, comprising:

introducing a bacterial plasmid comprising a recombinant adenovirus genome into a bacterial cell, wherein said adenovirus genome comprises a heterologous nucleotide sequence and lacks a coding sequence for a functional adenovirus 100K protein, and wherein said adenovirus genome can be propagated in a transcomplementing cell in the absence of a helper;

amplifying the bacterial plasmid in the bacterial cell;

recovering the amplified bacterial plasmid from the bacterial cell;

linearizing the recovered bacterial plasmid;

introducing the linearized plasmid into a mammalian cell that transcomplements the deleted functions in the adenovirus genome; and collecting the propagation-defective adenovirus vector.

59. The method of claim 58, wherein the heterologous nucleotide sequence encodes a lysosomal acid α-glucosidase.

60. A method of producing a gutted adenovirus containing a minichromosome, comprising:

introducing into a mammalian cell expressing a functional adenovirus 100K protein;

a plasmid comprising an adenovirus inverted terminal repeat (ITR), an adenovirus packaging sequence, and a heterologous nucleotide sequence, and a helper adenovirus comprising a recombinant adenovirus genome that lacks a coding sequence for a functional 100K protein;

collecting the gutted adenovirus containing the minichromosome from the mammalian cell.

61. The method of claim 60, wherein the adenovirus genome comprises a 100K region comprising a deletion at about nucleotides 24,990 to 25,687 of the adenovirus serotype 5 genome or a homologous region adenoviruses of other serotypes.

62. The method of claim 60, wherein the helper adenovirus is disclosed herein as [E1−, 100K]Ad.

63. The method of claim 60, wherein the adenovirus genome further lacks a coding sequence for a functional adenovirus IVa2 protein and the mammalian cell expresses a functional IVa2 protein.

64. The method of claim 60, wherein the adenovirus genome further lacks a coding sequence for a functional adenovirus polymerase protein and the mammalian cell expresses a functional polymerase protein.

65. The method of claim 60, wherein the adenovirus genome further lacks a coding sequence for a functional adenovirus preterminal protein and the mammalian cell expresses a functional preterminal protein.

66. The method of claim 60, wherein the nucleotide sequence encoding the functional adenovirus 100K protein is stably integrated into the genome of the mammalian cell.

67. The method of claim 66, wherein the mammalian cell is a K-16 cell.

68. The method of claim 60, wherein the mammalian cell constitutively expresses the functional adenovirus 100K protein.

69. The method of claim 68, wherein said mammalian cell is a C7 cell constitutively expressing the functional adenovirus 100K protein.

70. The method of claim 60, wherein the helper adenovirus lacks a packaging sequence.

71. The method of claim 60, wherein the helper adenovirus has a modified packaging signal that does not promote the encapsidation of the plasmid.

72. The method of claim 60, wherein the helper adenovirus further comprises lox sites flanking the packaging sequence and the mammalian cell produces the cre recombinase protein.

73. A method of delivering a nucleotide sequence into a cell comprising introducing into the cell a composition comprising a plurality of the gutted adenovirus of claim 60.

74. The method of claim 73, wherein said introducing is carried out in vivo.

75. The method of claim 60, further comprising the step of separating the gutted adenovirus from contaminating helper adenovirus.

* * * * *

UNITED STATES PATENT AND TRADEMARK OFFICE
CERTIFICATE OF CORRECTION

PATENT NO.    : 6,797,265 B2
DATED         : September 28, 2004
INVENTOR(S)   : Amalfitano et al.

It is certified that error appears in the above-identified patent and that said Letters Patent is hereby corrected as shown below:

Column 29,
Lines 35-38, should read -- Construction of [E1-, Δpol, E3-] and [E1-, Δpol, ΔpTP, E3-] Ad Vectors --

Column 31,
Line 60, should read -- mm Tris·Cl (pH 8.0), sonicated, and the virus purified by two --

Column 57,
Line 40, claim 4 should read -- 4. The adenovirus of Claim 1, wherein said adenovirus genome comprises a 100K region comprising a deletion at about nucleotides 24,990 to 25,687 of the adenvirus serotype 5 genome or a corresponding region of the genome of adenoviruses of other serotypes. --
Line 45, claim 5 should read -- 5. The adenovirus vector of Claim 4, wherein said adenovirus vector is disclosed herein as [E1¨, 100K¨]Ad. --

Column 58,
Line 38, claim 18 should read -- 18. The adenovirus vector of Claim 17, wherein said protein or peptide is associated with a lysosomal storage disease. --

Column 59,
Line 65, claim 35 should read -- 35. An isolated mammalian cell comprising an isolated DNA comprising a nucleotide sequence encoding an adenovirus 100K protein, wherein said isolated DNA is stably intergrated into the genome of said cell, and wherein said cell can propagate an adenovirus genome that essentially lacks expression of a functional adenovirus 100K protein. --

Column 60,
Line 4, claim 40 should read -- 40. The cell of Claim 35, further comprising a recombinant adenvirus genome, wherein said adenovirus genome lacks a coding sequence for a functional adenovirus 100K protein. --
Line 49, claim 52 should read -- 52. The method of Claim 51, wherein the adenovirus vector is disclosed herein as [E1¨, 100K¨]Ad. --

UNITED STATES PATENT AND TRADEMARK OFFICE
CERTIFICATE OF CORRECTION

PATENT NO. : 6,797,265 B2
DATED : September 28, 2004
INVENTOR(S) : Amalfitano et al.

It is certified that error appears in the above-identified patent and that said Letters Patent is hereby corrected as shown below:

<u>Column 61,</u>
Line 37, claim 62 should read -- 62. The method of Claim 60, wherein the helper adenovirus is disclosed herein as [E1⁻, 100K]Ad. --

Signed and Sealed this

First Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,797,265 B2
DATED : September 28, 2004
INVENTOR(S) : Amalfitano et al.

It is certified that error appears in the above-identified patent and that said Letters Patent is hereby corrected as shown below:

Column 57,
Lines 45 and 46, should read -- 5. The adenovirus vector of Claim 4, wherein said adenovirus vector is disclosed herein as [$E1^-$, $100K^-$]Ad. --

Column 60,
Lines 49 and 50, should read -- 52. The method of Claim 51, wherein the adenovirus vector is disclosed herein as [$E1^-$, $100K^-$]Ad. --

Column 61,
Lines 37 and 38, should read -- 62. The method of Claim 60, wherein the helper adenovirus is disclosed herein as [$E1.^-$, $100K^-$]Ad. --

Signed and Sealed this

Twenty-fourth Day of May, 2005

JON W. DUDAS
*Director of the United States Patent and Trademark Office*